US009358004B2

(12) United States Patent
Sniffin et al.

(10) Patent No.: US 9,358,004 B2
(45) Date of Patent: Jun. 7, 2016

(54) ARTICULATING APPARATUS FOR ENDOSCOPIC PROCEDURES

(71) Applicant: Covidien LP, Mansfield, MA (US)

(72) Inventors: Kevin Sniffin, Danbury, CT (US); Mark Russo, Plantsville, CT (US); Gregory Fischvogt, Hamden, CT (US); Jay Breindel, Kensington, CT (US)

(73) Assignee: Covidien LP, Mansfield, MA (US)

( * ) Notice: Subject to any disclaimer, the term of this patent is extended or adjusted under 35 U.S.C. 154(b) by 222 days.

(21) Appl. No.: 13/974,338

(22) Filed: Aug. 23, 2013

(65) Prior Publication Data
US 2015/0005789 A1 Jan. 1, 2015

Related U.S. Application Data

(63) Continuation-in-part of application No. 13/930,770, filed on Jun. 28, 2013.

(51) Int. Cl.
*A61B 17/04* (2006.01)
*A61B 17/10* (2006.01)
(Continued)

(52) U.S. Cl.
CPC ..... *A61B 17/068* (2013.01); *A61B 2017/00323* (2013.01); *A61B 2017/00473* (2013.01); *A61B 2017/0648* (2013.01);
(Continued)

(58) Field of Classification Search
CPC ................. A61B 2017/003; A61B 2017/2905; A61B 2017/2908; A61B 17/1155
USPC ........................................... 227/175.1–182.1
See application file for complete search history.

(56) References Cited

U.S. PATENT DOCUMENTS 3,866,510 A 2/1975 Eibes et al.
4,884,572 A 12/1989 Bays
(Continued)

FOREIGN PATENT DOCUMENTS

DE 10300787 A1 9/2004
DE 10 2010 015009 A1 10/2011
(Continued)

OTHER PUBLICATIONS

Extended European Search Report corresponding to EP No. 11 25 0549.0, completed Sep. 9, 2013 and mailed Sep. 17, 2013; 9 pages.
(Continued)

*Primary Examiner* — Robert Long

(57) ABSTRACT

According to an aspect of the present disclosure, an endoscopic surgical device is provided. The surgical device includes a handle assembly including a drive mechanism actuatable by a trigger; and an endoscopic assembly including a proximal end portion extending from the handle assembly; a distal end portion pivotably connected to the proximal end portion of the endoscopic assembly; and a rotatable inner actuation shaft extending from the handle assembly and into the distal end portion of the endoscopic assembly, the inner actuation shaft including a flexible portion extending across the pivot connection. The surgical device includes an end effector selectively connectable to the distal end portion of the endoscopic assembly and to a distal portion of the rotatable inner actuation shaft. The end effector includes a splined inner tube rotatably supported in an outer tube; and a plurality of surgical anchors loaded in the inner tube of the end effector.

12 Claims, 36 Drawing Sheets

(51) Int. Cl.
*A61B 17/068* (2006.01)
*A61B 17/00* (2006.01)
*A61B 17/064* (2006.01)
*A61B 17/29* (2006.01)

(52) U.S. Cl.
CPC ... *A61B 2017/2903* (2013.01); *A61B 2017/2923* (2013.01); *A61B 2017/2927* (2013.01)

(56) References Cited

U.S. PATENT DOCUMENTS

| | | |
|---|---|---|
| 5,085,661 A | 2/1992 | Moss |
| 5,171,247 A | 12/1992 | Hughett |
| 5,171,249 A | 12/1992 | Stefanchik |
| 5,176,306 A | 1/1993 | Heimerl |
| 5,207,697 A | 5/1993 | Carusillo |
| 5,228,256 A | 7/1993 | Dreveny |
| 5,236,563 A | 8/1993 | Loh |
| 5,246,441 A | 9/1993 | Ross |
| 5,246,450 A | 9/1993 | Thornton |
| 5,312,023 A | 5/1994 | Green |
| 5,330,487 A | 7/1994 | Thornton |
| 5,344,061 A | 9/1994 | Crainich |
| 5,356,064 A | 10/1994 | Green |
| 5,382,254 A | 1/1995 | McGarry |
| 5,398,861 A | 3/1995 | Green |
| 5,403,327 A | 4/1995 | Thornton |
| 5,433,721 A | 7/1995 | Hooven |
| 5,439,468 A | 8/1995 | Schulze |
| 5,466,243 A | 11/1995 | Schmieding |
| 5,467,911 A | 11/1995 | Tsuruta |
| 5,474,566 A | 12/1995 | Alesi |
| 5,474,567 A | 12/1995 | Stefanchik |
| 5,522,844 A | 6/1996 | Johnson |
| 5,527,319 A | 6/1996 | Green |
| 5,553,765 A | 9/1996 | Knodel |
| 5,562,685 A | 10/1996 | Mollenauer |
| 5,564,615 A | 10/1996 | Bishop |
| 5,582,615 A | 12/1996 | Foshee |
| 5,582,616 A | 12/1996 | Bolduc |
| 5,584,425 A | 12/1996 | Savage |
| 5,588,581 A | 12/1996 | Conlon |
| 5,601,571 A | 2/1997 | Moss |
| 5,601,573 A | 2/1997 | Fogelberg |
| 5,607,436 A * | 3/1997 | Pratt ............... A61B 17/1285 227/901 |
| 5,626,613 A | 5/1997 | Schmieding |
| 5,628,752 A | 5/1997 | Asnis |
| 5,649,931 A | 7/1997 | Bryant |
| 5,662,662 A | 9/1997 | Bishop |
| 5,681,330 A | 10/1997 | Hughett |
| 5,683,401 A | 11/1997 | Schmieding |
| 5,685,474 A | 11/1997 | Seeber |
| 5,697,935 A | 12/1997 | Moran |
| 5,704,534 A * | 1/1998 | Huitema ......... A61B 17/07207 227/175.1 |
| 5,709,692 A | 1/1998 | Mollenauer |
| 5,728,116 A | 3/1998 | Rosenman |
| 5,730,744 A | 3/1998 | Justin |
| 5,732,806 A | 3/1998 | Foshee |
| 5,735,854 A | 4/1998 | Caron |
| 5,741,268 A | 4/1998 | Schutz |
| 5,762,255 A | 6/1998 | Chrisman |
| 5,782,844 A | 7/1998 | Yoon |
| 5,792,165 A * | 8/1998 | Klieman ............... A61B 17/29 606/170 |
| 5,810,882 A | 9/1998 | Bolduc |
| 5,824,008 A | 10/1998 | Bolduc |
| 5,830,221 A | 11/1998 | Stein |
| 5,843,087 A | 12/1998 | Jensen |
| 5,897,564 A | 4/1999 | Schulze |
| 5,904,693 A | 5/1999 | Dicesare |
| 5,910,105 A | 6/1999 | Swain |
| 5,911,722 A | 6/1999 | Adler |
| 5,928,244 A | 7/1999 | Tovey |
| 5,928,252 A | 7/1999 | Steadman |
| 5,931,844 A | 8/1999 | Thompson |
| 5,941,439 A | 8/1999 | Kammerer |
| 5,954,259 A | 9/1999 | Viola |
| 5,961,524 A | 10/1999 | Crombie |
| 5,964,772 A | 10/1999 | Bolduc |
| 5,976,160 A | 11/1999 | Crainich |
| 5,997,552 A | 12/1999 | Person |
| 6,010,513 A | 1/2000 | Tormala |
| 6,013,991 A | 1/2000 | Philipp |
| 6,039,753 A | 3/2000 | Meislin |
| 6,074,395 A | 6/2000 | Trott |
| 6,099,537 A | 8/2000 | Sugai |
| 6,126,670 A | 10/2000 | Walker |
| 6,132,435 A | 10/2000 | Young |
| 6,146,387 A | 11/2000 | Trott |
| 6,183,479 B1 | 2/2001 | Tormala |
| 6,228,098 B1 | 5/2001 | Kayan |
| 6,235,058 B1 | 5/2001 | Huene |
| 6,241,736 B1 | 6/2001 | Sater |
| 6,261,302 B1 | 7/2001 | Voegele |
| 6,296,656 B1 | 10/2001 | Bolduc |
| 6,330,964 B1 | 12/2001 | Kayan |
| 6,387,113 B1 | 5/2002 | Hawkins |
| 6,402,757 B1 | 6/2002 | Moore, III |
| 6,425,900 B1 | 7/2002 | Knodel |
| 6,439,446 B1 | 8/2002 | Perry |
| 6,440,136 B1 | 8/2002 | Gambale |
| 6,450,391 B1 | 9/2002 | Kayan |
| 6,457,625 B1 | 10/2002 | Tormala |
| 6,551,333 B2 | 4/2003 | Kuhns |
| 6,562,051 B1 | 5/2003 | Bolduc |
| 6,572,626 B1 | 6/2003 | Knodel |
| 6,589,249 B2 | 7/2003 | Sater |
| 6,626,916 B1 | 9/2003 | Yeung |
| 6,632,228 B2 | 10/2003 | Fortier |
| 6,652,538 B2 | 11/2003 | Kayan |
| 6,663,656 B2 | 12/2003 | Schmieding |
| 6,666,854 B1 | 12/2003 | Lange |
| 6,695,867 B2 | 2/2004 | Ginn |
| 6,733,506 B1 | 5/2004 | McDevitt |
| 6,743,240 B2 | 6/2004 | Smith |
| 6,749,621 B2 | 6/2004 | Pantages |
| 6,755,836 B1 | 6/2004 | Lewis |
| 6,773,438 B1 | 8/2004 | Knodel |
| 6,824,548 B2 | 11/2004 | Smith |
| 6,837,893 B2 | 1/2005 | Miller |
| 6,840,943 B2 | 1/2005 | Kennefick |
| 6,843,794 B2 | 1/2005 | Sixto |
| 6,869,435 B2 | 3/2005 | Blake, III |
| 6,884,248 B2 | 4/2005 | Bolduc |
| 6,887,244 B1 | 5/2005 | Walker |
| 6,893,446 B2 | 5/2005 | Sater |
| 6,905,057 B2 | 6/2005 | Swayze |
| 6,929,661 B2 | 8/2005 | Bolduc et al. |
| 6,942,674 B2 | 9/2005 | Belef |
| 6,945,979 B2 | 9/2005 | Kortenbach |
| 6,960,217 B2 | 11/2005 | Bolduc |
| 6,966,919 B2 | 11/2005 | Sixto, Jr. |
| 6,988,650 B2 | 1/2006 | Schwemberger |
| 7,000,819 B2 | 2/2006 | Swayze |
| 7,128,754 B2 | 10/2006 | Bolduc |
| 7,204,847 B1 | 4/2007 | Gambale |
| 7,261,716 B2 | 8/2007 | Strobel et al. |
| 7,357,287 B2 * | 4/2008 | Shelton, IV ...... A61B 17/07207 227/175.1 |
| 7,380,696 B2 * | 6/2008 | Shelton, IV ........ A61B 17/0686 227/175.1 |
| 7,404,508 B2 * | 7/2008 | Smith ................. A61B 17/068 227/175.1 |
| 7,637,905 B2 * | 12/2009 | Saadat ................ A61B 1/0055 600/104 |
| 7,670,362 B2 | 3/2010 | Zergiebel |
| 7,758,612 B2 | 7/2010 | Ship |
| 7,819,884 B2 * | 10/2010 | Lee .................... A61B 17/0469 600/114 |
| 7,862,573 B2 | 1/2011 | Darois |
| 7,867,252 B2 | 1/2011 | Criscuolo |

(56) References Cited

U.S. PATENT DOCUMENTS

| | | | |
|---|---|---|---|
| 7,913,892 B2* | 3/2011 | Cole | A61B 17/115 227/176.1 |
| 7,922,063 B2* | 4/2011 | Zemlok | A61B 17/07207 227/175.1 |
| 7,931,660 B2 | 4/2011 | Aranyi | |
| 8,002,811 B2 | 8/2011 | Corradi | |
| 8,034,076 B2 | 10/2011 | Criscuolo | |
| 8,075,570 B2 | 12/2011 | Bolduc et al. | |
| 8,087,142 B2 | 1/2012 | Levin | |
| 8,114,099 B2 | 2/2012 | Ship | |
| 8,114,101 B2 | 2/2012 | Criscuolo | |
| 8,181,840 B2* | 5/2012 | Milliman | A61B 17/115 227/175.1 |
| 8,216,272 B2 | 7/2012 | Ship | |
| 8,231,639 B2 | 7/2012 | Bolduc et al. | |
| 8,282,670 B2 | 10/2012 | Shipp | |
| 8,292,933 B2 | 10/2012 | Zergiebel | |
| 8,323,314 B2 | 12/2012 | Blier | |
| 8,328,823 B2 | 12/2012 | Aranyi | |
| 8,343,176 B2 | 1/2013 | Criscuolo | |
| 8,343,184 B2 | 1/2013 | Blier | |
| 8,382,778 B2 | 2/2013 | Criscuolo | |
| 8,414,627 B2 | 4/2013 | Corradi | |
| 8,465,520 B2 | 6/2013 | Blier | |
| 8,474,679 B2 | 7/2013 | Felix | |
| 8,579,919 B2 | 11/2013 | Bolduc | |
| 8,579,920 B2 | 11/2013 | Nering | |
| 8,597,311 B2 | 12/2013 | Criscuolo et al. | |
| 8,603,135 B2* | 12/2013 | Mueller | A61B 17/29 606/170 |
| 8,684,247 B2* | 4/2014 | Scirica | A61B 17/07207 227/175.1 |
| 8,728,120 B2 | 5/2014 | Blier | |
| 8,777,969 B2 | 7/2014 | Kayan | |
| 8,821,522 B2 | 9/2014 | Criscuolo et al. | |
| 8,821,557 B2 | 9/2014 | Corradi et al. | |
| 8,852,215 B2 | 10/2014 | Criscuolo et al. | |
| 9,186,138 B2* | 11/2015 | Corradi | A61B 17/064 |
| 2001/0044656 A1* | 11/2001 | Williamson, IV | A61F 2/2427 623/2.11 |
| 2003/0009441 A1 | 1/2003 | Holsten et al. | |
| 2003/0114839 A1 | 6/2003 | Looper et al. | |
| 2004/0092937 A1 | 5/2004 | Criscuolo | |
| 2004/0111089 A1 | 6/2004 | Stevens et al. | |
| 2004/0127916 A1 | 7/2004 | Bolduc et al. | |
| 2004/0181222 A1 | 9/2004 | Culbert et al. | |
| 2004/0243139 A1 | 12/2004 | Lewis et al. | |
| 2005/0222665 A1* | 10/2005 | Aranyi | A61B 17/068 623/1.11 |
| 2006/0047308 A1* | 3/2006 | Ortiz | A61B 17/07207 606/219 |
| 2006/0129152 A1 | 6/2006 | Ship | |
| 2007/0038220 A1 | 2/2007 | Ship | |
| 2007/0106317 A1* | 5/2007 | Shelton, IV | A61B 17/07207 606/170 |
| 2007/0162030 A1 | 7/2007 | Aranyi | |
| 2007/0282356 A1* | 12/2007 | Sonnenschein | A61B 17/068 606/153 |
| 2008/0029575 A1* | 2/2008 | Shelton | A61B 17/068 227/176.1 |
| 2008/0029576 A1* | 2/2008 | Shelton | A61B 17/07207 227/176.1 |
| 2008/0097523 A1 | 4/2008 | Bolduc | |
| 2008/0147113 A1 | 6/2008 | Nobis | |
| 2008/0169327 A1* | 7/2008 | Shelton | A61B 17/07207 227/176.1 |
| 2008/0188868 A1 | 8/2008 | Weitzner et al. | |
| 2008/0243106 A1 | 10/2008 | Coe et al. | |
| 2008/0243145 A1* | 10/2008 | Whitfield | A61B 17/1285 606/143 |
| 2008/0281336 A1 | 11/2008 | Zergiebel | |
| 2008/0312687 A1 | 12/2008 | Blier | |
| 2009/0118776 A1 | 5/2009 | Kelsch | |
| 2009/0188965 A1 | 7/2009 | Levin | |
| 2009/0289096 A1* | 11/2009 | Shelton, IV | A61B 17/07207 227/180.1 |
| 2009/0326546 A1* | 12/2009 | Mohamed | A61B 17/00234 606/114 |
| 2010/0030262 A1 | 2/2010 | McLean et al. | |
| 2010/0270354 A1 | 10/2010 | Rimer | |
| 2010/0292710 A1 | 11/2010 | Daniel | |
| 2010/0292713 A1 | 11/2010 | Cohn | |
| 2010/0292715 A1 | 11/2010 | Nering | |
| 2011/0022065 A1 | 1/2011 | Shipp | |
| 2011/0060349 A1 | 3/2011 | Cheng et al. | |
| 2011/0071578 A1 | 3/2011 | Colesanti | |
| 2011/0079627 A1 | 4/2011 | Cardinale | |
| 2011/0087240 A1 | 4/2011 | Shipp | |
| 2011/0295282 A1 | 12/2011 | Glick | |
| 2012/0059397 A1 | 3/2012 | Criscuolo et al. | |
| 2012/0109157 A1 | 5/2012 | Criscuolo et al. | |
| 2013/0018392 A1 | 1/2013 | Zergiebel | |
| 2013/0110088 A1 | 5/2013 | Wenchell | |
| 2013/0131700 A1 | 5/2013 | Criscuolo | |
| 2013/0197591 A1 | 8/2013 | Corradi | |
| 2014/0005678 A1* | 1/2014 | Shelton, IV | A61B 17/07207 606/130 |
| 2014/0014707 A1* | 1/2014 | Onukuri | A61B 17/068 227/177.1 |
| 2014/0114329 A1 | 4/2014 | Zergiebel | |
| 2014/0121684 A1 | 5/2014 | Criscuolo | |
| 2014/0276967 A1 | 9/2014 | Fischvogt et al. | |
| 2014/0276969 A1 | 9/2014 | Wenchell et al. | |
| 2014/0276972 A1 | 9/2014 | Abuzaina et al. | |
| 2014/0316446 A1 | 10/2014 | Kayan | |
| 2014/0371765 A1 | 12/2014 | Corradi et al. | |
| 2015/0001272 A1 | 1/2015 | Sniffin et al. | |
| 2015/0005748 A1 | 1/2015 | Sniffin et al. | |
| 2015/0005788 A1 | 1/2015 | Sniffin et al. | |
| 2015/0005789 A1 | 1/2015 | Sniffin et al. | |
| 2015/0018847 A1 | 1/2015 | Criscuolo et al. | |
| 2015/0032130 A1 | 1/2015 | Russo | |
| 2015/0080911 A1 | 3/2015 | Reed | |
| 2015/0133970 A1 | 5/2015 | Ranucci et al. | |
| 2015/0133971 A1 | 5/2015 | Ranucci et al. | |
| 2015/0133972 A1 | 5/2015 | Ranucci et al. | |

FOREIGN PATENT DOCUMENTS

| | | |
|---|---|---|
| EP | 0374088 | 6/1990 |
| EP | 0 834 280 A1 | 4/1998 |
| EP | 1 273 272 A2 | 1/2003 |
| EP | 1990013 A1 | 11/2008 |
| EP | 2 055 241 A2 | 5/2009 |
| EP | 1908409 B1 | 12/2010 |
| EP | 2399538 A2 | 12/2011 |
| EP | 2484294 A1 | 8/2012 |
| JP | 9 149 906 A | 6/1997 |
| WO | 00/16701 A1 | 3/2000 |
| WO | WO 02/34140 | 5/2002 |
| WO | WO 03/034925 | 5/2003 |
| WO | WO 03/103507 | 12/2003 |
| WO | WO 2004/112841 | 12/2004 |
| WO | 2005004727 A1 | 1/2005 |
| WO | WO 2009/039506 | 3/2009 |
| WO | 2012/064692 A2 | 5/2012 |
| WO | 2013/046115 A1 | 4/2013 |

OTHER PUBLICATIONS

Extended European Search Report corresponding to EP 14 15 9394.7, completed Apr. 16, 2014 and mailed Apr. 29, 2014; 8 pages.

European Search Report corresponding to EP No. 10 01 2659.8, completed Dec. 21, 2010; mailed Jan. 3, 2011: 3 pages.

European Search Report corresponding to EP No. 10 01 2646.5, completed Feb. 11, 2011; mailed Feb. 22, 2011; 3 pages.

EP Search Report corresponding to EP 14 18 1900.3, completed Mar. 31, 2015 and dated Apr. 9, 2015; 7pp.

Extended European Search Report corresponding to EP 14 15 8946.5, completed Jun. 20, 2014 and mailed Jul. 8, 2014; (9 pp).

(56) References Cited

OTHER PUBLICATIONS

Extended European Search Report corresponding to EP 14 17 8107.0, completed Nov. 24, 2014 and mailed Dec. 3, 2014; (5 pp).
Extended European Search Report corresponding to EP 14 17 4656.0, completed Jan. 16, 2015 and mailed Jan. 26, 2015; (7 pp).
Extended European Search Report corresponding to EP 14 18 4907.5, completed Jan. 12, 2015 and mailed Jan. 27, 2015; (9 pp).
Extended European Search Report corresponding to counterpart application EP 14 19 7885.8 dated Apr. 30, 2015; 9pp.

* cited by examiner

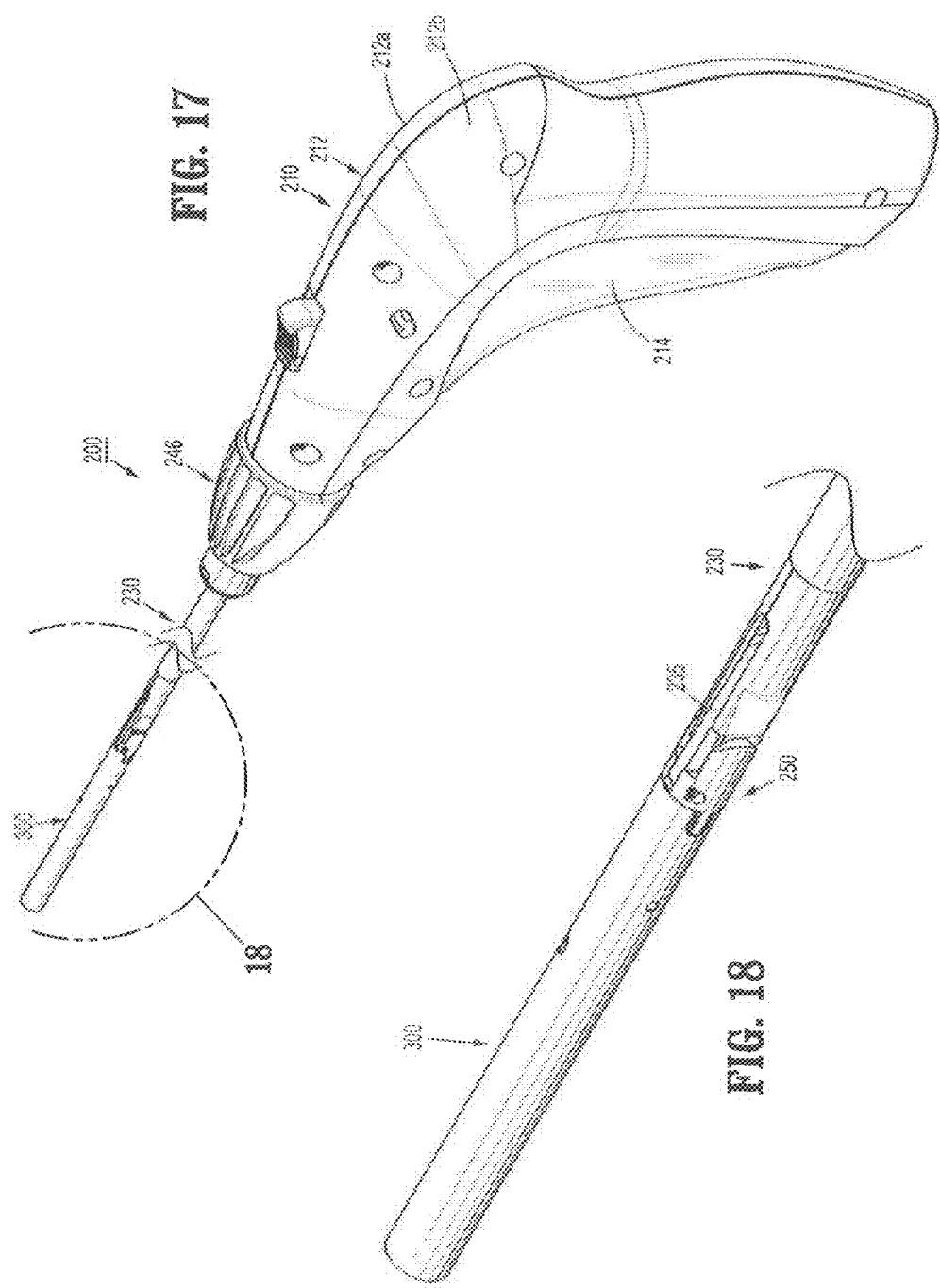

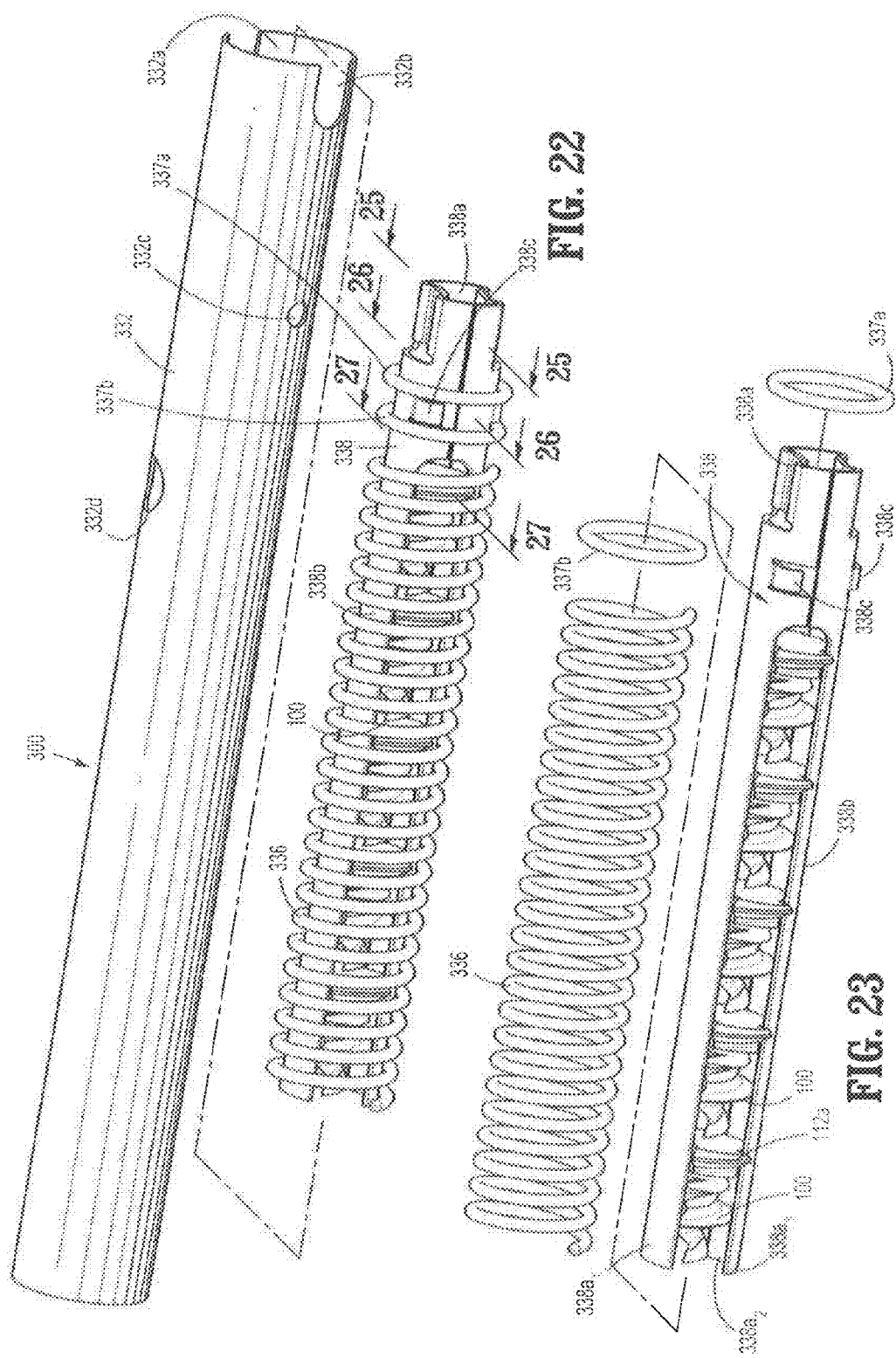

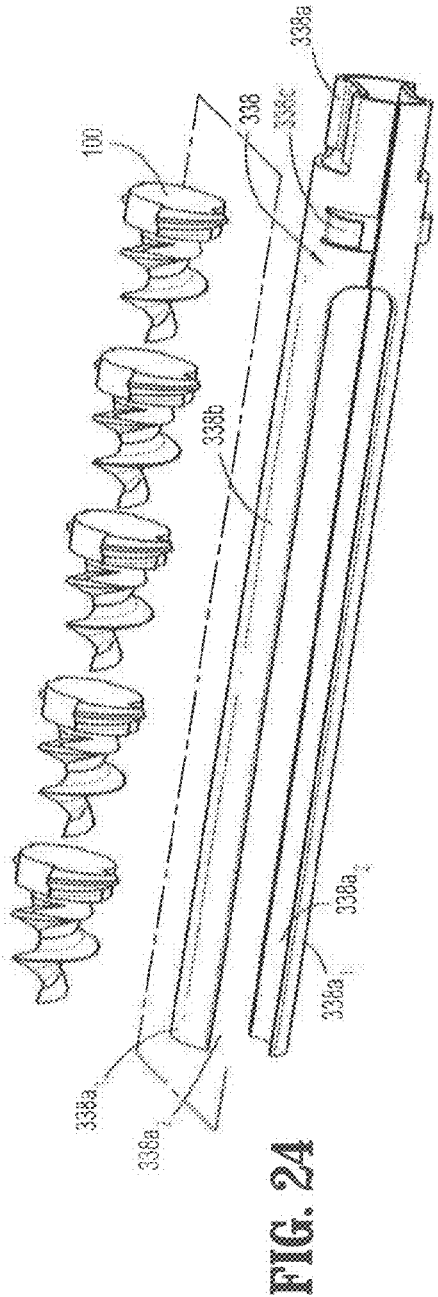
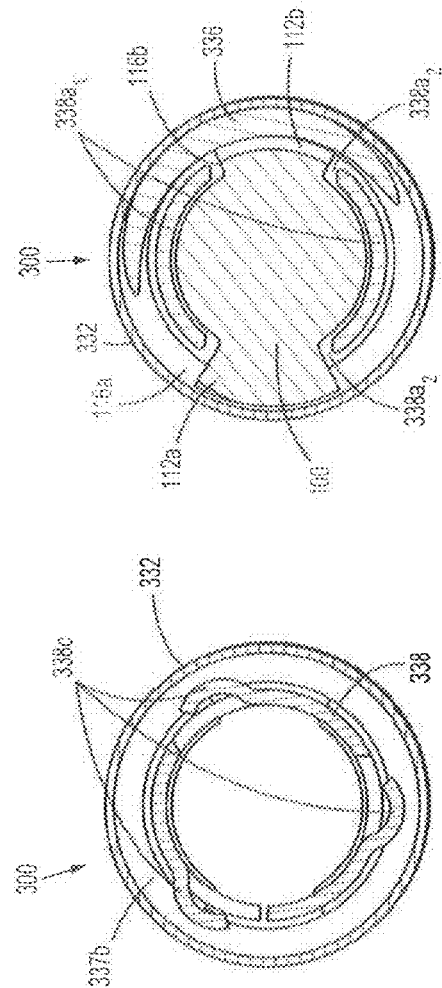
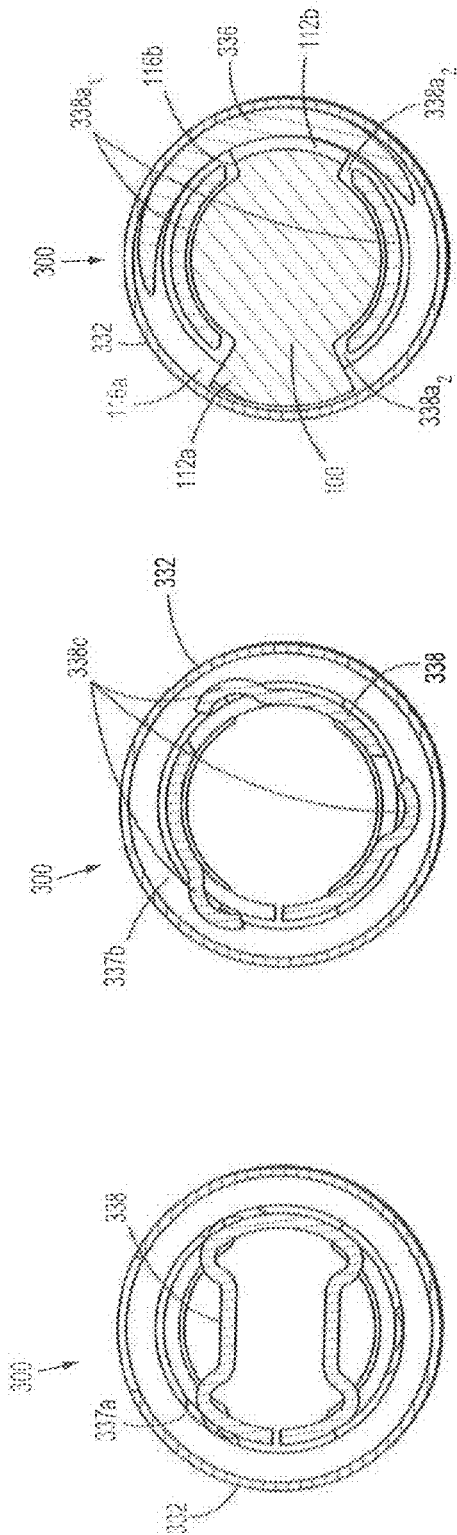
FIG. 24
FIG. 25
FIG. 26
FIG. 27

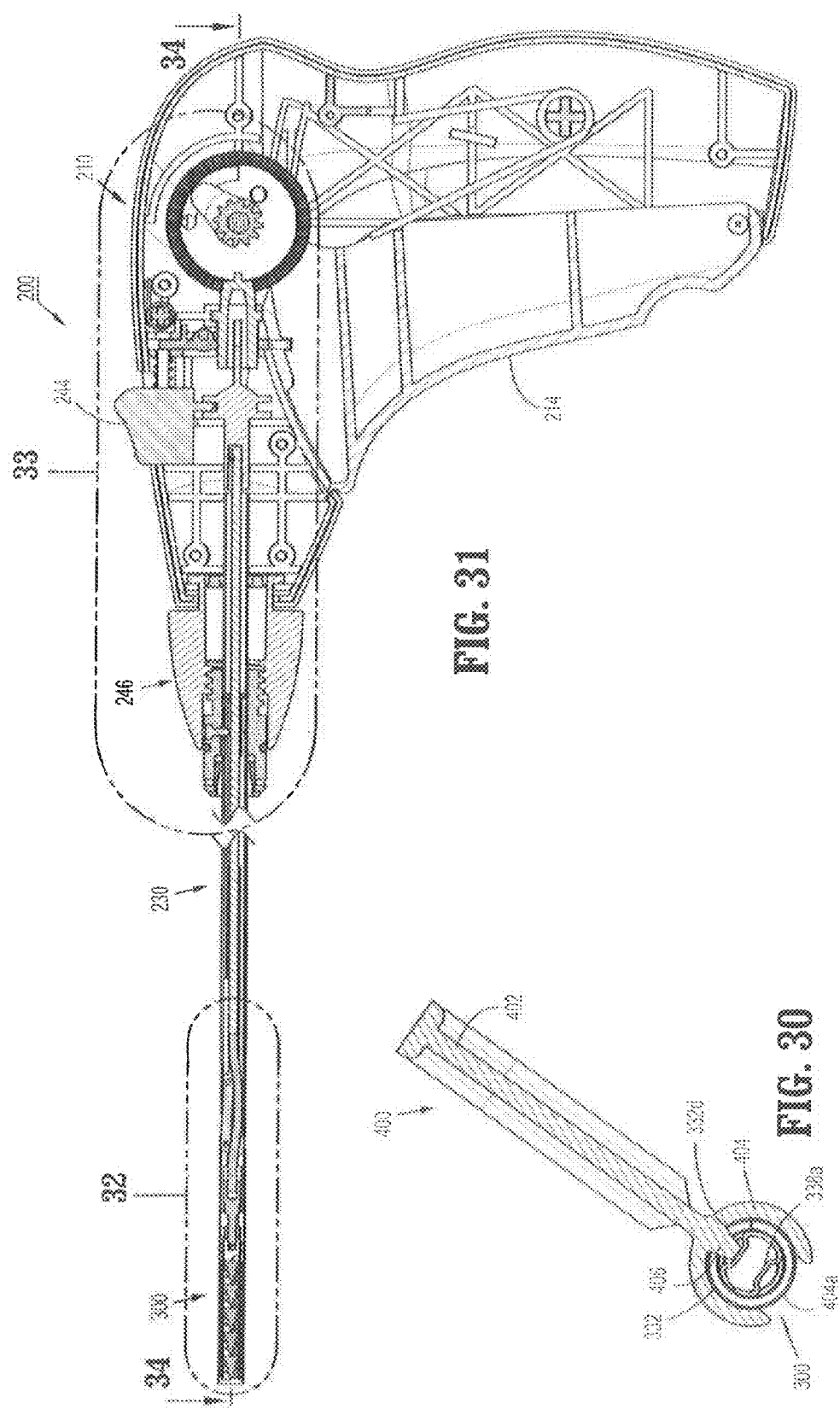

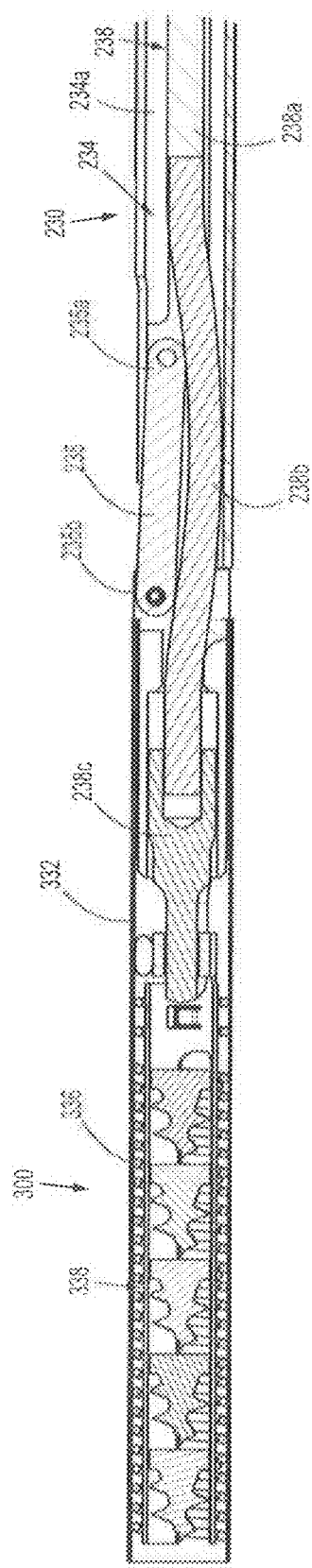

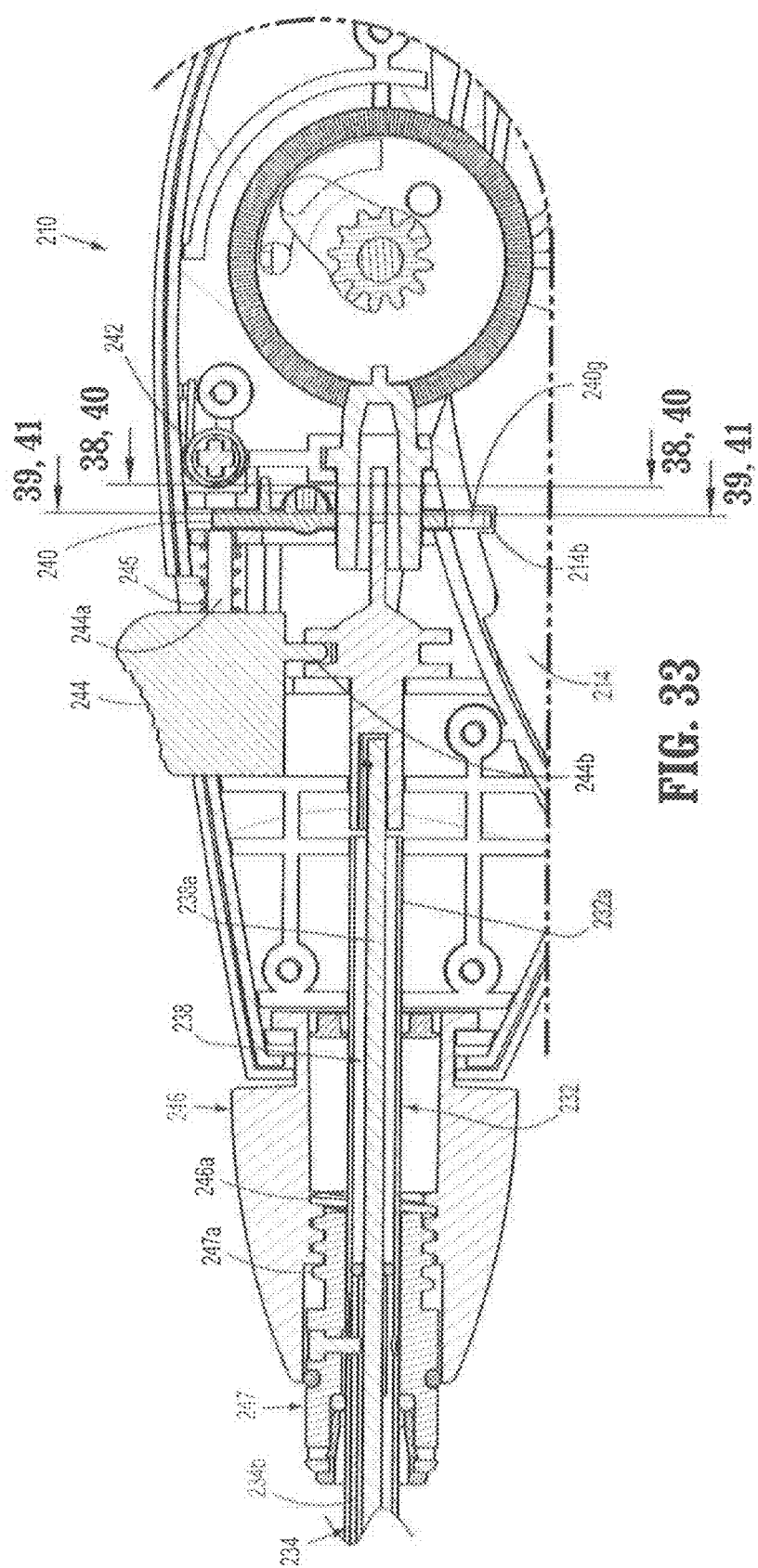

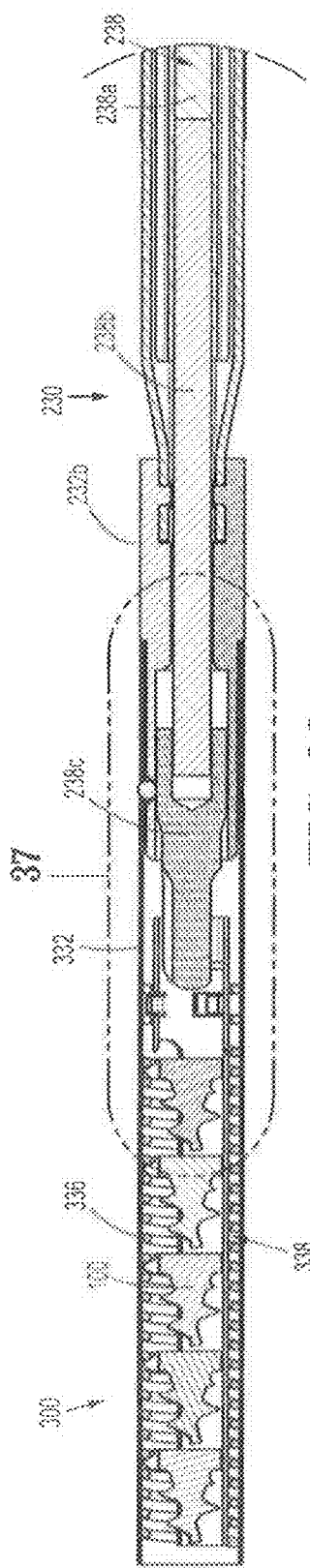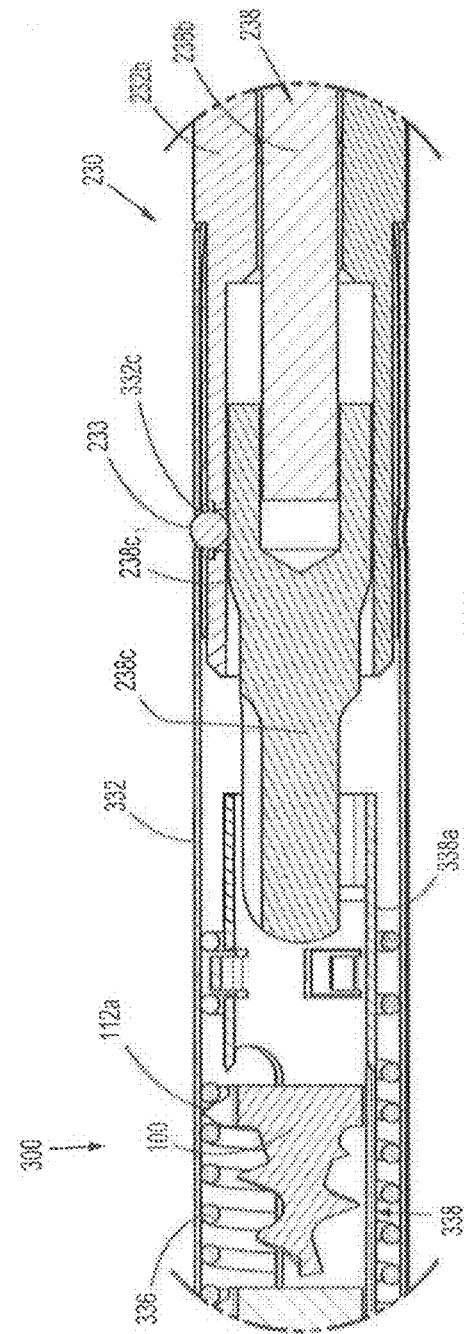

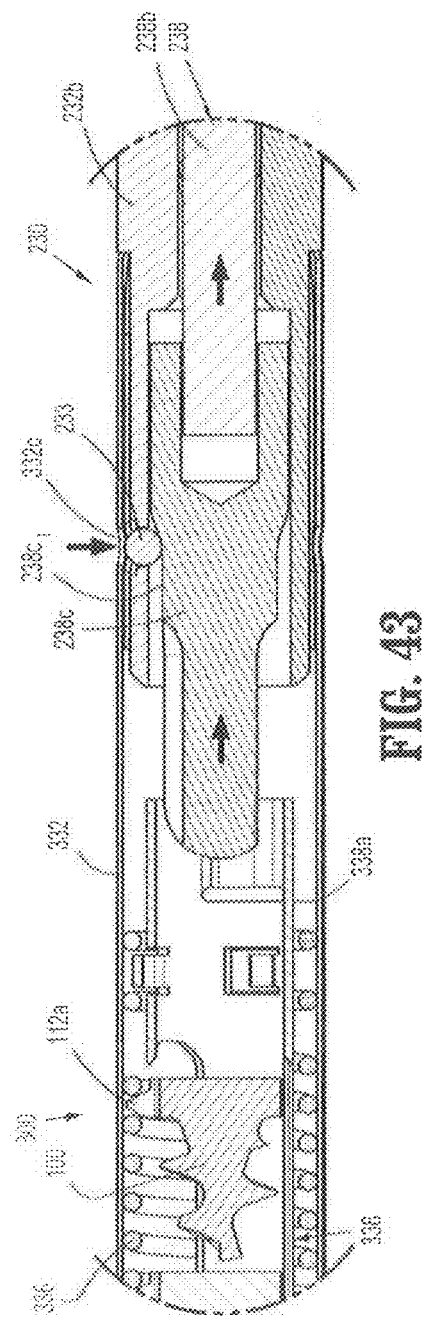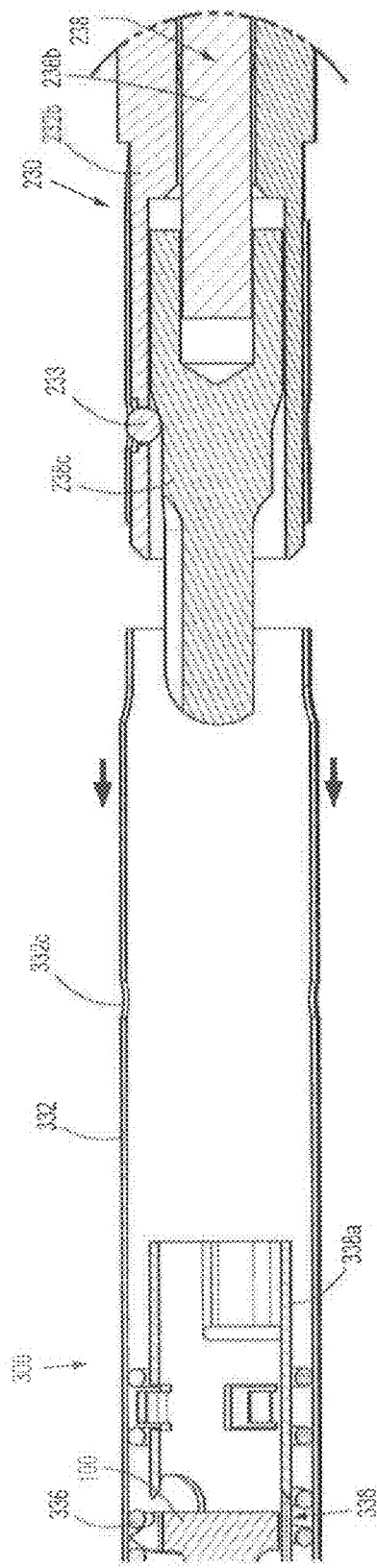

ARTICULATING APPARATUS FOR ENDOSCOPIC PROCEDURES

CROSS REFERENCE TO RELATED APPLICATIONS

This application is a continuation-in-part application claiming the benefit of and priority to U.S. patent application Ser. No. 13/930,770, filed Jun. 28, 2013, the entire contents of which are incorporated herein by reference.

TECHNICAL FIELD

The present disclosure relates to surgical apparatus, devices and/or systems for performing endoscopic surgical procedures and methods of use thereof. More specifically, the present disclosure relates to surgical apparatus, devices and/or systems for performing endoscopic surgical procedures which includes an articulating endoscopic portion.

BACKGROUND

During laparoscopic or endoscopic surgical procedures, access to a surgical site is achieved through a small incision or through a narrow cannula inserted through a small entrance wound in a patient. Because of limited area to access the surgical site, many endoscopic surgical devices include mechanisms for articulating the tool assembly of the device. Typically, the articulating mechanism is controlled by an actuator which has to be manipulated by a surgeon to properly orient the tool assembly in relation to tissue to be treated.

Accordingly, a need exists for endoscopic surgical devices which include features which indicate to the surgeon whether the endoscopic portion of the surgical device, when in the surgical site, is in a non-articulated or articulated orientation.

SUMMARY

The present disclosure relates to surgical apparatus, devices and/or systems for performing endoscopic surgical procedures which includes an articulating endoscopic portion.

According to an aspect of the present disclosure, an endoscopic surgical device is provided. The surgical device includes a handle assembly including a handle housing and a trigger operatively connected to the handle housing, and a drive mechanism actuatable by the trigger; and an endoscopic assembly including a proximal end portion extending from the handle assembly; a distal end portion pivotably connected to the proximal end portion of the endoscopic assembly at a pivot point; and a rotatable inner actuation shaft extending from the handle assembly and into the distal end portion of the endoscopic assembly, the inner actuation shaft including a flexible portion extending across the pivot point, the inner actuation shaft being connected to the drive mechanism of the handle assembly such that an actuation of the trigger results in a rotation of the inner actuation shaft.

The surgical device further includes an end effector selectively connectable to the distal end portion of the endoscopic assembly and to a distal portion of the rotatable inner actuation shaft. The end effector includes an outer tube having a helical thread along an inner surface thereof; a splined inner tube rotatably supported in the outer tube, wherein the splined inner tube is defined by a pair of opposed longitudinally extending tines and a pair of opposed longitudinally extending channels, a proximal end of the splined inner tube being configured for non-rotatable selective connection to a distal end of the rotatable inner actuation shaft when the end effector is connected to the distal end portion of the endoscopic assembly; and a plurality of surgical anchors loaded in the inner tube of the end effector, wherein each anchor includes a threaded body portion, and a head portion defining a pair of opposed radially outer threads and a pair of opposed radial recesses, wherein the pair of radial recess of each head portion receive respective tines of the inner tube and wherein the pair of opposed radially outer threads of each head portion project from the pair of opposed longitudinally extending channels of the inner tube and engage the inner helical thread of the outer tube.

The endoscopic assembly may include a support tube assembly having a proximal support tube portion extending from the handle assembly, and a distal support tube portion pivotally connected to proximal support tube portion thereby defining an articulation joint therebetween.

The endoscopic assembly may include an articulation tube slidably supported in the support tube assembly, a proximal end of the articulation tube being connected to an articulation actuator supported on the handle assembly, and a distal end of the articulation tube being pivotably connected to an articulation link that is also pivotably connected to the distal support tube portion of the support tube assembly.

The inner actuation shaft may be is rotatably supported in the articulation tube. The inner actuation shaft may include a proximal shaft portion operatively connected to the drive mechanism, a distal shaft portion non-rotatably connected to a distal end of the proximal shaft portion, and a coupling member non-rotatably connected to a distal end of the distal shaft portion.

The distal shaft portion of the inner actuation shaft may be the flexible portion.

The flexible portion of the inner actuation shaft may be relatively more flexible than the proximal shaft portion of the inner actuation shaft.

In use, an actuation of the trigger may result in a rotation of the inner actuation shaft of the endoscopic assembly.

The drive mechanism may transmit the actuation of the trigger into rotation of the inner actuation shaft of the endoscopic assembly.

The endoscopic assembly may include an inner articulation tube assembly having the articulation tube defining a proximal end and a distal end, the proximal end of the articulation tube being operatively connected to the articulation actuator. The articulation link may have a proximal end pivotally connected to the distal end of the articulation tube.

The handle assembly may include an articulation knob rotatably supported thereon. The articulation knob may be the articulation actuator. The articulation knob may define an inner helical thread, the proximal end of the articulation tube may be operatively connected to the articulation tube such that rotation of the articulation knob causes the articulation tube to axially translate.

In use, axial translation of the articulation tube may cause the distal support tube portion of the support tube assembly to pivot about the pivot point.

The endoscopic assembly may include a connection nut fixedly secured to the proximal end of the articulation tube. The connection nut may define an outer helical thread and may meshingly engage the inner helical thread of the articulation knob.

The endoscopic assembly may support a ball detent in the distal support tube portion of the support tube assembly. The ball detent may have a projected position wherein the ball detent partially projects radially outward from the distal support tube portion of the support tube assembly. The ball detent may have a retracted position wherein the ball detent does not project radially outward from the distal support tube portion of the support tube assembly as far as when in the projected position.

The ball detent may ride along an outer surface of the coupling member of the inner actuation shaft of the endoscopic assembly.

The inner actuation shaft may be axially translatable between a proximal position wherein the ball detent is in the retracted position and a distal position wherein the coupling member of the inner actuation shaft holds the ball detent in the projected position.

In use, when the end effector is connected to the distal end portion of the endoscopic assembly, and when the ball detent is in the projected position, the ball detent may engage a recess in the end effector to secure the end effector to the distal end portion of the endoscopic assembly.

The inner actuation shaft may be axially translatable within the articulation tube.

A proximal end of the proximal shaft portion of the inner actuation shaft may support a pair of axially spaced apart radial flanges.

The handle assembly may include a slider supported thereon. A stem of the slider may extend between the pair of axially spaced apart radial flanges supported on the inner actuation shaft.

The slider may be movable between a proximal position and a distal position. In use, movement of the slider between the proximal position and the distal position may result in movement of the inner actuation shaft between a respective proximal position and a distal position.

The slider may be in the proximal position, the end effector is connectable to the to the distal end portion of the endoscopic assembly. In use, when the slider is in the distal position, the end effector may be secured to the to the distal end portion of the endoscopic assembly.

The endoscopic assembly may support a ball detent in the distal support tube portion of the support tube assembly. The ball detent may have a projected position wherein the ball detent partially projects radially outward from the distal support tube portion of the support tube assembly. The ball detent may have a retracted position wherein the ball detent does not project radially outward from the distal support tube portion of the support tube assembly as far as when in the projected position.

The ball detent may ride along an outer surface of the coupling member of the inner actuation shaft of the endoscopic assembly.

The ball detent may be in the retracted position when the inner actuation shaft is in the proximal position. The ball detent may be in the projected position when the inner actuation shaft is in the distal position.

In use, when the end effector is connected to the distal end portion of the endoscopic assembly, and when the ball detent is in the projected position, the ball detent may engage a recess in the end effector to secure the end effector to the distal end portion of the endoscopic assembly.

The handle assembly may include a button supported thereon. The button may include a first position wherein the button blocks movement of the slider, and a second position wherein the button permits movement of the slider.

The button may include a wall extending therefrom. In use, when the button is in the first position, the trigger may be actuatable and the slider may be blocked from moving to the proximal position; and when the button is in the second position, the wall of the button may block the actuation of the trigger and the slider may be free to move to the proximal position.

The handle assembly may include a biasing member tending to maintain the button in one of the first portion and the second position thereon.

The button may include a wall extending therefrom. In use, when the button is in the first position, the trigger is actuatable; and when the button is in the second position, the wall of the button blocks actuation of the trigger.

The distal end portion of the endoscopic assembly may be pivotable when the button is in the second position.

The coupling member of the inner actuation shaft may have a non-circular transverse cross-sectional profile, and wherein the proximal end of the splined inner tube of the end effector may have a splined inner tube rotatably supported in the outer tube. The splined inner tube may be defined by a pair of opposed longitudinally extending tines and a pair of opposed longitudinally extending channels. A proximal end of the splined inner tube may have a transverse cross-sectional profile that complements the non-circular transverse cross-sectional profile of the coupling member.

The handle assembly may include an audible/tactile feedback system associated with the trigger. The audible/tactile feedback system may produce at least one of an audible feedback and a tactile feedback when the trigger is in one of a locked out position for loading and unloading an end effector to the endoscopic assembly, when the trigger has been fully actuated, and when the trigger returns to a home position.

The distal end portion of the endoscopic assembly may be articulatable between a non-articulated orientation and a plurality of articulated orientations relative to the proximal end portion thereof.

According to another aspect of the present disclosure, an end effector for selective connection to a rotatable drive shaft of a surgical handle assembly is provided. The end effector includes an outer tube having a helical thread along an inner surface thereof; a splined inner tube rotatably supported in the outer tube, wherein the splined inner tube is defined by a pair of opposed longitudinally extending tines and a pair of opposed longitudinally extending channels, a proximal end of the splined inner tube being configured for non-rotatable selective connection to a distal end of the rotatable drive shaft of the surgical handle assembly when the end effector is connected thereto; and a plurality of surgical anchors loaded in the inner tube.

Each anchor includes a threaded body portion; and a head portion defining a pair of opposed radially outer threads and a pair of opposed radial recesses, wherein the pair of radial recess of each head portion receive respective tines of the inner tube and wherein the pair of opposed radially outer threads of each head portion project from the pair of opposed longitudinally extending channels of the inner tube and engage the inner helical thread of the outer tube.

The proximal end of the inner tube may have a non-circular transverse cross-sectional profile.

The helical thread of the outer tube may be defined by a helical coil.

The inner tube may be fixed against longitudinal displacement relative to the outer tube.

Each surgical anchor may be formed from a bioabsorbable material.

According to still a further aspect of the present disclosure, an endoscopic surgical device configured to fire a surgical anchor into target tissue is provided. The surgical device includes a handle assembly including a handle housing; a trigger operatively connected to the handle housing, the trigger including at least a fully un-actuated position; a drive mechanism actuatable by the trigger; and a timing system associating the trigger with the drive mechanism.

The surgical device further includes an endoscopic assembly including a proximal end portion extending from the handle assembly; a distal end portion configured to support an end effector; and a rotatable inner actuation shaft extending from the handle assembly and into the distal end portion of the endoscopic assembly, the inner actuation shaft being connected to the drive mechanism of the handle assembly such that an actuation of the trigger results in a rotation of the inner actuation shaft to fire a surgical anchor of the surgical device.

In use, the timing system maintains a timing of an actuation stroke of the trigger with an actuation of the drive mechanism to fire a single surgical anchor upon a single stroke of the trigger from the fully un-actuated position, to a fully actuated position, to the fully un-actuated position.

The timing system may include a raceway formed in a surface of the trigger, the raceway defining a plurality of steps along a length thereof; and a deflectable arm having a first end disposed within the raceway and operatively associated with the steps thereof, and a second end connected to the handle housing.

The distal end of the deflectable arm may ride through the raceway when the trigger is actuated. The distal end of the deflectable arm may ride through the raceway in a single direction during a complete stroke of the trigger.

The steps of the raceway may block movement of the distal end of the deflectable arm, in a reverse direction, through the raceway, when the trigger is partially actuated.

The raceway may define a home position for the distal end of the deflectable arm when the trigger is in the fully un-actuated position.

The handle assembly may include a button supported thereon. The button may include a first position wherein the button permits actuation of the trigger, and wherein the bottom may include a second position wherein the button blocks actuation of the trigger.

The button may include a wall extending therefrom. In use, when the button is in the second position the wall of the button may block actuation of the trigger.

The trigger may define a notch formed therein. In use, the wall of the button may enter the notch of the trigger when the trigger is in the fully un-actuated position and when the button is in the second position.

The timing system may include a raceway formed in a surface of the trigger, the raceway defining a plurality of steps along a length thereof; and a deflectable arm having a first end disposed within the raceway and operatively associated with the steps thereof, and a second end connected to the handle housing.

The distal end of the deflectable arm may ride through the raceway when the trigger is actuated.

The distal end of the deflectable arm may ride through the raceway in a single direction during a complete stroke of the trigger.

The steps of the raceway may block movement of the distal end of the deflectable arm, in a reverse direction, through the raceway, when the trigger is partially actuated and then un-actuated.

The raceway may define a home position for the distal end of the deflectable arm when the trigger is in the fully un-actuated position.

The endoscopic assembly may include a support tube assembly having a proximal support tube portion extending from the handle assembly, and a distal support tube portion configured to removably receive the end effector. The inner actuation shaft may be rotatably supported in the support tube, the inner actuation shaft including a proximal portion operatively connected to the drive mechanism, and a distal portion non-rotatably supporting a coupling member.

In use, an actuation of the trigger may result in an actuation of the drive mechanism to rotate the inner actuation shaft of the endoscopic assembly.

The endoscopic assembly may support a ball detent in the distal support tube portion of the support tube assembly. The ball detent may have a projected position wherein the ball detent partially projects radially outward from the distal support tube portion of the support tube assembly. The ball detent may have a retracted position wherein the ball detent does not project radially outward from the distal support tube portion of the support tube assembly as far as when in the projected position.

The ball detent may ride along an outer surface of the coupling member of the inner actuation shaft of the endoscopic assembly.

The inner actuation shaft may be axially translatable between a proximal position wherein the ball detent is in the retracted position and a distal position wherein the coupling member of the inner actuation shaft holds the ball detent in the projected position.

In use, the inner actuation shaft may be axially translatable only when the trigger is in the fully un-actuated position.

In use, when the end effector is connected to the distal end portion of the endoscopic assembly, and when the ball detent is in the projected position, the ball detent may engage a recess in the end effector to secure the end effector to the distal end portion of the endoscopic assembly.

According to yet another aspect of the present disclosure, an endoscopic surgical device includes an elongate body portion and an end effector releasably supported adjacent a distal end of the elongate body portion.

The elongate body portion includes an outer tube and an inner actuation shaft. The inner actuation shaft is movably positioned within the outer tube and repositionable between a retracted position and an advanced position. The inner actuation shaft includes an engagement member that is concealed within the outer tube in the retracted position and exposed from the outer tube in the advanced position.

The elongate body portion may include a proximal portion and a distal portion, the distal portion pivotably connected to the proximal portion at a pivot point.

The end effector includes an engagement member and a plurality of surgical anchors. The engagement member of the end effector corresponds to the engagement member of the inner actuation shaft to facilitate releasable connection of the end effector to the elongate body portion.

In use, the end effector is releasable from the elongate body portion when the inner actuation shaft is positioned in the advanced position and secured to the elongate body portion when the inner actuation shaft is positioned in the refracted position.

The engagement structure of the inner actuation shaft may be located at a distal end of the actuation shaft, and the engagement member of the end effector may be located at a proximal end of the end effector.

The engagement member of the inner actuation shaft may include a recess and the engagement member of the end effector may include a protrusion configured and dimensioned for positioning within the recess.

In use, the inner actuation shaft is rotatable within outer tube and rotation of the inner actuation shaft is transmitted to the end effector via connection of the corresponding engagement members of the inner actuation shaft and the end effector.

The end effector may include an outer tube and an inner tube, the inner tube positioned within the outer tube. The inner tube of the end effector may include a pair of opposed longitudinally extending tines and may define a pair of opposed longitudinally extending channels.

In use, the inner tube of the end effector may be rotatably supported within the outer tube.

Each anchor may include a threaded body portion and a head portion. The head portion may define a pair of opposed radially outer threads and a pair of opposed radial recesses. The pair of radial recesses of each head portion may receive the pair of tines of the inner tube of the end effector. The outer tube of the end effector may include a helical thread along an inner surface thereof. The outer threads of the head portion of each anchor may project from the longitudinally extending channels defined by the inner tube of the end effector, and may engage the helical thread of the outer tube of the end effector.

The endoscopic surgical device may include a handle assembly supported adjacent a proximal end of the elongate body portion. The handle assembly may include a handle housing, a trigger operatively connected to the handle housing, and a drive mechanism actuatable by the trigger.

In use, the drive mechanism is connected to the inner actuation shaft such that actuation of the trigger results in rotation of the inner actuation shaft.

According to still another aspect of the present disclosure, a method of performing a surgical procedure with an endoscopic surgical device is provided. The method includes advancing an inner actuation shaft of the surgical device distally to expose a first engagement member formed on the inner actuation shaft from an outer tube of an elongate body portion, securing an end effector to the inner actuation shaft by connecting the first engagement member to a second engagement member formed on a proximal end of the end effector, retracting the inner actuation shaft such that the first and second engagement members are concealed within the outer tube of the elongate body portion, inserting the end effector into an opening in tissue, and performing a surgical task with the end effector.

Securing the end effector to the inner actuation shaft may include inserting a pin that extends from the second engagement member within a recess defined by the first engagement member.

Advancing the inner actuation shaft may include moving a slide member supported on a handle assembly of the surgical device in a distal direction.

Retracting the inner actuation shaft may include moving the slide member supported on the handle assembly of the surgical device in a proximal direction.

The method may involve articulating the end effector about a pivot point via rotation of an articulation knob rotatably supported on a handle assembly of the surgical device.

Performing the surgical task may include deploying a surgical anchor from the end effector, and securing the surgical anchor to tissue.

According to one aspect of the present disclosure, a shipping wedge for an end effector of an endoscopic surgical device is provided. The shipping wedge includes an elongate body and an angled body that extends from the elongate body at an acute angle relative to the elongate body. The elongate body is configured and dimensioned to receive an elongate body portion of an endoscopic surgical device and includes a first pair of opposed sidewalls that define a first channel. The first channel extends longitudinally through the elongate body. The angled body includes a second pair of opposed sidewalls that define a second channel configured and dimensioned to support an end effector for connection to the elongate body portion of the endoscopic surgical device.

At least one of the first and second channels may be U-shaped.

The shipping wedge may include an alignment rib that extends from the first pair of sidewalls of elongate body. The alignment rib may be positioned adjacent to the angled body. The alignment rib may define a passage that extends through the alignment rib.

The angled body may include a protuberance that extends from an inner surface of the angled body.

The shipping wedge may include alignment flanges that extend from at least one of the first and second pairs of sidewalls.

In use, the angled body may prevent the end effector from moving when the end effector is supported within the second channel and positioned in axial alignment with the channel.

In use, the first channel may enable the end effector to move through the first channel when the end effector is positioned in axial alignment with the first channel.

According to yet another aspect of the present disclosure, a method of removing an end effector for use with an endoscopic surgical device from a shipping wedge is provided. The method involves securing an end effector to a shipping wedge, positioning an elongate body portion of the endoscopic surgical device within the shipping wedge, advancing the elongate body portion into engagement with the end effector, pivoting the end effector within the shipping wedge relative to the elongate body portion, securing the end effector to the elongate body portion, and removing the end effector and the elongate body portion from the shipping wedge.

The method may include aligning a distal end of the elongate body portion with a proximal end of the end effector. Aligning the elongate body portion may include abutting the elongate body portion into engagement with an alignment rib that extends from the shipping wedge.

Removing the end effector and the elongate body portion may include passing the end effector beneath the alignment rib.

Securing the end effector to the shipping wedge may include securing the end effector to a protuberance that extends from the shipping wedge to prevent the end effector from rotating.

Securing the end effector to the elongate body portion may include drawing the end effector into engagement with the elongate body portion.

Further details and aspects of exemplary embodiments of the present invention are described in more detail below with reference to the appended figures.

BRIEF DESCRIPTION OF THE DRAWINGS

Embodiments of the present disclosure are described herein with reference to the accompanying drawings, wherein:

FIG. 17 is a rear perspective view of the endoscopic surgical device of FIG. 5;

FIG. 18 is an enlarged view of the indicated area of detail of FIG. 17;

FIG. 22 is a perspective view of the end effector of FIGS. 20 and 21, with an outer tube separated therefrom;

FIG. 23 is a perspective view of the end effector of FIGS. 20-22, with an outer tube removed therefrom and with parts partially separated;

FIG. 24 is a perspective view of an inner tube of the end effector of FIGS. 20-23, with a plurality of anchors of FIGS. 1-4 shown separated therefrom;

FIG. 25 is a cross-sectional view, as taken along 25-25 of FIG. 22;

FIG. 26 is a cross-sectional view, as taken along 26-26 of FIG. 22;

FIG. 27 is a cross-sectional view, as taken along 27-27 of FIG. 22;

FIG. 30 is a cross-sectional view as taken through 30-30 of FIG. 29;

FIG. 31 is a longitudinal, cross-sectional, elevational view of the endoscopic surgical device of FIG. 5;

FIG. 32 is an enlarged view of the indicated area of detail of FIG. 31;

FIG. 33 is an enlarged view of the indicated area of detail of FIG. 31;

FIG. 36 is an enlarged view of the indicated area of detail of FIG. 34;

FIG. 37 is an enlarged view of the indicated area of detail of FIG. 36;

FIG. 43 is a longitudinal, cross-sectional view the end effector and the endoscopic assembly of the endoscopic surgical device of FIG. 5, illustrating a first step in the decoupling thereof;

FIG. 44 is a longitudinal, cross-sectional view the end effector and the endoscopic assembly of the endoscopic surgical device of FIG. 5, illustrating a second step in the decoupling thereof;

DETAILED DESCRIPTION OF EMBODIMENTS

Figure 1:
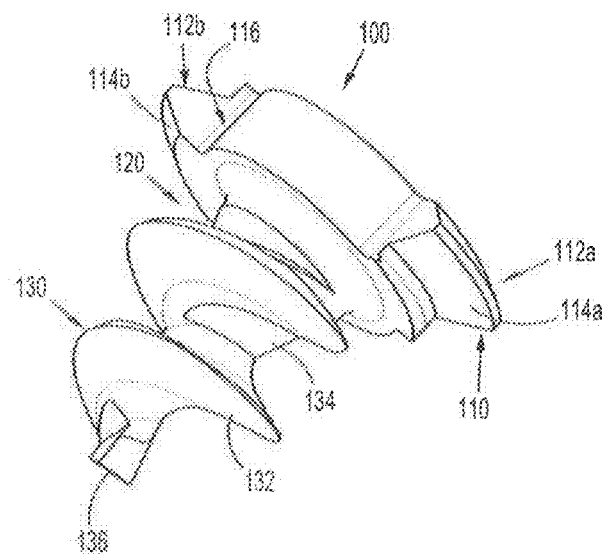
FIG. 1 is a perspective view of a surgical anchor for use in an endoscopic surgical device in accordance with the present disclosure.
Figure 2:
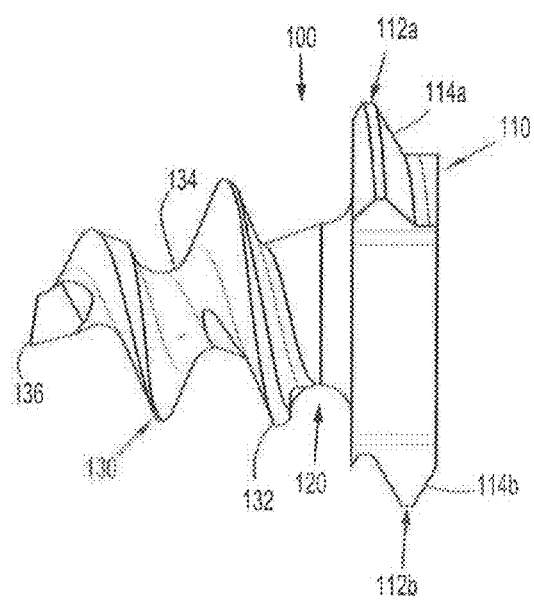
FIG. 2 is a side, elevational view of the surgical anchor of FIG. 1.
Figure 3:
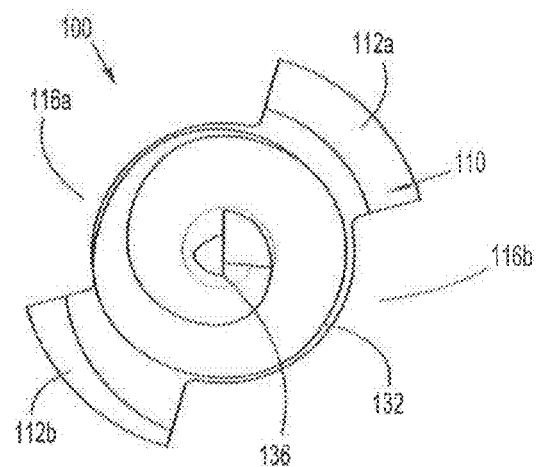
FIG. 3 is a distal, end view of the surgical anchor of FIGS. 1 and 2.

Embodiments of the presently disclosed endoscopic surgical device is described in detail with reference to the drawings, in which like reference numerals designate identical or corresponding elements in each of the several views. As used herein the term "distal" refers to that portion of the endoscopic surgical device that is farther from the user, while the term "proximal" refers to that portion of the endoscopic surgical device that is closer to the user.

Non-limiting examples of endoscopic surgical devices which may include articulation joints according to the present disclosure include manual, mechanical and/or electromechanical surgical tack appliers (i.e., tackers) and the like.

Referring initially to FIGS. 1-4, a surgical anchor for use with the surgical tack applier of the present disclosure is illustrated and generally designated as anchor 100. As seen in FIGS. 1-4, anchor 100 includes a head section 110, a mesh retention section 120, and a threaded tissue-snaring section 130. Head section 110 includes a pair of opposing threaded sections 112a, 112b having respective radially, outer, helical head threads 114a, 114b, and a pair of opposing open sections, slotted sections or radial recesses 116a, 116b. A distal surface of head section 110 is formed onto or integral with a proximal end of mesh retention section 120.

Mesh retention section 120 of anchor 100 extends from and between a distal end or surface of head section 110 and a proximal end of tissue-snaring section 130. Mesh retention section 120 functions to lock, anchor or otherwise retain a surgical mesh (not shown) on to anchor 100 when anchor 100 is screwed into the mesh to a depth past a proximal-most segment 138 of tissue-snaring thread 132 of tissue-snaring section 130. This is achieved because there is no thread located in mesh retention section 120 that would allow anchor 100 to be unscrewed or backed out from the mesh.

Mesh retention section 120 has a cylindrical or conical transverse cross-sectional profile. Mesh retention section 120 includes a transverse radial dimension, relative to a central longitudinal axis of anchor 100, that is smaller than a transverse radial dimension of head section 110, and smaller than a transverse radial dimension of proximal-most segment 138 of tissue-snaring thread 138.

Threaded tissue-snaring section 130 of anchor 100 includes helical threads 132 formed onto a tapered truncated body section 134. A distal point or tip 136 defines the terminus of the distal most tissue-snaring thread 132.

Figure 4:
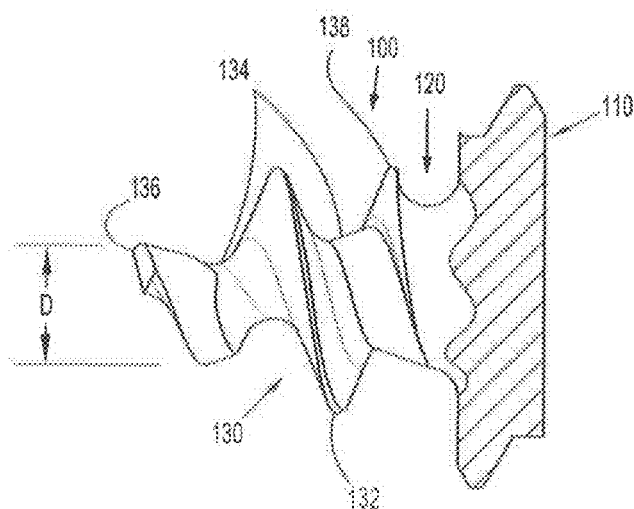
FIG. 4 is a side, elevational view, partially broken away, of the surgical anchor of FIGS. 1-3.
Figure 5:
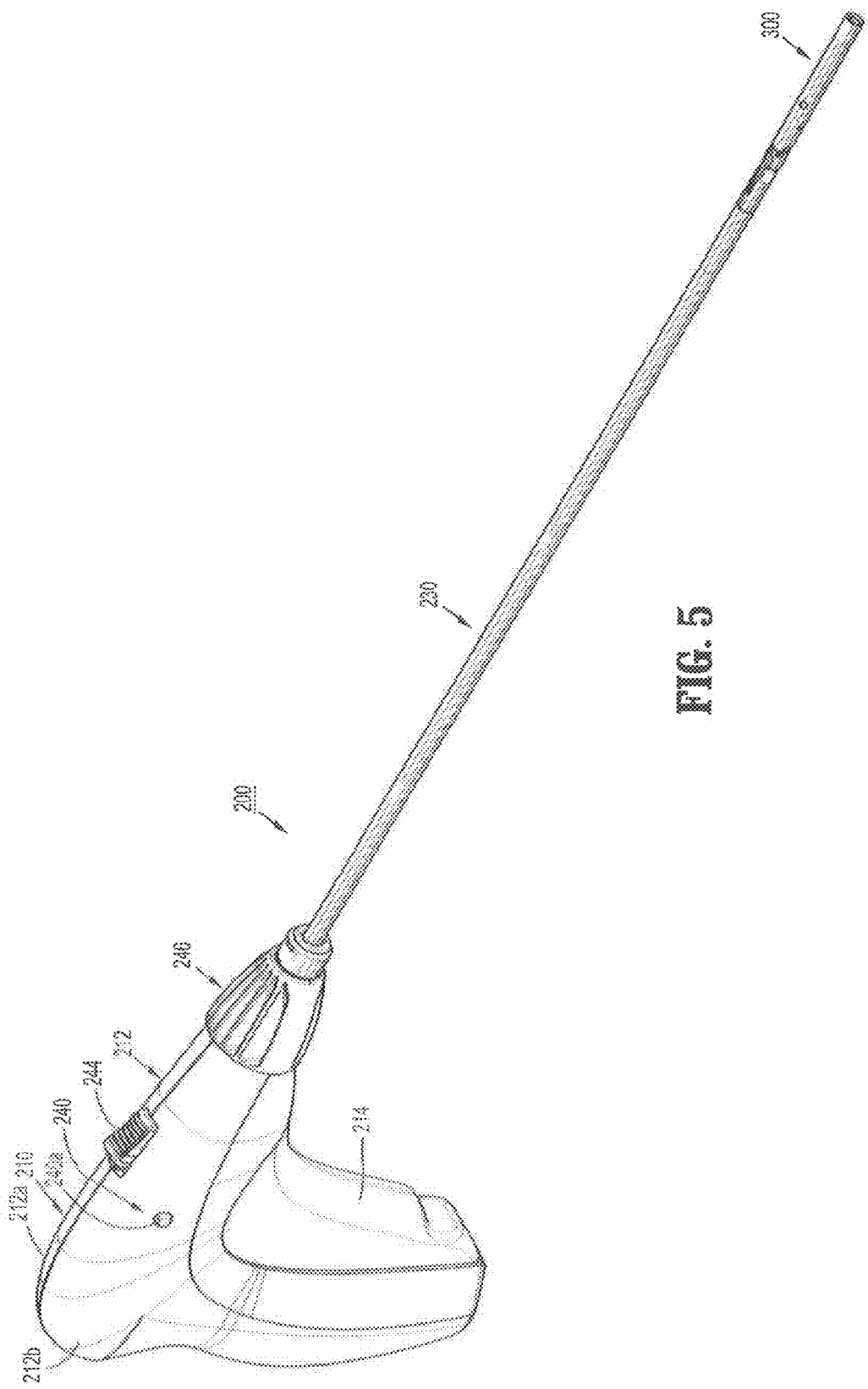
FIG. 5 is an endoscopic surgical device according to an aspect of the present disclosure.
Figure 6:
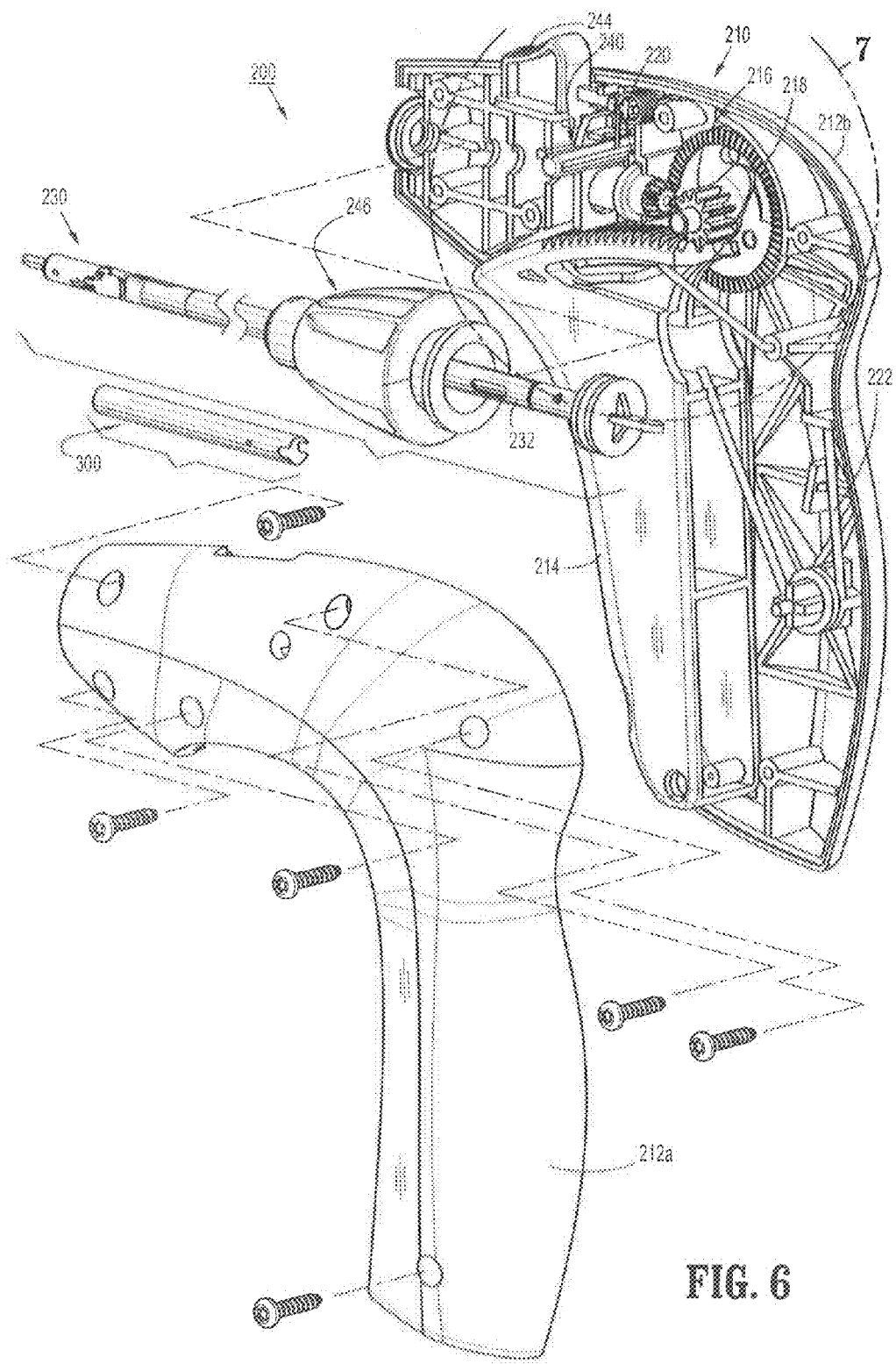
FIG. 6 is a perspective view, with parts separated, of the endoscopic surgical device of FIG. 5.
Figure 7:
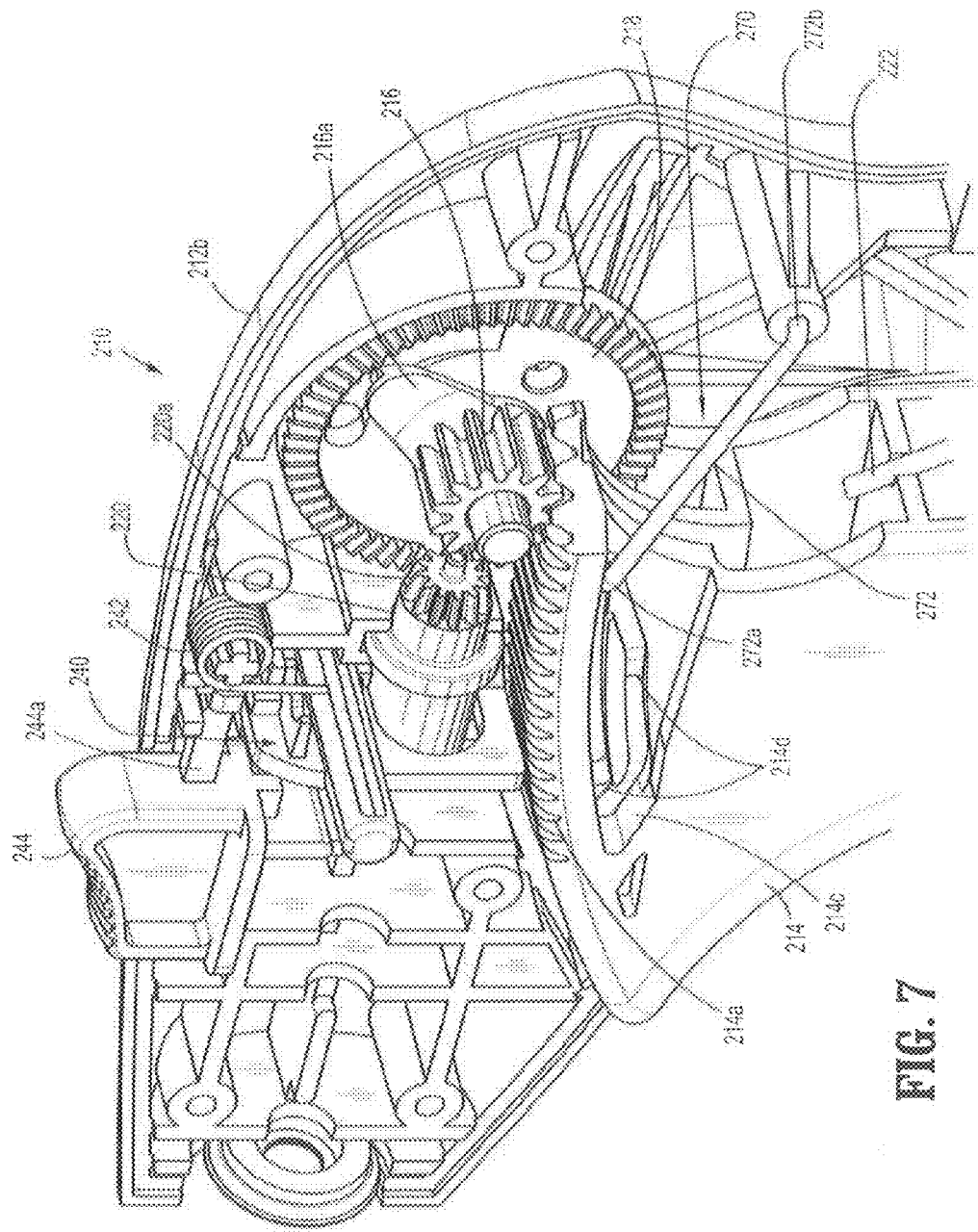
FIG. 7 is an enlarged view of the indicated area of detail of FIG. 6.

As seen in FIG. 4, body section 134 of tissue-snaring section 130 is tapered, i.e., becoming smaller toward the distal end of threaded tissue-snaring section 130, and terminates or truncates to a distal truncation point "TP", prior to reaching an apex or tip of anchor 100. Body section 134 includes a concave taper such that, for a given length, a minimum diameter body section 134 is defined upon truncation thereof which is approximately less than 0.01 inches.

Anchor 100 includes a transverse dimension "D", of a distal-most thread in the threaded tissue-snaring section 130 which is as large as design constraints will allow or approximately greater than 0.040 inches. In accordance with the present disclosure, a small truncated body diameter and a large value of "D" minimizes tissue indentation. The tissue-snaring threads 132 terminate at distal tip 136, which is distal of the truncation point "TP" of body section 134.

By providing a distal tip 136 extending distally of truncation point "TP" of tissue-snaring section 130, a penetration of the mesh, by anchor 100, is eased; and an indentation of the mesh into relatively soft tissue, by anchor 100, is minimized, as compared to an anchor having a non-truncated body with tapered threads.

For a given force applied to a surgical mesh by the surgeon, exerting a distal force on a tack applier the larger the dimension "D" of anchor 100 the less the pressure exerted to cause indentation of an underlying tissue and surgical mesh.

Anchor 100 is non-cannulated and is constructed from a suitable bioabsorbable material, such as, polylactide, polyglycolide. Anchor 100 is formed from a proprietary biocompatible co-polymer (Lactomer USS L1, Boehringer Ingelheim LR 704 S, or Boehringer Ingelheim LG-857).

Turning now to FIGS. 5-49, an endoscopic surgical device, in the form of an endoscopic surgical tack applier or tacker, is shown generally as 200. Tack applier 200 includes a handle assembly 210, and an endoscopic assembly 230 extending from handle assembly 210 and configured to store and selectively release or fire a plurality of anchors 100 therefrom and into mesh "M" overlying tissue "T". (see FIG. 50).

As seen in FIGS. 5-14, handle assembly 210 includes a handle housing 212 formed from a first half-section 212a and a second half section 212b joined to one another. First half-section 212a and second half section 212b of handle housing 212 may be joined to one another using know methods by those of skill in the art, including and not limited to welding, fasteners (i.e., screws) and the like.

Handle assembly 210 includes a trigger 214 pivotably connected to handle housing 212, at a location remote from endoscopic assembly 230. Handle assembly 210 includes a biasing member 222 configured for maintaining trigger 214 in an extended or un-actuated position. Biasing member 222 is also configured to have a spring constant sufficient to return trigger 214 to the un-actuated position.

Trigger 214 defines a gear rack 214a formed thereon at a location opposite or remote from the pivot of trigger 214. Gear rack 214a of trigger 214 is configured for operative engagement with a pinion gear 216 rotatably supported in handle housing 212. Gear rack 214a and pinion gear 216 are dimensioned such that one complete squeeze of trigger 214 results in one complete revolution of pinion gear 216.

As seen in FIGS. 7, 9, 11, 47 and 48, handle assembly 210 includes a timing system 270 associated therewith. Timing system 270 includes a raceway 214c formed in a surface of trigger 214. Raceway 214c defines a plurality of steps 214d therealong, and a home position 214e (FIGS. 9 and 48) formed therein.

Timing system 270 includes a resilient and deflectable arm 272 having a first end 272a operative connected or disposed in raceway 214c and that is in contact with steps 214d as first end 272a thereof travels around raceway 214c. Deflectable arm 272 further includes a second end 272b that is connected to handle housing half 212b. Raceway 214c of trigger is configured such that when trigger 214 is in a fully un-actuated position, first end 272a of deflectable arm 272 is located in the home position 214e of raceway 214c.

Figure 47:
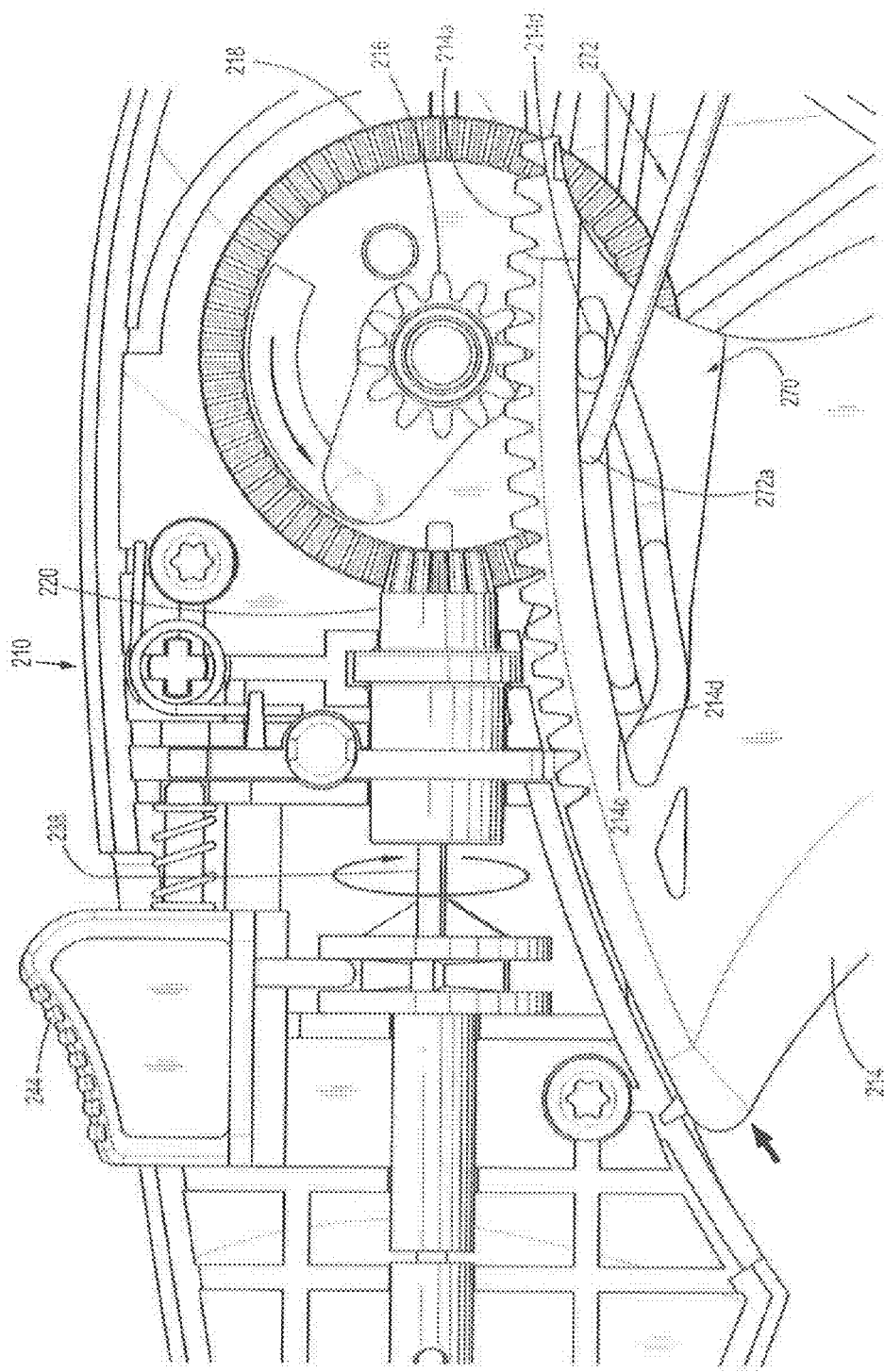
FIG. 47 is an enlarged elevational view of the handle assembly shown in FIGS. 9 and 10, illustrating an operation of an audible/tactile feedback member of the handle assembly, shown in an position following an initial actuation of a trigger.
Figure 48:
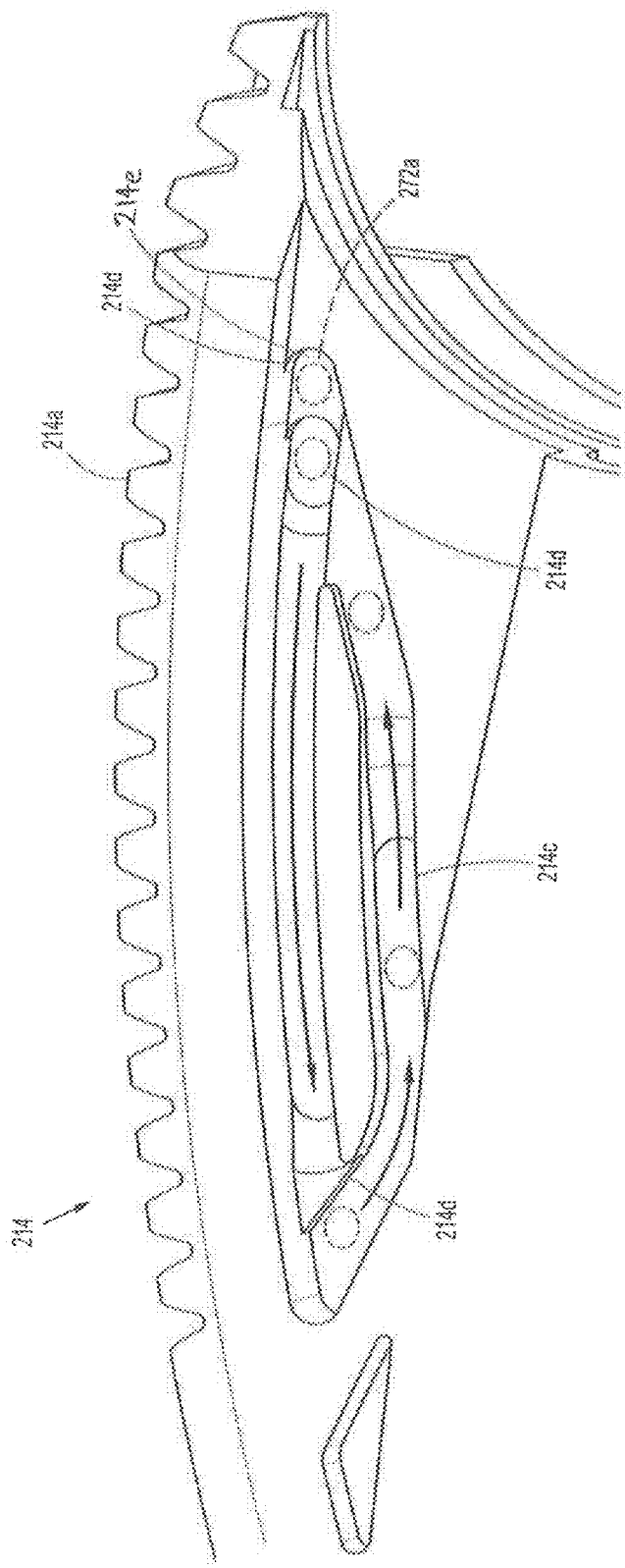
FIG. 48 is an enlarged elevational view of the handle assembly shown in FIGS. 9 and 10, illustrating an operation of the audible/tactile feedback member of the handle assembly, shown in an position following a complete actuation of the trigger.

In operation, as seen in FIGS. 47 and 48, when trigger 214 is in the fully un-actuated position, as mentioned above, first end 272a of deflectable arm 272 is located in the home position 214e of raceway 214c. Then, as trigger 214 is actuated, first end 272a of arm 272 rides through and/or along raceway 214c (in a single direction) formed in trigger 214. First end 272a of arm 272 moves uni-directionally over steps 214d of raceway 214c, such that, if trigger 214 is released after a partial squeeze, first end 272a of arm 272 can not move backwards or in reverse through raceway 214c due to steps 214d and trigger 214 can not return to the fully un-actuated position.

As so configured and operable, and as will be described in detail below, end effector or SULU 300 may only be removed and replaced when trigger 214 is in the fully un-actuated, home and locked position. As such, an end effector or SULU 300 can not be removed or replaced or loaded on/in handle assembly 200 while trigger 214 is in a short-stroked condition (i.e., partially actuated).

Additionally, as first end 272a of arm 272 moves over steps 214d of raceway 214c, first end 272a of arm 272 snaps over steps 214d and creates an audible sound/click and/or a tactile vibration for the surgeon. It is contemplated that timing system 270 includes sufficient steps 214d in raceway 214c so as to create an audible/tactile indication when trigger 214 is in a fully un-actuated home or lockout position (for loading/unloading end effector or SULU 300); after trigger 214 has been fully actuated to fire a singe surgical anchor 100; and when trigger 214 is reset to the fully un-actuated home position (wherein trigger 214 may once again be locked) and ready to fire another surgical anchor 100.

As seen in FIGS. 7 and 9-12, handle assembly 210 includes a pinion gear 216 having an arm 216a extending radially therefrom and a cam or ramp 216b extending/projecting from arm 216a. Cam 216b includes a front end 216c having a height defining a shoulder, and tail end 216d tapering into arm 216a.

As seen in FIGS. 7-11 and 14, handle assembly 210 further includes a first bevel gear 218, in the form of a crown gear, operatively engaged/associated with pinion gear 216. First bevel gear 218 defines an arcuate slot 218a formed in a face 218d thereof for selectively receiving and engaging cam 216b of pinion gear 216. Slot 218a includes a front end wall 218b configured to engage front end 216c of cam 216b of pinion gear 216, and tapers along a length thereof to be flush with face 218d of first bevel gear 218.

In use, as trigger 214 is actuated, gear rack 214a thereof is moved in an axial or arcuate first direction to thereby rotate pinion gear 216, meshed therewith, in a first direction. As pinion gear 216 is rotated in the first direction, front end 216c of cam 216b of pinion gear 216 is rotated in a first direction until front end 216c engages or contacts front end wall 218a of slot 218b of first bevel gear 218. After front end 216c of pinion gear 216 engages or contacts front end wall 218a of slot 218b of first bevel gear 218, continued rotation of pinion gear 216 in the first direction results in concomitant rotation of first bevel gear 218 in a first direction. At this point, first bevel gear 218 continues to rotate in the first direction so long as trigger 214 is being actuated and gear rack 214a is moving in the first direction.

When actuation of trigger 214 is stopped, either prior to complete actuation or following complete actuation, rotation of first bevel gear 218, in the first direction, is also stopped.

Upon the completion of a partial or complete actuation of trigger 214 and a release thereof, gear rack 214a thereof is moved in a second direction (opposite the first direction) to thereby rotate pinion gear 216 in a second direction. As pinion gear 216 is rotated in the second direction rear end 216d of cam 216b thereof slides along slot 218b of first bevel gear 218, and if the rotation in the second direction is sufficient, slides out of slot 218b of bevel gear 218 and along face 218d of first bevel gear 218.

If trigger 214 was fully actuated, a complete release of trigger 214, and return to the fully un-actuated position, wherein first end 272a of deflectable arm 272 is returned to the home position 214e of raceway 214c, will result in pinion gear 216 making a complete revolution, in the second direction, until front end 216c of cam 216b of pinion gear 216 clears front end wall 218a of slot 218b of first bevel gear 218 to thereby re-enter slot 218b of first bevel gear 218.

Figure 8:
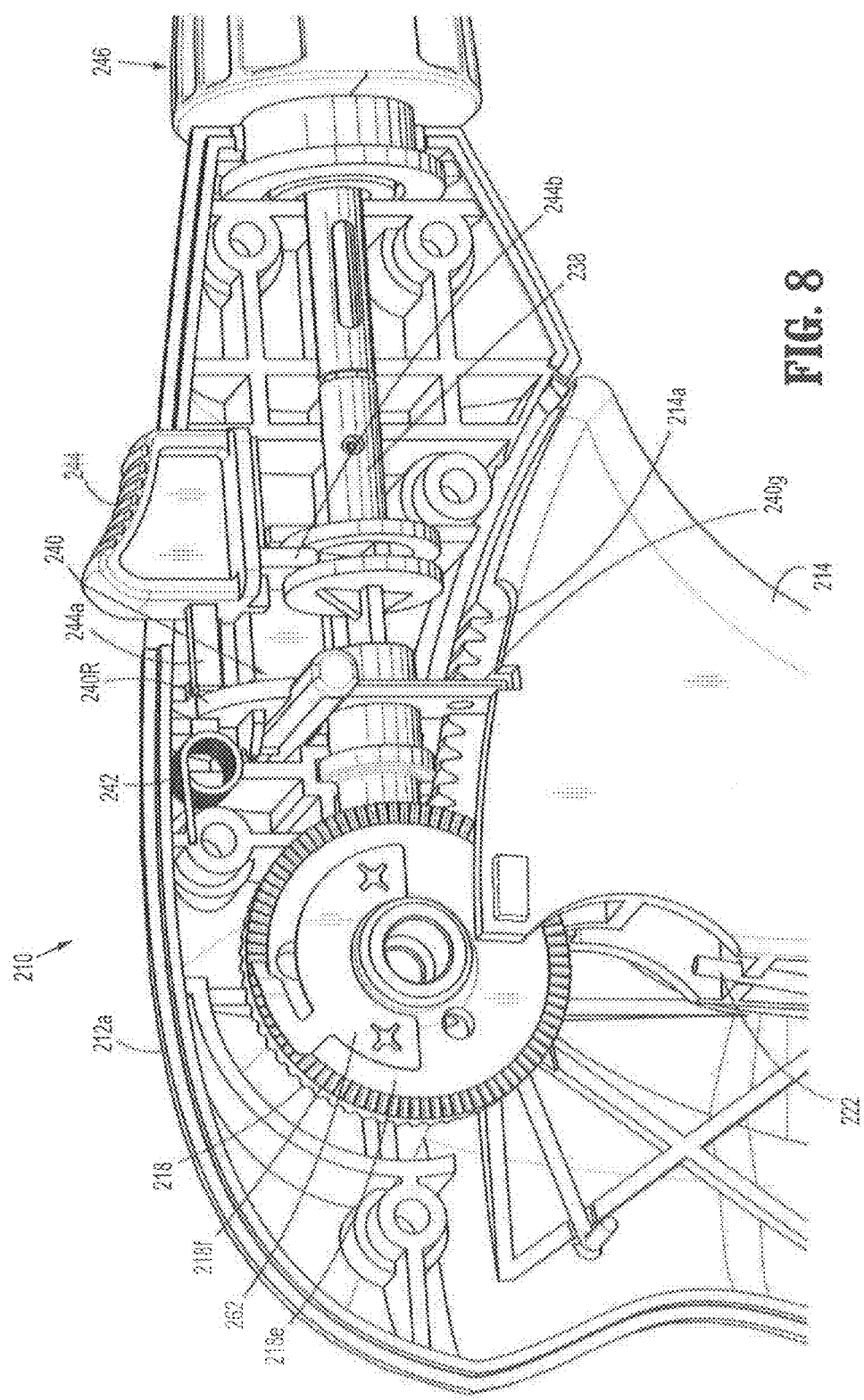
FIG. 8 is a rear perspective view, with a first housing half-section removed therefrom, of a handle assembly of the endoscopic surgical device of FIG. 5.
Figure 9:
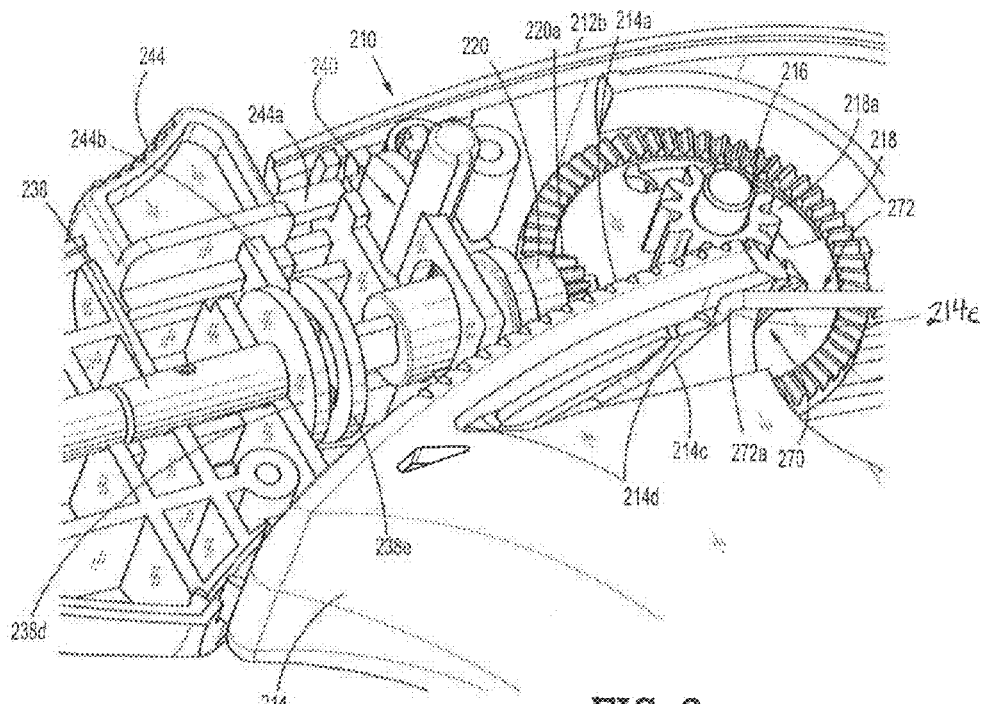
FIG. 9 is a front perspective view, with a second housing half-section removed therefrom, of a handle assembly of the endoscopic surgical device of FIG. 5.
Figure 10:
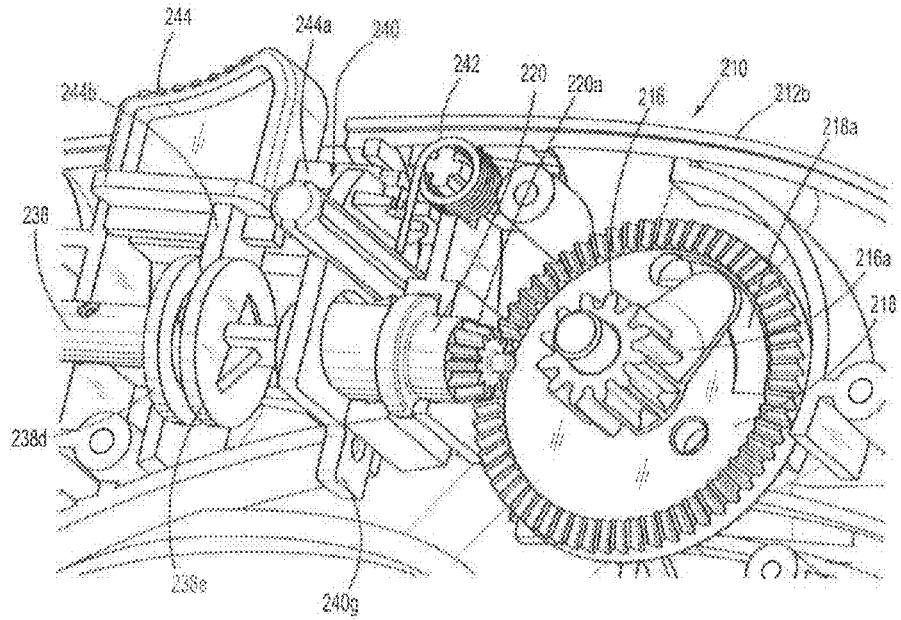
FIG. 10 is a rear perspective view, with a second housing half-section and trigger removed therefrom, of the handle assembly of the endoscopic surgical device of FIG. 5.
Figure 11:
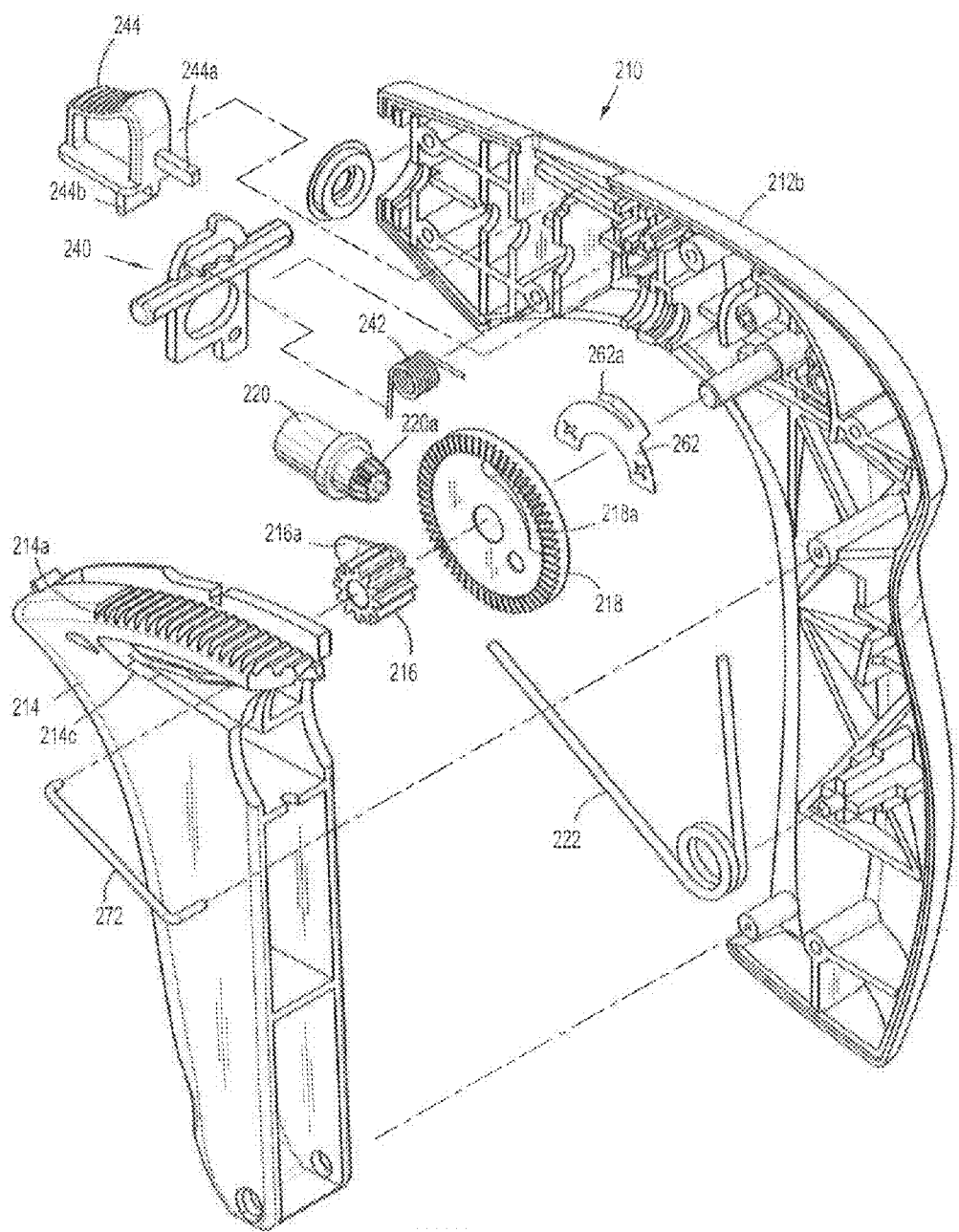
FIG. 11 is a rear perspective view, with parts separated, and with a second housing half-section removed therefrom, of the handle assembly of the endoscopic surgical device of FIG. 5.
Figure 12:
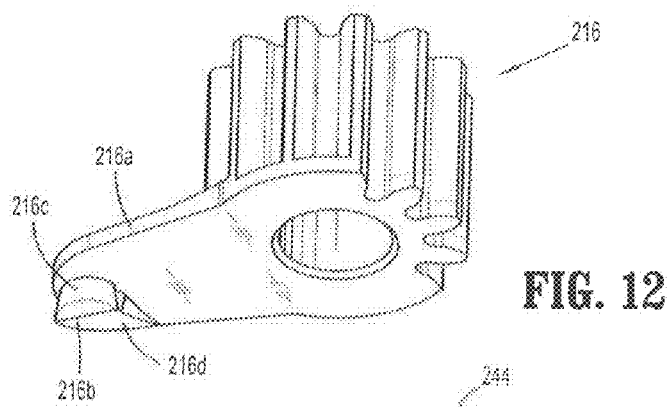
FIG. 12 is a perspective view of a pinion gear of the handle assembly of FIGS. 8-11.
Figure 13:
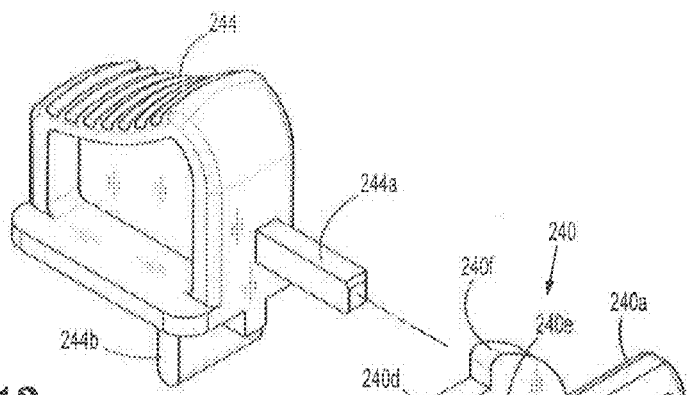
FIG. 13 is a perspective view of a button and slider of the handle assembly of FIGS. 8-11.
Figure 14:
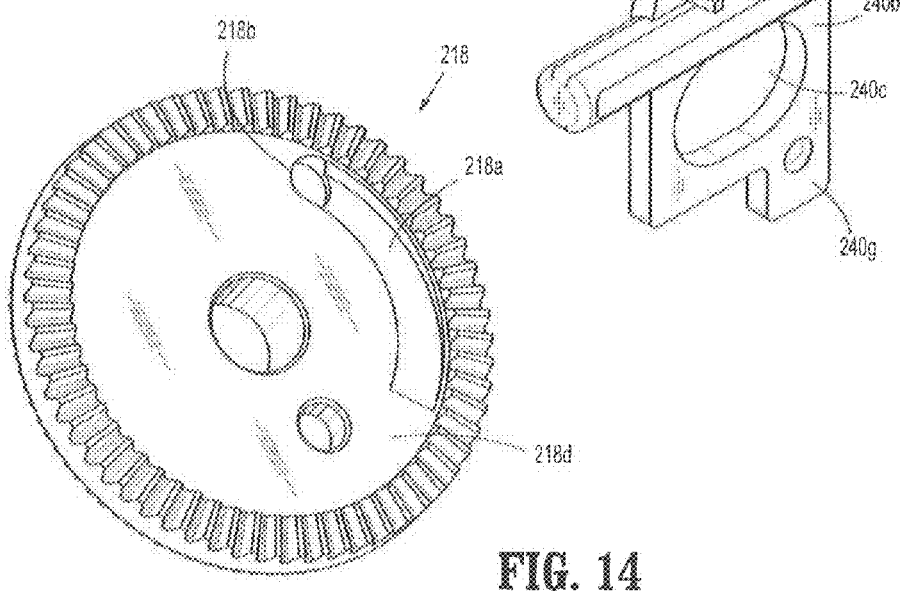
FIG. 14 is a perspective view of a bevel gear of the handle assembly of FIGS. 8-11.

As seen in FIGS. 8 and 11, handle assembly 210 of tack applier 200 is provided with a ratchet mechanism 260 which is configured to inhibit or prevent inner shaft assembly 238 from backing-out or reversing after anchor 100 has been at least partially driven into tissue. Ratchet mechanism 260 includes, as seen in FIGS. 8 and 11, a series of ratchet teeth 218f formed on a rear surface 218e of first bevel gear 218.

Ratchet mechanism 260 further includes a spring clip 262 secured within handle assembly 210. Spring clip 262 includes a resilient finger 262a configured for engagement with ratchet teeth 218f formed on rear surface 218e of first bevel gear 218.

Each ratchet tooth 218f includes a shallow angled side and a steep angled side. In this manner, resilient finger 262a of spring clip 262 engages with ratchet teeth 218f in such a manner that as first bevel gear 218 is rotated, in a first direction resilient, finger 262a of spring clip 262 cams over the shallow angled side of ratchet teeth 218f. Also, if first bevel gear 218 is rotated in a second direction (opposite to the first direction), resilient finger 262a of spring clip 262 stops against the steep angled side of ratchet teeth 218f thereby preventing or inhibiting first bevel gear 218 from rotating in the second direction. As such, any reverse rotation or "backing-out" of anchor 100 or inner shaft assembly 238 (tending to cause first bevel gear 218 to rotate in the second direction), during a driving or firing stroke, is inhibited or prevented.

In an alternate embodiment, first bevel gear 218 may be maintained from rotating in the second or opposite direction, upon the rotation of pinion gear 216, in the second direction, due to a coefficient of static friction between first bevel gear 218 and a surface of handle housing 212, or a coefficient of static friction between first bevel gear 218 and a pin upon which first bevel gear 218 is supported, which will tend to maintain first bevel gear 218 stationary. Such a configuration and assembly functions as a ratchet mechanism or the like for tack applier 200.

With reference to FIGS. 6, 7 and 9-11, handle assembly 210 further includes a second or pinion-bevel gear 220 having gear teeth 220a operatively engaged or meshed with gear teeth 218c formed at the outer radial edge and on front face 218d of first bevel gear 218. Pinion-bevel gear 220 is secured to a proximal end of an inner shaft assembly 238 of anchor retaining/advancing assembly 230 (see FIG. 15). In an embodiment, pinion-bevel gear 220 is keyed to proximal end of inner shaft assembly 238 of anchor retaining/advancing assembly 230 such that inner shaft assembly 238 is capable of axial displacement relative to pinion-bevel gear 220 and is prevented from rotation relative to pinion-bevel gear 220.

In use, as described above, upon squeezing of trigger 214, gear rack 214a thereof causes pinion gear 216 to rotate in the first direction. Rotation of pinion gear 216, in the first direction, results in rotation of first bevel gear 218 in the first direction and, in turn, rotation of pinion-bevel gear 220 in a first direction. As pinion-bevel gear 220 is rotated in the first direction, pinion-bevel gear 220 transmits the rotation to inner shaft assembly 238 of anchor retaining/advancing assembly 230.

As seen in FIGS. 5-11 and 13, handle assembly 210 includes a button 240 supported on handle housing 212 and being configured to permit and inhibit actuation of trigger 214, and for effectuating a loading/retention and a release/removal of an end effector 300 to anchor retaining/advancing assembly 230. Button 240 includes a pin 240a slidably supported in handle housing 212. Pin 240a is oriented in a direction orthogonal to the longitudinal axis of anchor retaining/advancing assembly 230. As seen in FIGS. 38-41, pin 240a has a length such that when button 240 is in a first position, a first end of pin 240a extends from a first side of handle housing 212, and when button 240 is in a second position, a second end of pin 240a extends from a second side of handle housing 212.

As seen in FIGS. 13 and 38-41, button 240 includes a plate 240b supported on and connected to pin 240a. Plate 240b defines an elongate slot 240c therein, through which a stem 220a of pinion-bevel gear 220 extends. Elongate slot 240c of plate 240b defines a major axis which is parallel relative to a longitudinal axis of pin 240a. In use, as pin 240a is moved between the first position and the second position, plate 240b is moved between respective first and second positions.

Button 240 includes a first detent or recess 240d defined in plate 240b that is engaged by a biasing member 242 when button 240 is in the first position, and a second detent or recess 240e defined in plate 240b that is engaged by biasing member 242 when button 240 is in the second position. The engagement of biasing member 242 in either first detent 240d or second detent 240e of button 240 functions to help maintain button 240 in either the first or second position.

Figure 42:
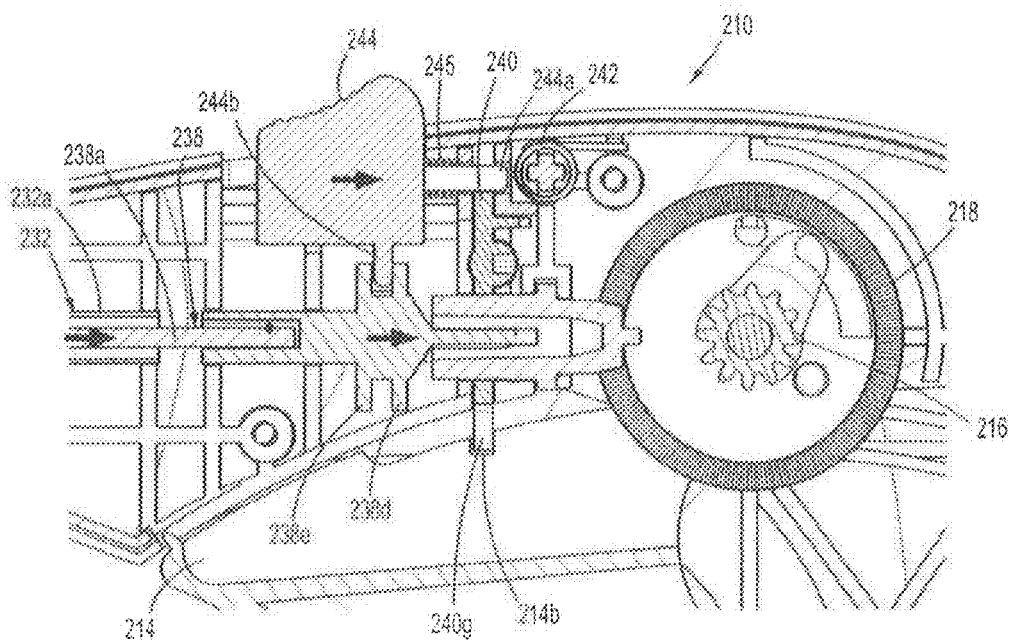
FIG. 42 is an enlarged elevational view of the handle assembly shown in FIGS. 9 and 10, illustrating an operation of the slider.

In an embodiment, biasing member 242 may be in the form of a plunger spring, and, as seen in FIGS. 33 and 42, in another embodiment, biasing member 242 may be in the form of a torsion spring. A torsion spring is contemplated over a plunger spring in order to reduce overall costs of surgical tacker 200.

As seen in FIGS. 8, 13, 33 and 38-42, button 240 includes a first wall 240f extending from plate 240b, and a second wall 240g extending from plate 240b. In use, when button 240 is in the first position, first wall 240f thereof blocks or inhibits movement of a load/release slider 244, and when button 240 is in the second position, first wall 240f thereof permits movement of load/release slider 244. Similarly, in use, when button 240 is in the second position (only achievable when trigger 214 is in a fully un-actuated or home position), second wall 240g thereof blocks or inhibits actuation of trigger 214 by second wall 240g extending into a notch 214b of trigger 214; and when button 240 is in the first position, second wall 240f is clear of notch 214b of trigger 214 to permit actuation of trigger 214.

As seen in FIGS. 5-11, 13 and 38-42, handle assembly 210 includes a load/release slider 244 slidably supported on handle housing 212 and being configured to effectuate a loading/retention and a release/removal of an end effector 300, in the form of a single use loading unit (SULU) or disposable loading unit (DLU), as will be discussed in greater detail below. Slider 244 includes a first stem 244a extending proximally therefrom and toward button 240. Specifically, first stem 244a of slider 244 is in axial registration with first wall 240f extending from plate 240b of button 240 when button 240 is in the first position (see FIG. 39), and out of axial registration with first wall 240f of button 240 when button 240 is in the second position (see FIG. 41).

Figure 15:
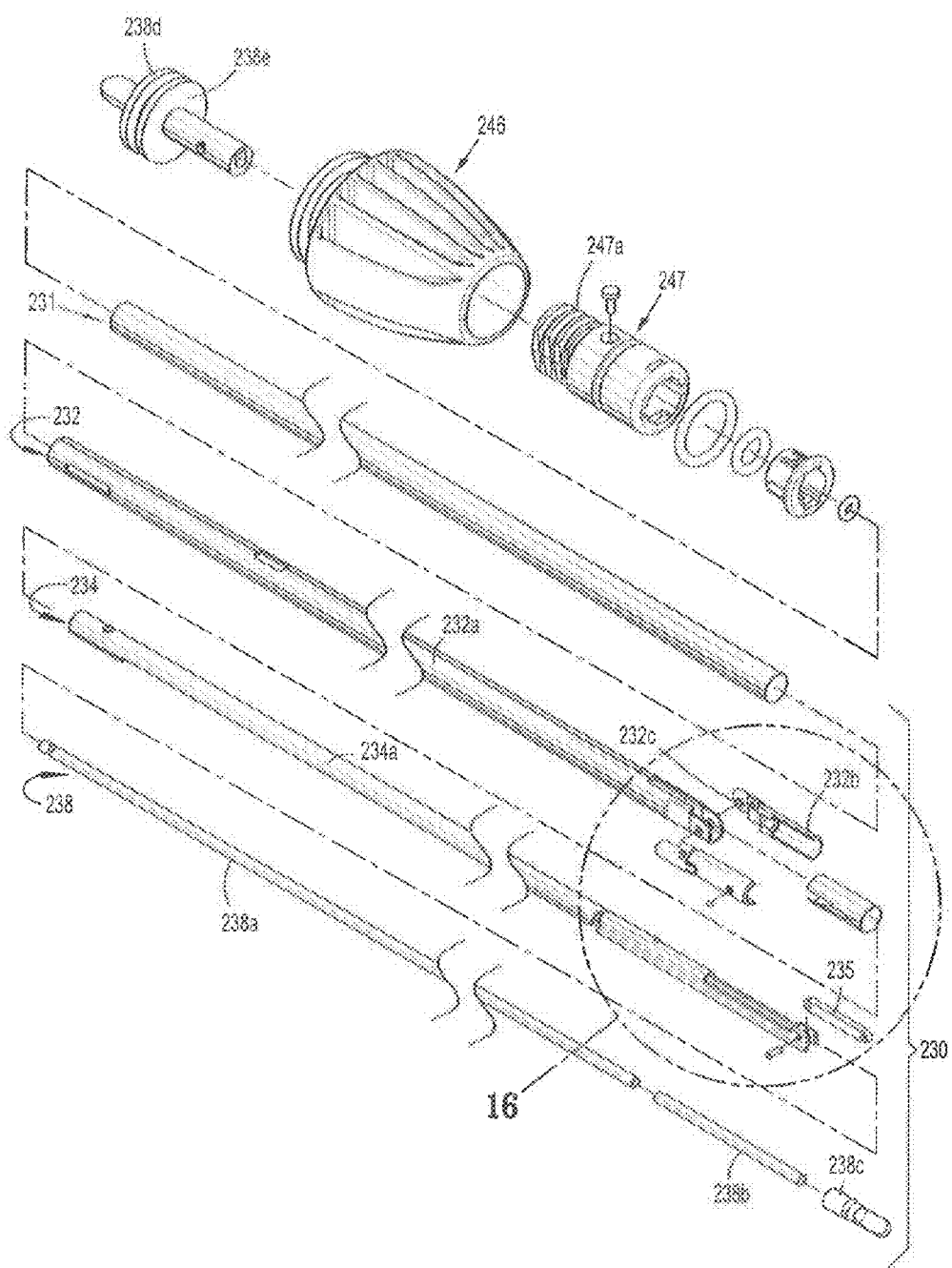
FIG. 15 is a front perspective view, with parts separated, of an endoscopic assembly of the endoscopic surgical device of FIG. 5.
Figure 16:
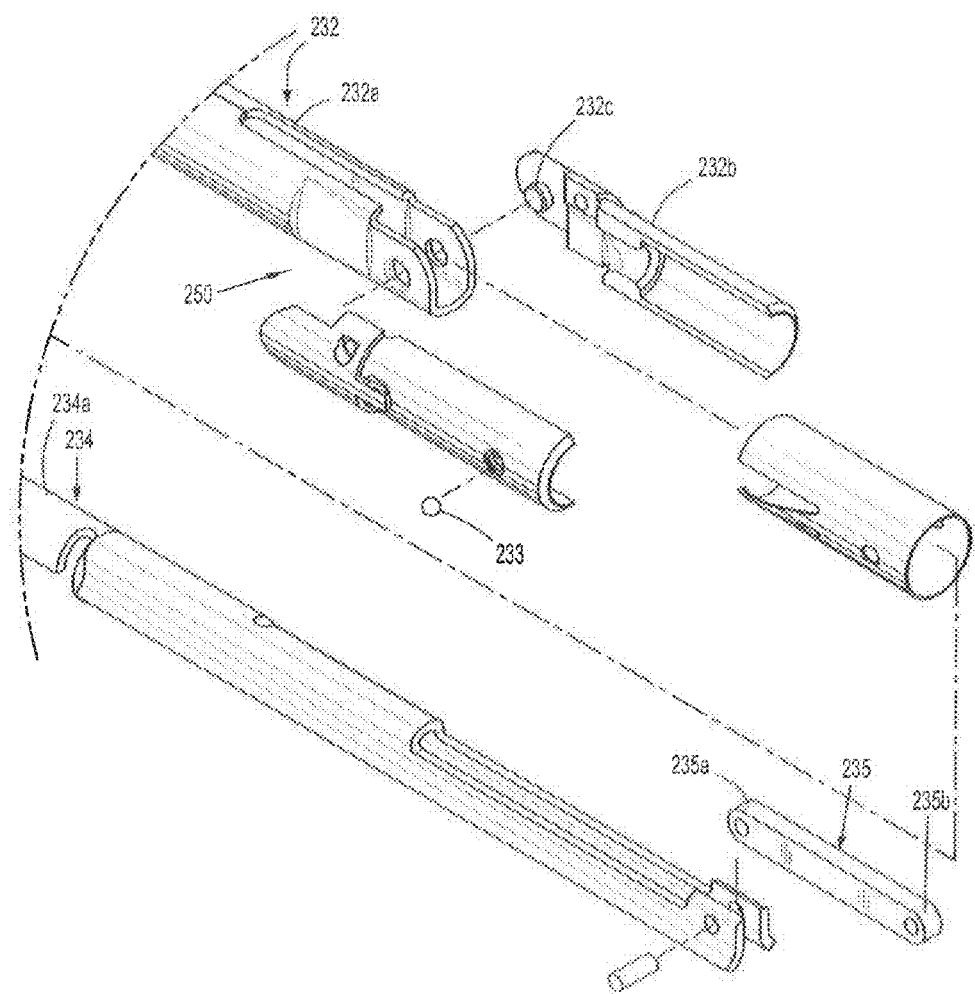
FIG. 16 is an enlarged view of the indicated area of detail of FIG. 15.

Slider 244 further includes a second stem 244b extending therefrom in a direction toward inner shaft assembly 238 of anchor retaining/advancing assembly 230. As seen in FIGS. 15 and 42, inner shaft assembly 238 supports a pair of axially spaced apart radial flanges 238d, 238e which bookend (i.e., one flange being distal and one flange being proximal of second stem 244b).

Figures 40, 41:
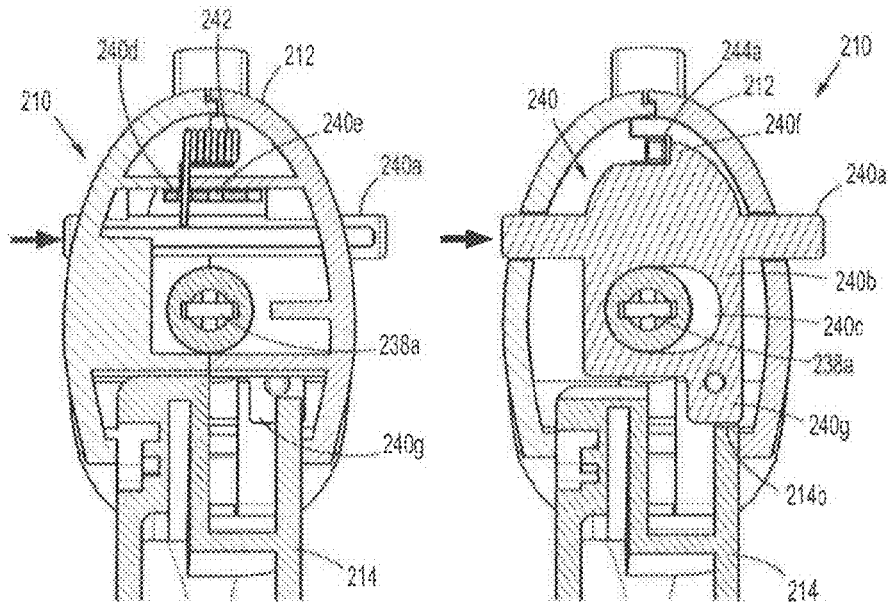
FIG. 40 is a cross-sectional view as taken though 34-34 of FIG. 33.
FIG. 41 is a cross-sectional view as taken though 34-34 of FIG. 33.

In use, as seen in FIGS. 41 and 42, when button 240 is in the second position (wherein trigger 214 is locked in the fully un-actuated position) such that first stem 244a of slider 244 is out of axial registration with first wall 240f of button 240, slider 244 is free to move between a first or distal position and a second or proximal position. As slider 244 is moved from the first position to the second position thereof, second stem 244b of slider 244 exerts a force on proximal radial flange 238d of inner shaft assembly 238 to urge inner shaft assembly 238 proximally from a respective first position to a respective second position. It follows that as slider 244 is moved from the second position to the first position thereof, second stem 244b of slider 244 exerts a force on distal radial flange 238e of inner shaft assembly 238 to urge inner shaft assembly 238 distally from the respective second position to the respective first position.

In accordance with the present disclosure, as inner shaft assembly 238 is moved between the respective first and second positions thereof, inner shaft assembly 238, being connected to coupling member 238c results in connecting member 238c also moving between a respective first position and a respective second position.

Slider 244 may be biased to the first or distal position by a biasing member 245 (see FIG. 42).

As seen in FIGS. 5, 6, 8, 15, 17, 33-35 and 45, handle assembly 210 includes an articulation knob 246 rotatably supported on handle housing 212. Articulation knob 246 defines an inner helical thread 246a Inner helical thread 246a meshingly receives or engages an outer thread 247a of a connection nut 247 that is non-rotatably connected to proximal tube portion 234a of inner tube assembly 234 of anchor retaining/advancing assembly 230. Connection nut 247 may be keyed to articulation knob 246 so as to not rotate relative to articulation knob 246 as articulation knob 246 is rotated. Alternatively, the surgeon may manually grip a distal end of connection nut 247 (which is projecting/extending distally of articulation knob 246) as articulation knob 246 is rotated.

Figure 45:
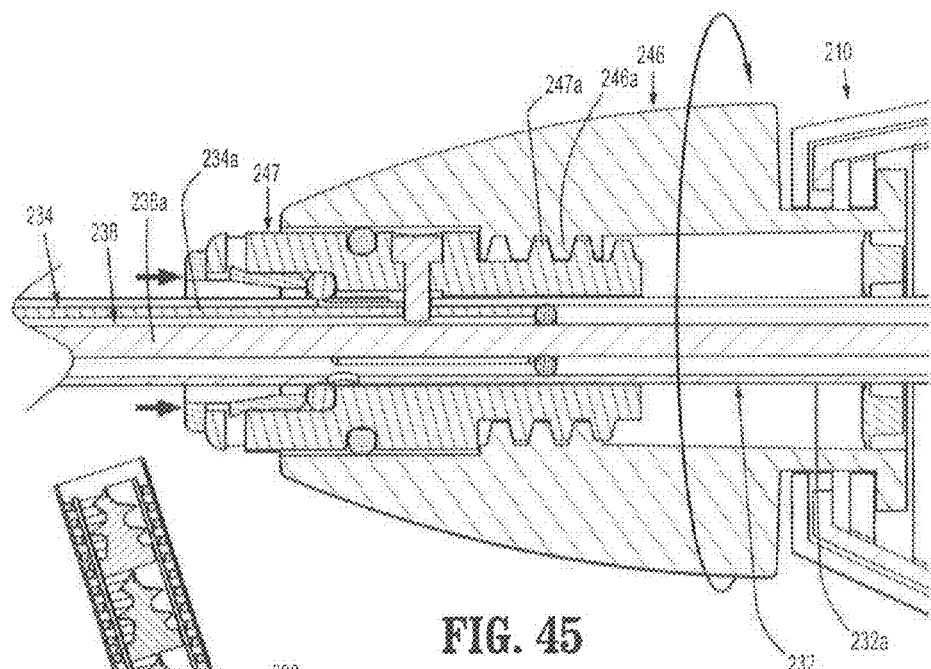
FIG. 45 is a longitudinal, cross-sectional view an articulation knob of the handle assembly of FIGS. 5-11, illustrating a rotation thereof.
Figure 46:
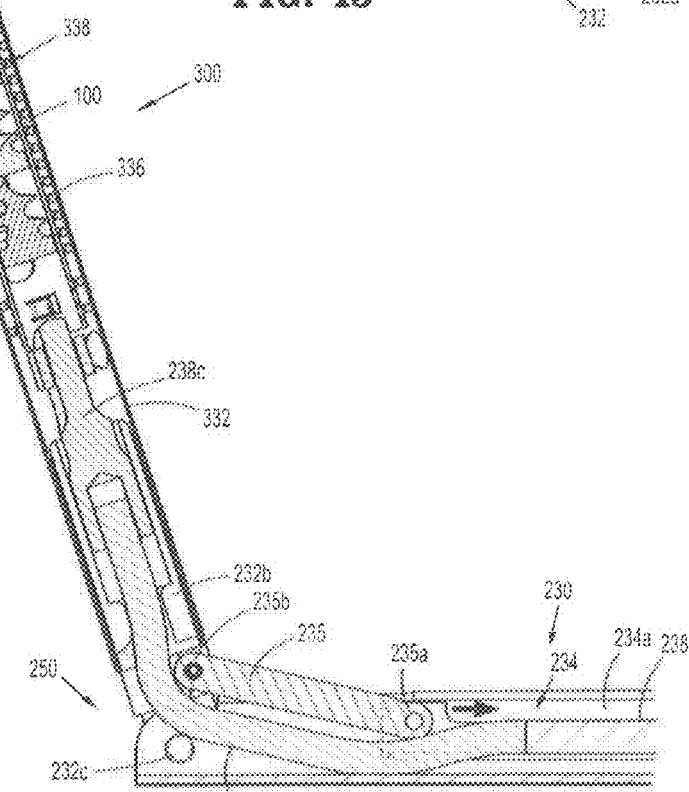
FIG. 46 is a longitudinal, cross-sectional view of a distal end of the endoscopic surgical device illustrating an articulation of the end effector relative to the endoscopic assembly due to a rotation of the articulation knob.

In use, as seen in FIGS. 45 and 46, with connection nut 247 retained against rotation about the longitudinal axis, as articulation knob 246 is rotated in a first direction, connection nut 247 travels along inner helical thread 246a of articulation knob 246 to cause inner articulation tube assembly 234 to move in a respective first or distal axial direction; and as articulation knob 246 is rotated in a second direction, connection nut 247 travels along inner helical thread 246a of articulation knob 246 to cause inner articulation tube assembly 234 to move in a respective second or proximal axial direction. In accordance with the present disclosure, rotation of articulation knob 246 in the respective first and second directions results in the articulating and straightening of anchor retaining/advancing assembly 230, as will be discussed in greater detail below.

Turning now to FIGS. 15, 16, 32, 33 and 42-46, as seen therein, endoscopic assembly 230 includes an outer tube 231, an outer support tube assembly 232 disposed within outer tube 231, an inner articulation tube assembly 234, and an inner shaft assembly 238. Outer support tube assembly 232 includes a proximal support tube portion 232a secured to and extending from handle housing 212, and a distal support tube portion 232b pivotally connected to proximal tube portion 232a by a pivot pin 232c (see FIGS. 15 and 16) at an articulation joint 250.

As seen in FIGS. 15, 16, 43 and 44, distal support tube portion 232b supports a ball detent 233 in an outer surface thereof. Ball detent 233 functions to selectively secure and retain end effector 300 to endoscopic assembly 230. In use, as will be discussed in greater detail below, as seen in FIGS. 37 and 42, ball detent 233 is acted on by an outer camming surface/relief $238c_1$ of coupling member 238 which acts on ball detent 233 to move ball detent 233 radially outward when inner shaft assembly 238 is a distal position.

Inner articulation tube assembly 234 includes a proximal tube portion 234a concentrically and slidably disposed within proximal tube portion 232a of outer support tube assembly 232. As seen in FIG. 33, proximal end 234b of proximal tube portion 234a is non-rotatably connected to connection nut 247.

Inner articulation tube assembly 234 includes an articulation link 235 having a proximal end 235a pivotally connected to a distal end of proximal tube portion 234a, and a distal end 235b pivotally connected to distal tube portion 232b of outer support tube assembly 232. Distal end 235b of articulation link 235 is pivotally connected to distal tube portion 232b of outer support tube assembly 232 at a location offset from the central longitudinal axis of anchor retaining/advancing assembly 230, in a direction substantially away from pivot pin 232c of articulation joint 250.

In operation, as seen in FIGS. 45 and 46, upon an axial translation of proximal tube portion 234a, for example in a proximal direction, due to a rotation of articulation knob 246 and proximal axial movement of connection nut 247 as described above, proximal tube portion 234a acts or pulls on articulation link 235 to cause articulation link 235 to translate in a proximal direction. As articulation link 235 is axially translated in a proximal direction, articulation link 235 acts or pulls on distal tube portion 232b of outer support tube assembly 232 to cause distal tube portion 232b to pivot about a pivot axis of pivot pin 232c. As distal tube portion 232b is pivoted, distal tube portion 232b causes end effector 300 to be moved to an articulated orientation relative to the central longitudinal axis of anchor retaining/advancing assembly 230.

It follows that upon an axial translation of proximal tube portion 234a in a distal direction, due to a distal movement of slider 244, as described above, proximal tube portion 234a acts or pushes on articulation link 235 to cause articulation link 235 to translate in a distal direction. As articulation link 235 is axially translated in a distal direction, articulation link 235 acts or pushes on distal tube portion 232b of outer support tube assembly 232 to cause distal tube portion 232b to pivot about a pivot axis of pivot pin 232c. As distal tube portion 232b is pivoted, distal tube portion 232b causes end effector 300 to be returned to a non-articulated orientation relative to the central longitudinal axis of anchor retaining/advancing assembly 230.

In accordance with the present disclosure, distal tube portion 232b of anchor retaining/advancing assembly 230 is pivotable in a single direction relative to proximal tube portion 232a of anchor retaining/advancing assembly 230.

With reference to FIGS. 15, 19, 32, 33 and 35-46, inner actuation shaft assembly 238 includes a proximal rigid shaft portion 238a, a distal flexible shaft portion 238b non-rotatably connected to and extending from a distal end of proximal rigid shaft portion 238a, and a coupling member 238c non-rotatably connected to a distal end of distal flexible shaft portion 238b. Second or pinion-bevel gear 220 is non-rotatably connected to a proximal end of proximal rigid shaft portion 238a of inner actuation shaft assembly 238. Inner actuation shaft assembly 238 is configured such that distal flexible shaft portion 238b extends across and beyond articulation joint 250.

Desirably, coupling member 238c is rotatably and slidably supported in distal tube portion 232b of outer support tube assembly 232 so as to accommodate and/or account for variations in length of distal flexible shaft portion 238b when distal flexible shaft portion 238b is in a flexed condition. Coupling member 238c is substantially tongue shaped and extends in a distal direction distally from distal tube portion 232b of outer support tube assembly 232. Coupling member 238c is configured for non-rotatable connection to inner tube 338 of end effector 300, as will be discussed in greater detail below.

Distal flexible shaft portion 238b is fabricated from a torsionally stiff and flexible material, such as, for example, stainless steel.

It is contemplated that distal flexible shaft portion 238b may have an outer diameter of about 0.08'. Meanwhile, anchor retaining/advancing assembly 230 has an outer diameter of about 0.22'. A ratio of the outer diameter of distal flexible shaft portion 238b to the outer diameter of anchor retaining/advancing assembly 230 is about 2.8.

Inner actuation shaft assembly 238 is configured to perform at least a pair of functions, a first function relating to the securing and release of an end effector or SULU 300 to distal tube portion 232b of outer support tube assembly 232 upon an axial translation thereof, and a second function relating to the firing of fasteners 100 from end effector or SULU 300 when end effector or SULU 300 is coupled to distal tube portion 232b of outer support tube assembly 232 upon a rotation thereof.

In order to prepare surgical tacker 200 for receipt of end effector or SULU 300 or to replace a spent end effector or SULU 300 with a new end effector or SULU 300, as seen in FIGS. 38-44, and as mentioned above, trigger 214 must be in a fully un-actuated position. With trigger 214 in the fully un-actuated position, button 240 is moved from the first position to the second position (as described above) such that trigger 214 is prevented from actuation and such that slider 244 is free to move. With button 240 in the second position, slider 244 is moved from the first position to the second position (as described above). As slider 244 is moved to the second position, second stem 244b of slider 244 exerts a force on proximal radial flange 238d of inner shaft assembly 238 to urge inner shaft assembly 238, and in turn coupling member 238a thereof, proximally from a respective first position to a respective second position. As coupling member 238a is moved from the first position to the second position, ball detent 233 is free to drop or move radially inward of outer tube 231 as outer camming surface/relief $238c_1$ of coupling member 238 is moved into axial registration with ball detent 233. With ball detent 233 free to drop or move radially inward, end effector or SULU 300 may be fully coupled to distal support tube portion 232b of anchor retaining/advancing assembly 230.

Once again, as mentioned above, as so configured and operable, end effector or SULU 300 may only be removed and replaced when trigger 214 is in the fully un-actuated, home and locked position. As such, end effector or SULU 300 can not be removed or replaced or loaded while trigger 214 is in a short-stroked condition (i.e., partially actuated).

With a new end effector or SULU 300 fully coupled to distal support tube portion 232b of anchor retaining/advancing assembly 230, slider 244 is moved from the second position to the first position to secure or lock end effector or SULU 300 to distal support tube portion 232b of anchor retaining/advancing assembly 230. In particular, as slider 244 is moved to the first position, second stem 244b of slider 244 exerts a force on distal radial flange 238e of inner shaft assembly 238 to urge inner shaft assembly 238, and in turn coupling member 238a thereof, distally from second position to first position. As coupling member 238a is moved from the second position to the first position, ball detent 233 is urged by outer camming surface/relief $238c_1$ of coupling member 238 to move ball detent 233 radially outward. As ball detent 233 moves radially outward a portion of ball detent 233 enters an aperture 332c of end effector or SULU 300 to secure end effector or SULU 300 to distal support tube portion 232b of anchor retaining/advancing assembly 230. With end effector or SULU 300 coupled to distal support tube portion 232b of anchor retaining/advancing assembly 230, button 240 is moved from the second position to the first position (as described above) such that slider 244 is prevented from actuation and such that trigger 214 is free to move.

Turning now to FIGS. 5, 6, 15, 17-27, 32, 36, 37, 43, 44 and 46, end effector 300, in the form of a SULU or DLU, is shown and will be described herein. End effector 300, as mentioned above, is selectively connectable to distal tube portion 232b of outer support tube assembly 232.

Figure 19:
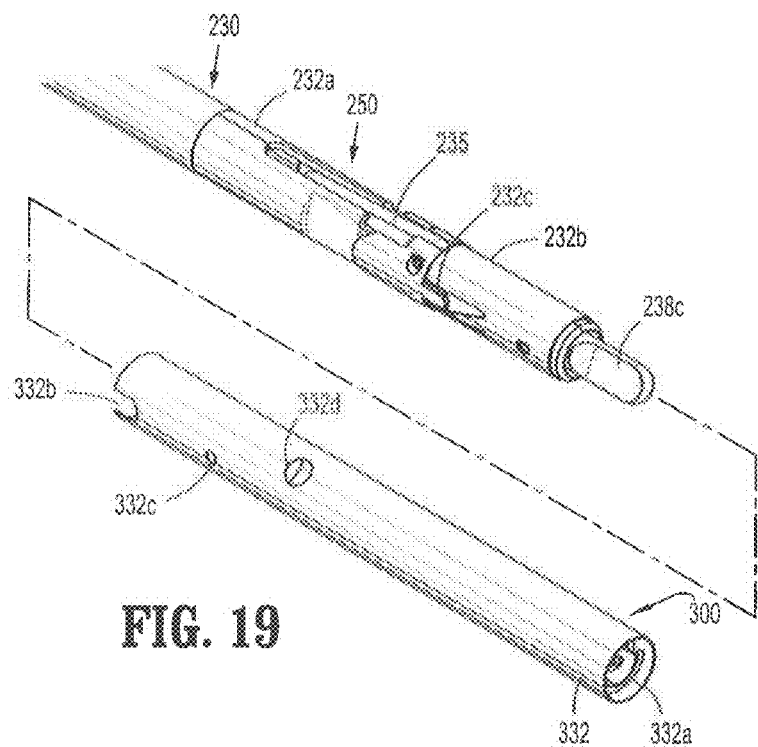
FIG. 19 is a perspective view of the distal end of the endoscopic surgical device of FIG. 5 with an end effector shown separated therefrom.
Figure 20:
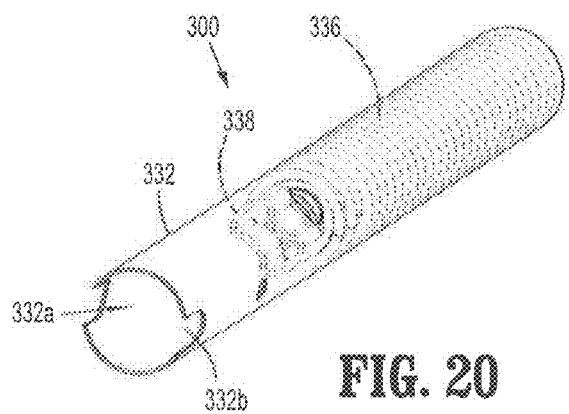
FIG. 20 is a rear perspective view of the end effector of FIG. 19.
Figure 21:
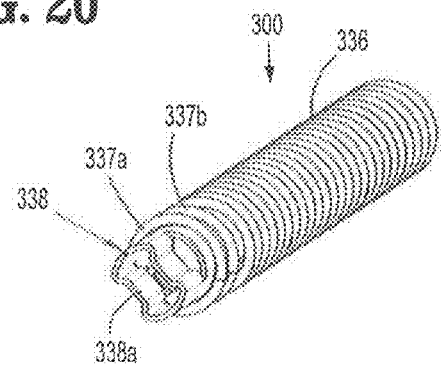
FIG. 21 is a rear perspective view of the end effector of FIG. 20, with an outer tube removed therefrom.

End effector or SULU 300 includes an outer tube 332 defining a lumen 332a therethrough and being configured and dimensioned (i.e., substantially rectangular or dog bone shaped) to receive distal tube portion 232b of outer support tube assembly 232 and coupling member 238c of anchor retaining/advancing assembly 230 therein. As seen in FIG. 19, outer tube 332 defines a proximal key slot 332b for engagement with a key 232c formed in distal tube portion 232b of outer support tube assembly 232. In use, when end effector or SULU 300 is connected to distal tube portion 232b of outer support tube assembly 232 key slot 332b and key 232c engage with one another to properly align end effector or SULU 300 and anchor retaining/advancing assembly 230 to one another.

End effector or SULU 300 further includes a spiral or coil 336 fixedly disposed within a distal portion of outer tube 332. A pair of axially spaced apart retention rings 337a, 337b is also fixedly disposed within outer tube 332 at a location proximal of coil 336.

End effector or SULU 300 also includes an inner tube 338 rotatably disposed within coil 336. Inner tube 338 defines a lumen therethrough, and includes a proximal end portion 338a and a splined distal end portion 338b. Proximal end portion 338a of inner tube 338 is configured and dimensioned to slidably receive coupling member 238c of anchor retaining/advancing assembly 230 therein. Inner tube 338 includes a plurality of retention tabs 338c projecting radially outward therefrom and which snap beyond one of the pair of retention rings 337a, 337b, when inner tube 338 is assembled with outer tube 332. In this manner, outer tube 332 and inner tube 338 are axially fixed and yet rotatable relative to one another.

Distal end portion 338a of inner tube 338 is slotted, defining a pair of tines $338a_1$ and a pair of channels $338a_2$. Distal end portion 338a of inner tube 338 is capable of accepting a plurality of anchors 100 within inner tube 338. In particular, anchors 100 are loaded into end effector or SULU 300 such that the pair of opposing threaded sections 112a, 112b of anchors 100 extend through respective channels $338a_2$ of distal end portion 338a of inner tube 338 and are slidably disposed within the grove of coil 336, and the pair of tines $338a_1$ of distal end portion 338a of inner tube 338 are disposed within the pair of slotted sections or opposed radial recesses 116a, 116b of anchors 100. Each anchor 100 is loaded into end effector or SULU 300 such that adjacent anchors 100 are not in contact with one another so as to not damage distal tips 136.

In use, as inner tube 338 is rotated, about its longitudinal axis, with respect to coil 336, the pair of tines $338a_1$ of inner tube 338 transmit the rotation to anchors 100 and advance anchors 100 distally owing to head threads 114a, 114b of anchors 100 engaging with coil 336.

Figure 49:
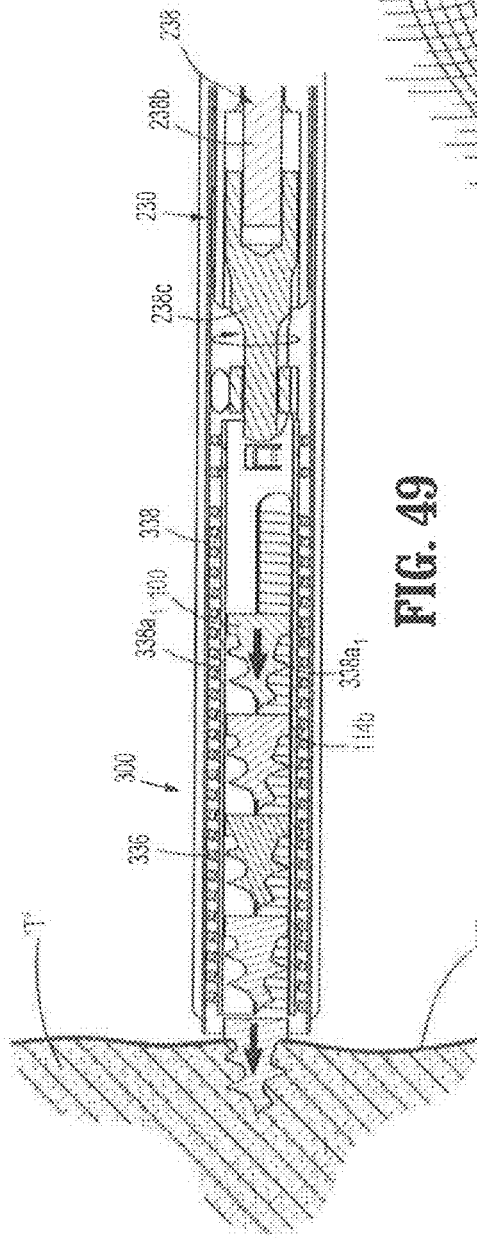
FIG. 49 is a longitudinal, cross-sectional view of the end effector and a distal end of endoscopic assembly, illustrating an implanting of a surgical anchor through a surgical mesh and into underlying tissue.
Figure 50:
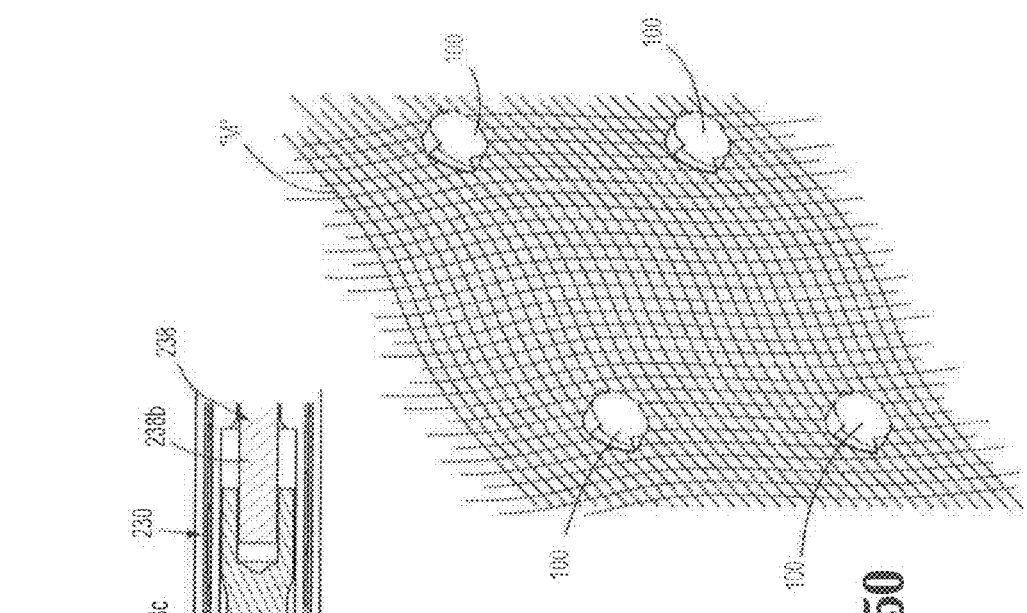
FIG. 50 is a perspective illustration showing the anchoring and/or fixation of a surgical mesh to underlying tissue with a plurality of surgical fasteners.

In an operation of surgical tacker 200, as seen in FIG. 49, with end effector or SULU 300 operatively connected to distal tube portion 232b of outer support tube assembly 232 of anchor retaining/advancing assembly 230, as inner shaft assembly 238 is rotated due to an actuation of trigger 214, as described above, said rotation is transmitted to inner tube 338 of end effector or SULU 300 via coupling member 238c of anchor retaining/advancing assembly 230. Again, as inner tube 338 is rotated, about its longitudinal axis, with respect to coil 336, the pair of tines $338a_1$ of inner tube 338 transmit the rotation to the entire stack of anchors 100 and advance the entire stack of anchors 100 distally, owing to head threads 114a, 114b of anchors 100 engaging with coil 336.

In accordance with the present disclosure, the components of surgical tacker 200, and anchors 100 are dimensioned such that a single complete and full actuation of trigger 214 results in a firing of a singe anchor 100 (i.e., the distal-most anchor of the stack of anchors 100 loaded in end effector or SULU 300) from end effector or SULU 300.

Surgical tacker 200 may be repeatedly fired to fire anchors from end effector 300 until the surgical procedure is complete or until end effector or SULU 300 is spent of anchors 100. If end effector or SULU 300 is spent of anchors 100, and if additional anchors 100 are required to complete the surgical procedure, spent end effector or SULU 300 may be replaced with a new (i.e., loaded with anchors 100) end effector or SULU 300.

As seen in FIGS. 40-44, in order to replace spent end effector or SULU 300 with a new end effector or SULU 300, with trigger 214 in the fully un-actuated position (as described above, the surgeon actuates or slides button 244 to release the spent end effector or SULU 300, decouples end effector or SULU 300 from anchor retaining/advancing assembly 230, loads or connects a new end effector or SULU 300 to anchor retaining/advancing assembly 230 (by fitting proximal end portion 338a of inner tube 338 over coupling member 238c of anchor retaining/advancing assembly 230), and releases button 244 to retain the new end effector or SULU 300 on anchor retaining/advancing assembly 230. Since trigger 214 is in the fully un-actuated position with the loading of a new end effector or SULU 300, timing system 270 is reset such that each fully actuation of trigger 214 results in the firing of a single anchor 100.

It is contemplated that end effector or SULU 300 may only be connected or coupled to distal tube portion 232b of outer support tube assembly 232 of anchor retaining/advancing assembly 230 while anchor retaining/advancing assembly 230 is in the non-articulated condition.

In accordance with the present disclosure, with end effector or SULU 300 connected or coupled to distal tube portion 232b of outer support tube assembly 232 of anchor retaining/advancing assembly 230, articulation knob 246 is rotated or held in place such that anchor retaining/advancing assembly 230 is in a non-articulated condition.

Additionally, in accordance with the present disclosure, with end effector or SULU 300 connected or coupled to distal tube portion 232b of outer support tube assembly 232 of anchor retaining/advancing assembly 230, end effector or SULU 300 is introduced into a target surgical site while in the non-articulated condition. With end effector or SULU 300 disposed within the target surgical site, the surgeon may remotely articulate end effector or SULU 300 relative to anchor retaining/advancing assembly 230. Specifically, as seen in FIGS. 45 and 46, the surgeon rotates articulation knob 246 to axially displace connection nut 247 and proximal tube portion 234a of inner articulation tube assembly 234 to move in the proximal axial direction. As proximal tube portion 234a is moved in the proximal axial direction, proximal tube portion 234a acts or pulls on articulation link 235 to cause articulation link 235 to translate in a proximal direction. As articulation link 235 is axially translated in a proximal direction, articulation link 235 acts or pulls on distal tube portion 232b of outer support tube assembly 232 to cause distal tube portion 232b to pivot about a pivot axis of pivot pin 232c. As distal tube portion 232b is pivoted, distal tube portion 232b causes end effector 300 to be moved to an articulated orientation relative to the central longitudinal axis of anchor retaining/advancing assembly 230.

Figure 28:
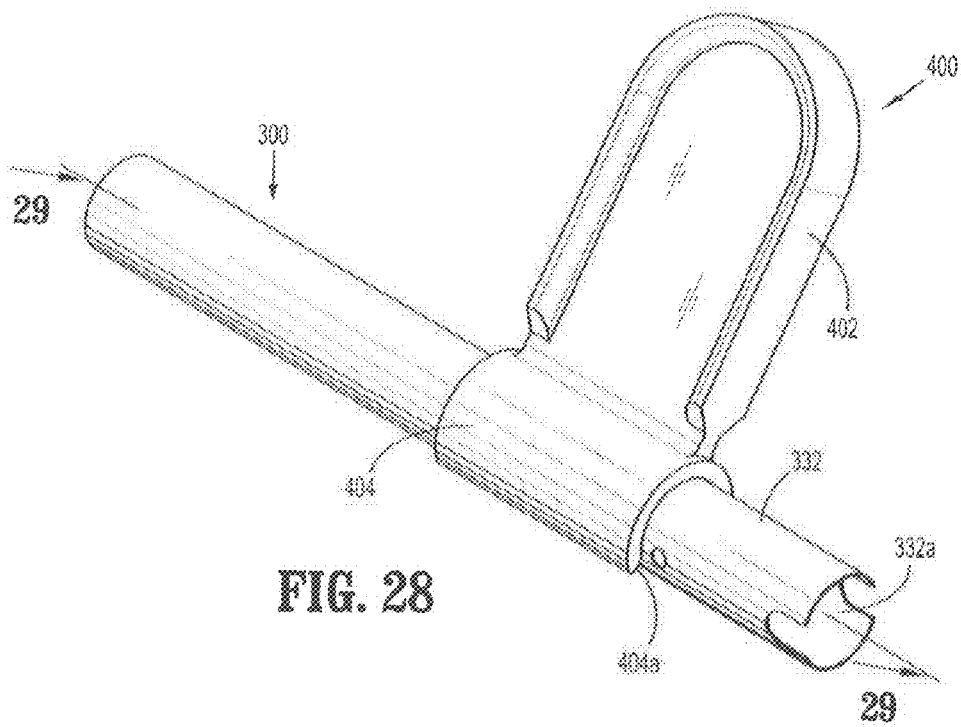
FIG. 28 is a perspective view of the end effector of FIGS. 20-27 with a shipping wedge shown attached thereto.
Figure 29:
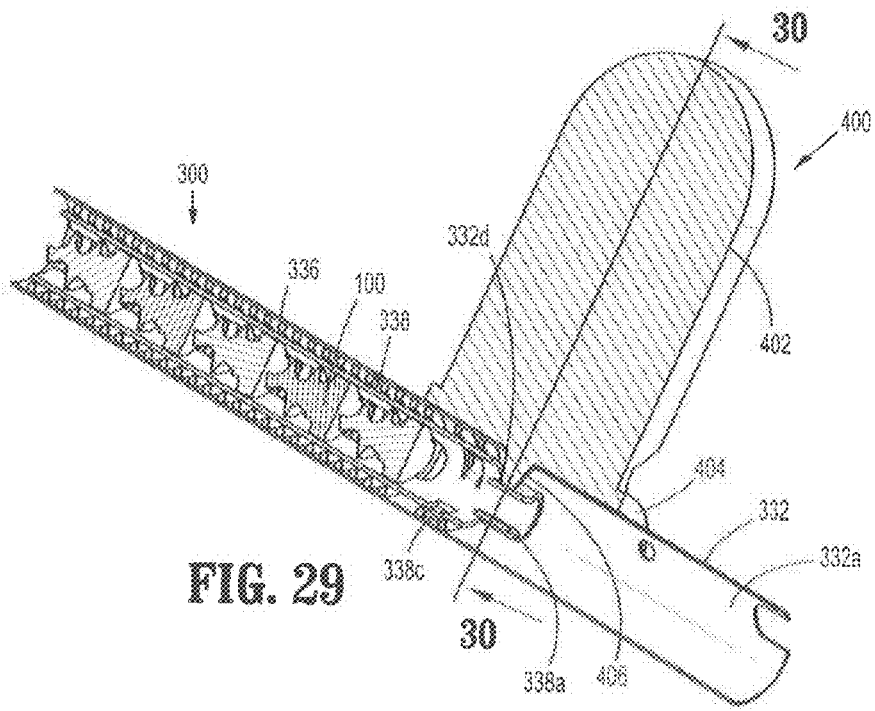
FIG. 29 is a cross-sectional view as taken through 29-29 of FIG. 28.
Figure 34:
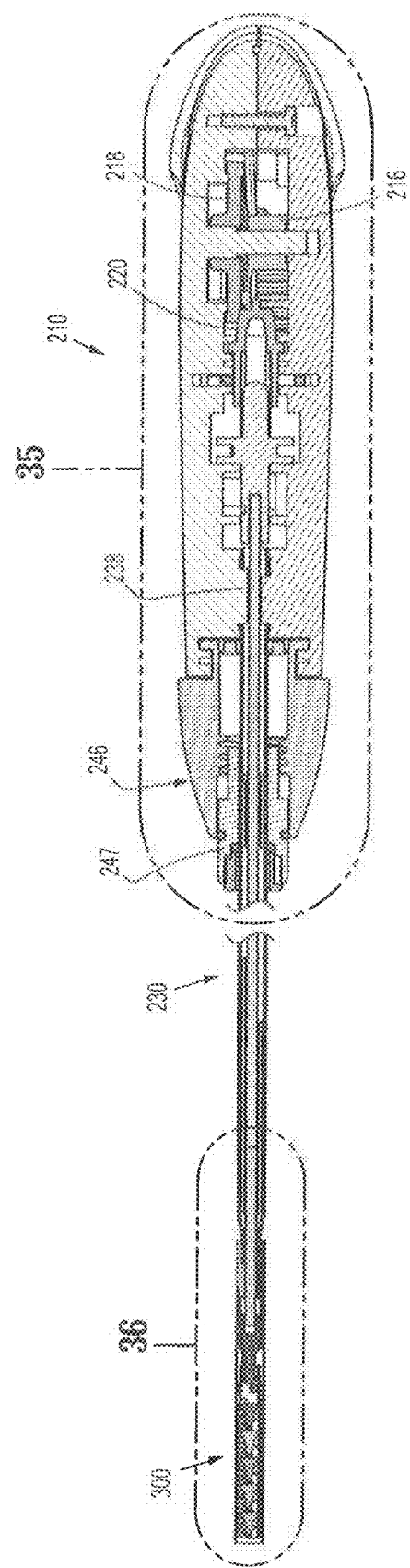
FIG. 34 is a cross-sectional view as taken though 34-34 of FIG. 31.
Figure 35:
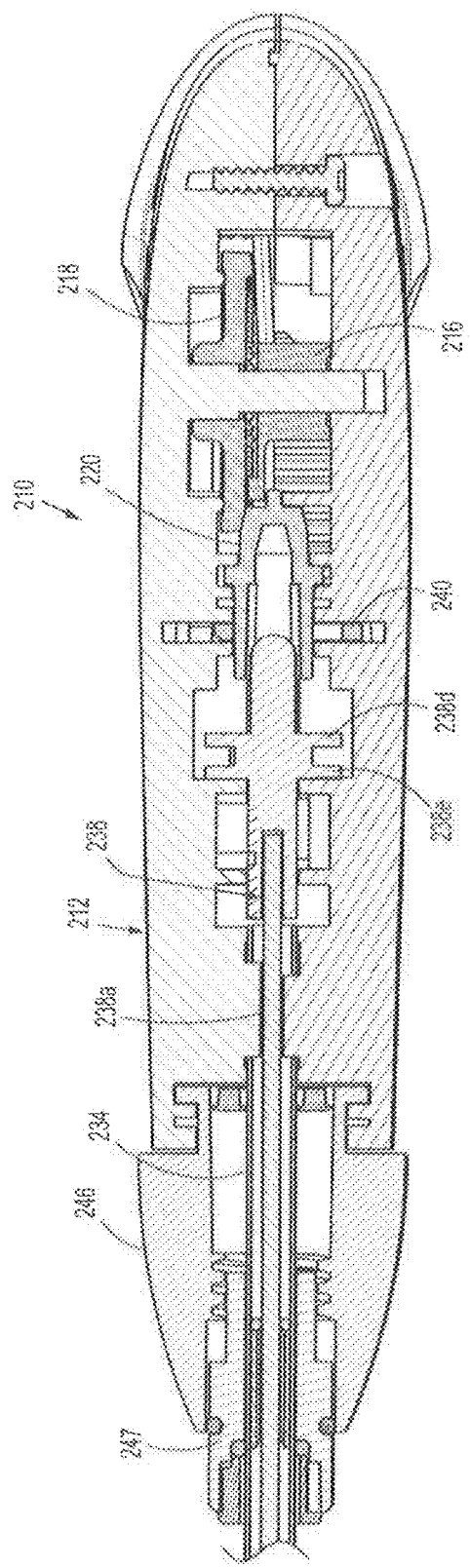
FIG. 35 is an enlarged view of the indicated area of detail of FIG. 34.
Figures 38, 39:
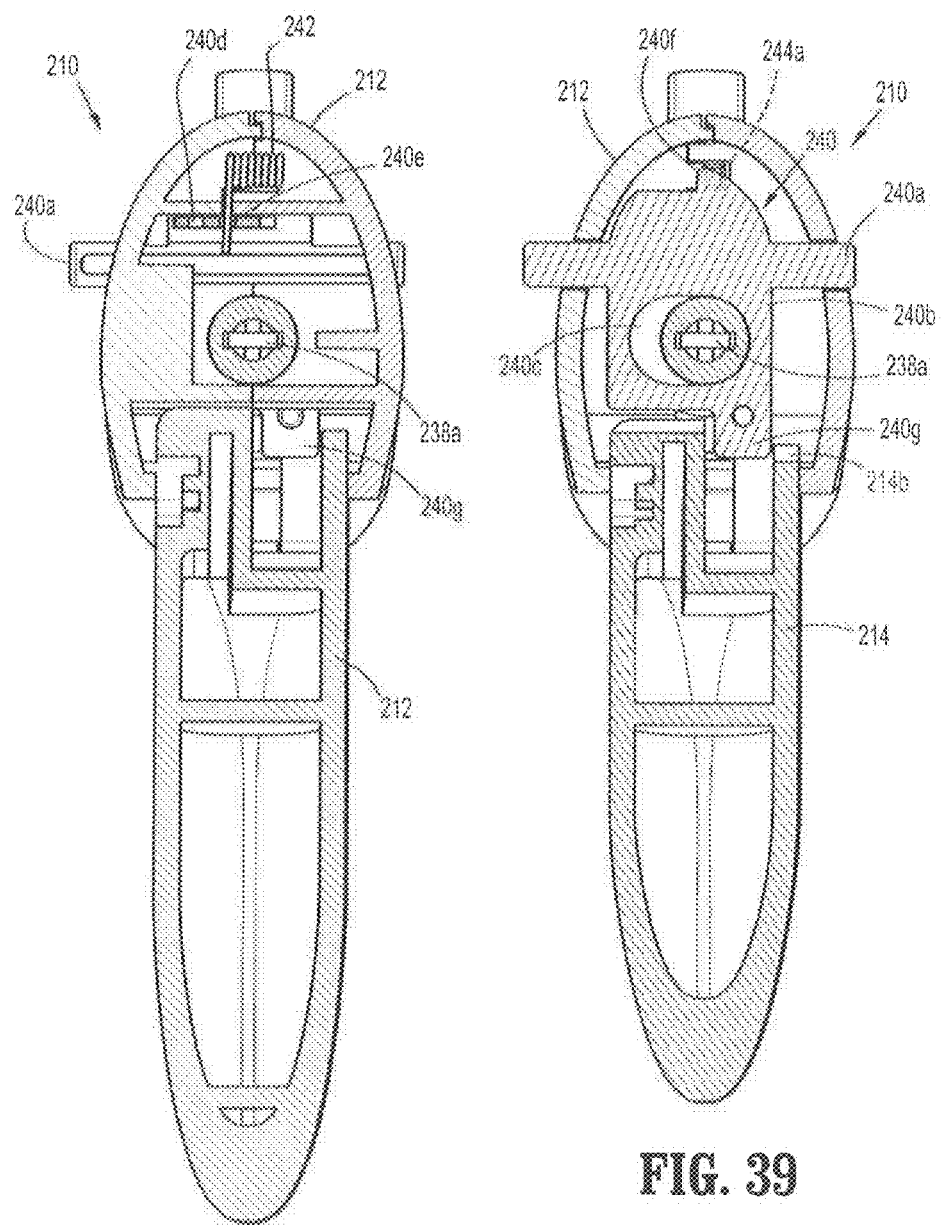
FIG. 38 is a cross-sectional view as taken though 34-34 of FIG. 33.
FIG. 39 is a cross-sectional view as taken though 34-34 of FIG. 33.

Turning now to FIGS. 28-30, in accordance with the present disclosure, a shipping wedge 400 may be provided which is configured and dimensioned to releasably connect to end effector or SULU 300, to inhibit premature rotation of inner tube 338 of end effector or SULU 300, and to help facilitate loading/unloading of end effector or SULU 300 to/from distal tube portion 232b of anchor retaining/advancing assembly 230.

Shipping wedge 400 includes a handle portion 402 and a coupling member 404 integrally formed with or secured to handle portion 402. Coupling member 404 is substantially tubular having a substantially C-shaped transverse cross-sectional profile. Coupling member 404 defines a longitudinally extending opening or gap 404a therealong. Handle portion 404 defines a longitudinal axis that is substantially orthogonal to the longitudinal axis of coupling member 404.

Coupling member 404 has a diameter sufficient to accommodate end effector or SULU 300 therein and along. Also, gap 404a of coupling member 404 has a dimension, which together with the materials of construction of at least coupling member 404, allows for coupling member 404 to be snapped-over end effector or SULU 300. It is envisioned that at least coupling member 404 may be fabricated from a polymeric or other substantially rigid and resilient material.

As seen in FIGS. 29 and 30, shipping wedge 400 includes a wedge, spike or nub 406 extending radially into coupling member 404. In particular, wedge 406 extends or projects in a direction substantially parallel to the longitudinal axis of handle portion 402. Wedge 406 has a length sufficient such that, when shipping wedge 400 is attached to end effector or SULU 300, wedge 406 enters an aperture 332d (see FIGS. 19, 22, 29 and 30) formed in outer tube 332 of end effector or SULU 300.

Additionally, when shipping wedge 400 is attached to end effector or SULU 300, wedge 406 extends to be in close proximity to or in contact with proximal end portion 338a of inner tube 338 of end effector or SULU 300. By extending this amount, wedge 406 inhibits rotation of inner tube 338 relative to outer tube 332 by blocking or contacting proximal end portion 338a of inner tube 338 if inner tube 338 experiences any rotation relative to outer tube 332.

Also, when shipping wedge 400 is attached to end effector or SULU 300, and with wedge 406 blocking rotation of inner tube 338 of end effector or SULU 300, shipping wedge 400 facilitates a loading/unloading of end effector or SULU 300 to/from distal tube portion 232b of anchor retaining/advancing assembly 230. During loading of end effector or SULU 300 to distal tube portion 232b of anchor retaining/advancing assembly 230, shipping wedge 400 functions to fix an angular orientation of proximal end portion 338a of inner tube 338 for proper alignment and orientation with coupling member 238c of anchor retaining/advancing assembly 230.

In accordance with the present disclosure, it is contemplated that handle assembly 100 may be replaced by an electromechanical control module configured and adapted to drive the flexible drive cables to fire or actuate the surgical device. The electromechanical control module may include at least one microprocessor, at least one drive motor controllable by the at least one microprocessor, and a source of power for energizing the at least one microprocessor and the at least one drive motor.

Turning now to FIGS. 51-55, another embodiment of an endoscopic surgical device, in the form of an endoscopic surgical tack applier or tacker, is shown generally as 500. Endoscopic surgical device 500 is similar to endoscopic surgical device 200 and is only described herein to the extent necessary to describe the differences in construction and operation thereof. Likewise, another embodiment of an end effector is shown generally as 520. End effector 520 is similar to end effector 300 and is only described herein to the extent necessary to describe the differences in construction and operation thereof.

Figure 51:
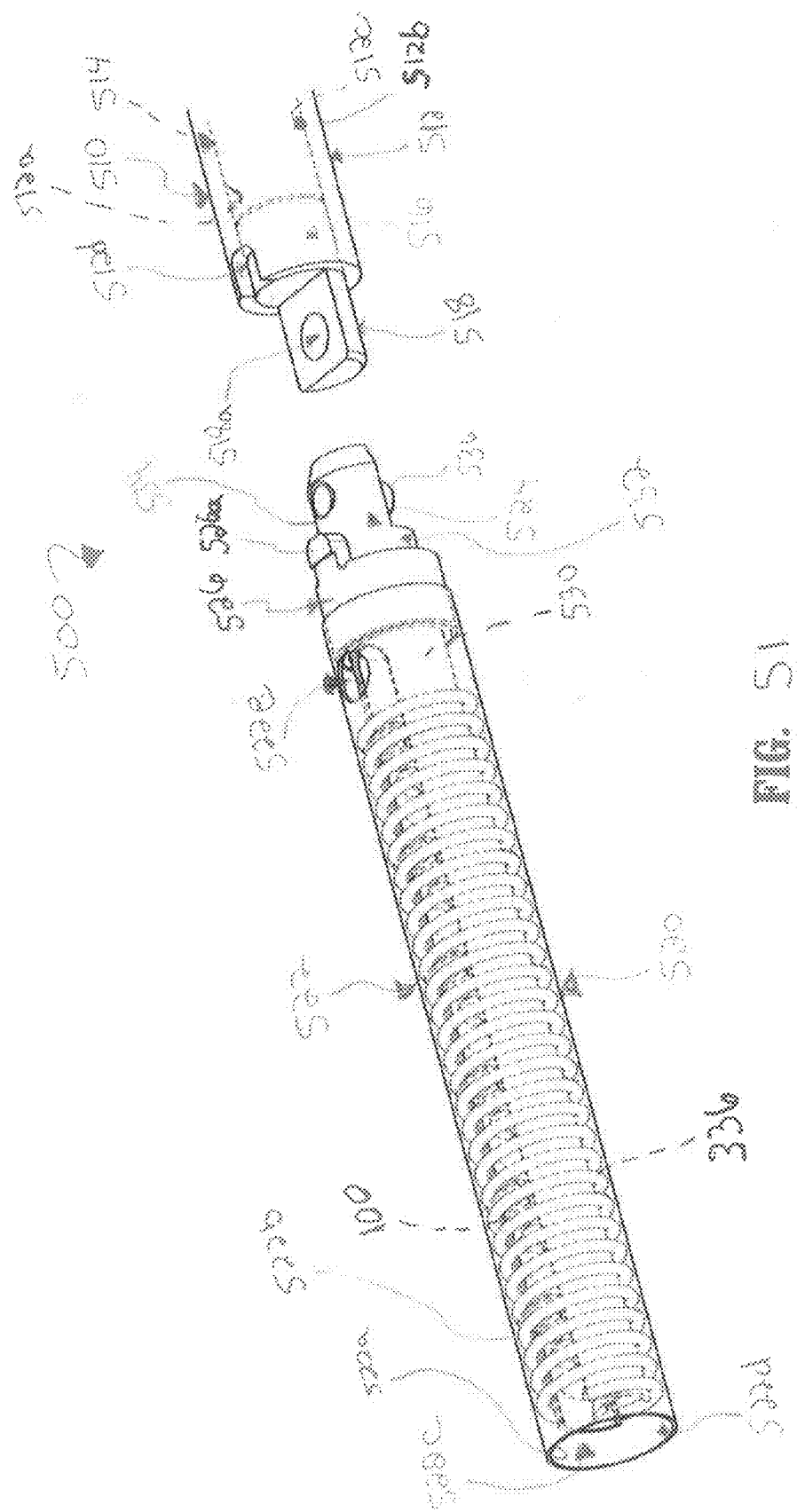
FIG. 51 is a perspective view of a distal end of another embodiment of an endoscopic surgical device illustrating an alternate end effector and an alternate complementary elongate body portion, wherein the end effector is shown separated from the elongate body portion.

With reference to FIG. 51, endoscopic surgical device 500 includes an elongate body portion 510 and an end effector 520 (e.g., single use loading unit) that can be selectively secured to a distal end of elongate body portion 510.

Elongate body portion 510 includes an outer tube 512 and an inner actuation shaft 514 that is slidably positioned within outer tube 512. Outer tube 512 includes an inner surface 512a and an outer surface 512b. Inner surface 512a defines a lumen 512c that extends longitudinally through outer tube 512 and supports inner actuation shaft 514. Outer tube 512 defines a notch 512d that extends between and across inner surface 512a and outer surface 512b in a distal end of outer tube 512. Inner actuation shaft 514 extends longitudinally through lumen 512c between proximal and distal ends of outer tube 512. The distal end of inner actuation shaft 514 includes an engagement member 516. An arm or tab 518 extends from engagement member 516. Arm 518 defines a recess 518a that extends at least partially therethrough.

Figure 52:
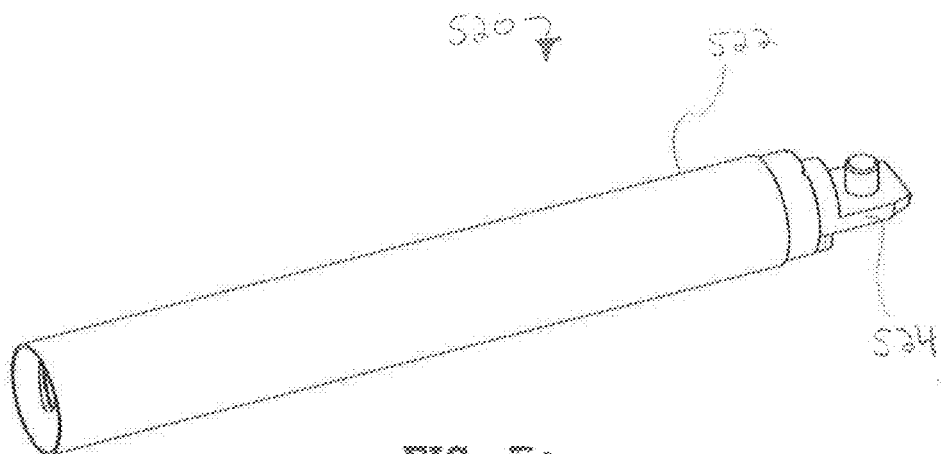
FIG. 52 is a perspective view of the end effector of the endoscopic surgical device of FIG. 51.
Figure 53:
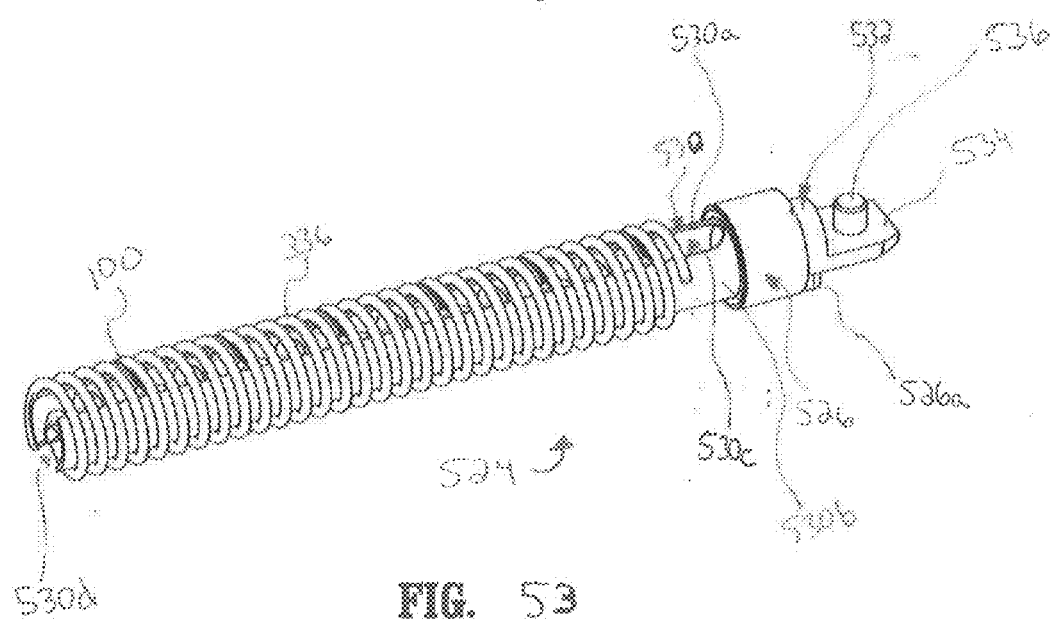
FIG. 53 is a perspective view of the end effector of FIG. 52 with an outer tube of the end effector removed therefrom.

As illustrated in FIGS. 51-53, end effector 520 includes an outer tube 522 and a splined inner tube 524 rotatably positioned within outer tube 522. Outer tube 522 includes an inner surface 522a and an outer surface 522b Inner surface 522a defines a lumen 522c that extends longitudinally through outer tube 522 between proximal and distal ends of outer tube 522. The distal end of outer tube 522 includes a distal opening 522d. Outer tube 522 defines an opening 522e that extends between inner surface 522a and outer surface 522b in a proximal portion of outer tube 522. Splined inner tube 524 supports a spiral 336 that is fixedly disposed within a distal portion of outer tube 522 and about a pair of tines 530 of the splined inner tube 524, so that the pair of tines 530 and spiral 336 support a plurality of surgical anchors 100 that are adapted for selective advancement through end effector 520.

As can be seen in FIG. 53, splined inner tube 524 includes a coupling member 526 fixedly secured to inner surface 522a of outer tube 522 at a proximal end thereof and includes a locking tab 526a that extends from a proximal end of coupling member 526. As described above, splined inner tube 524 includes a pair of tines 530 at a distal end thereof and an engagement member 532 at a proximal end thereof. The pair of tines 530 includes a first tine 530a and a second tine 530b. First and second tines 530a, 530b are spaced apart and define first and second channels 530c, 530d therebetween that receive a portion of each of the plurality of anchors 100. Engagement member 532 includes an arm or tab 534 extending longitudinally therefrom, and a pin 536 projecting perpendicularly to arm 534.

Figure 54:
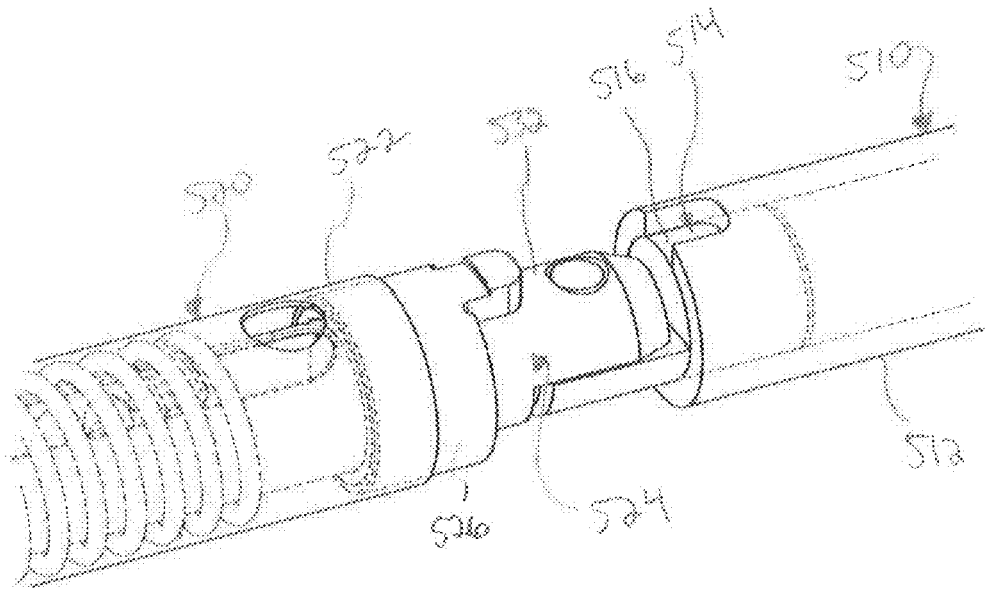
FIG. 54 is a perspective view of a portion of the endoscopic surgical device of FIG. 51 with a proximal end of the end effector shown connected to a distal end of the elongate body portion, the elongate body portion shown in an advanced position.
Figure 55:
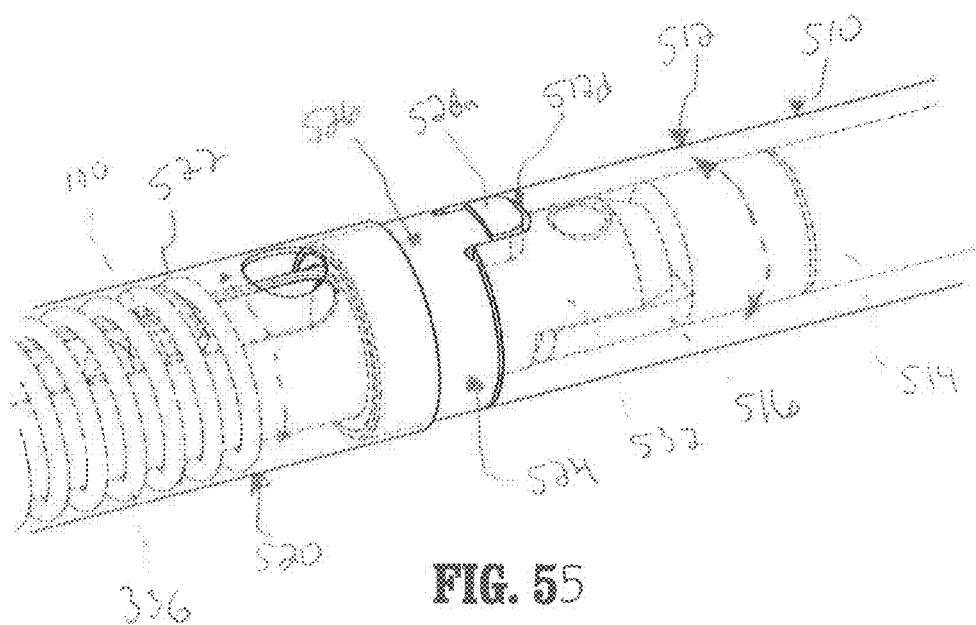
FIG. 55 is a perspective view of a portion of the endoscopic surgical device of FIG. 51 with the proximal end of the end effector shown connected to the distal end of the elongate body portion, the elongate body portion shown in a retracted position.

In use, as shown in FIGS. 54 and 55, inner actuation shaft 514 of elongate body portion 510 is slidably movable relative to outer tube 512 between an advanced position (FIG. 54) and a retracted position (FIG. 55). In the advanced position, engagement member 516 of inner actuation shaft 514 is exposed or projects from outer tube 512. In the retracted position, engagement member 516 of inner actuation shaft 514 is concealed or housed within outer tube 512. More particularly, in the advanced position, arm 518 of engagement member 516 is extended such that recess 518a is exposed for receiving pin 536 of engagement member 532.

To connect end effector 520 to elongate body portion 510, pin 536 of engagement member 532 is inserted in recess 518a of engagement member 516 so that arm 534 of engagement member 532 is connected to arm 518 of engagement member 516. After connecting end effector 520 to elongate body portion 510, inner actuation shaft 514 can be moved to the retracted position which draws both engagement members 532, 516 within outer tube 512 of elongate body portion 510. As such, locking tab 526a of end effector 520 is received within notch 512d of elongate body portion 510 to prevent outer tube 522 of end effector 520 from rotating relative to elongate body portion 510 upon a rotation of inner actuation shaft 514. Additionally, engagement member 516, 532 are housed within outer tube 522 of end effector 520, thereby being inhibited from separating from one another.

A rotation of inner actuation shaft 114 rotates both engagement members 516, 532 relative to outer tubes 512, 522 and coupling member 526 to impart rotation to splined inner tube 524, and in turn, the pair of tines 530, for distally advancing the plurality of anchors 100 along spiral 336 and individually deploying each of the plurality of anchors 100 out of distal opening 522d of outer tube 522 of end effector 520.

Figure 56:
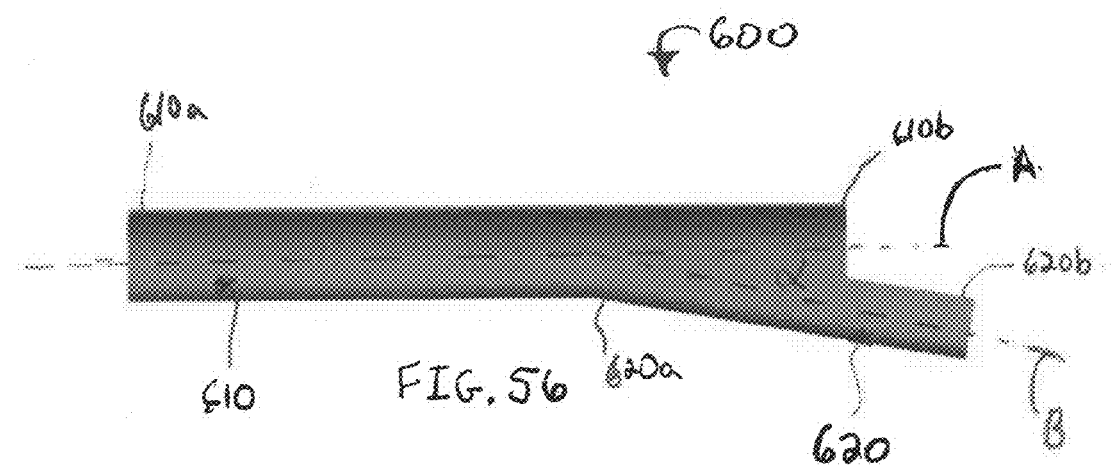
FIG. 56 is a side, elevational view of an embodiment of a shipping wedge in accordance with the present disclosure.

Turning now to FIG. 56, another embodiment of a shipping wedge is shown generally as 600. Shipping wedge 600 includes an elongate first body 610, and an angled second body 620 that extends from first body 610 at an angle relative to first body 610. More particularly, first body 610 defines a longitudinal axis "A" that extends through opposed ends 610a, 610b of elongate body 610. Angled body 620 defines a longitudinal axis "B" that extends through opposed ends of 620a, 620b of angled body 620. Longitudinal axes "A" and "B" define an angle "a" therebetween. Although shown in FIG. 56 as an acute angle, angle "a" can be any suitable angle.

Figure 57A:
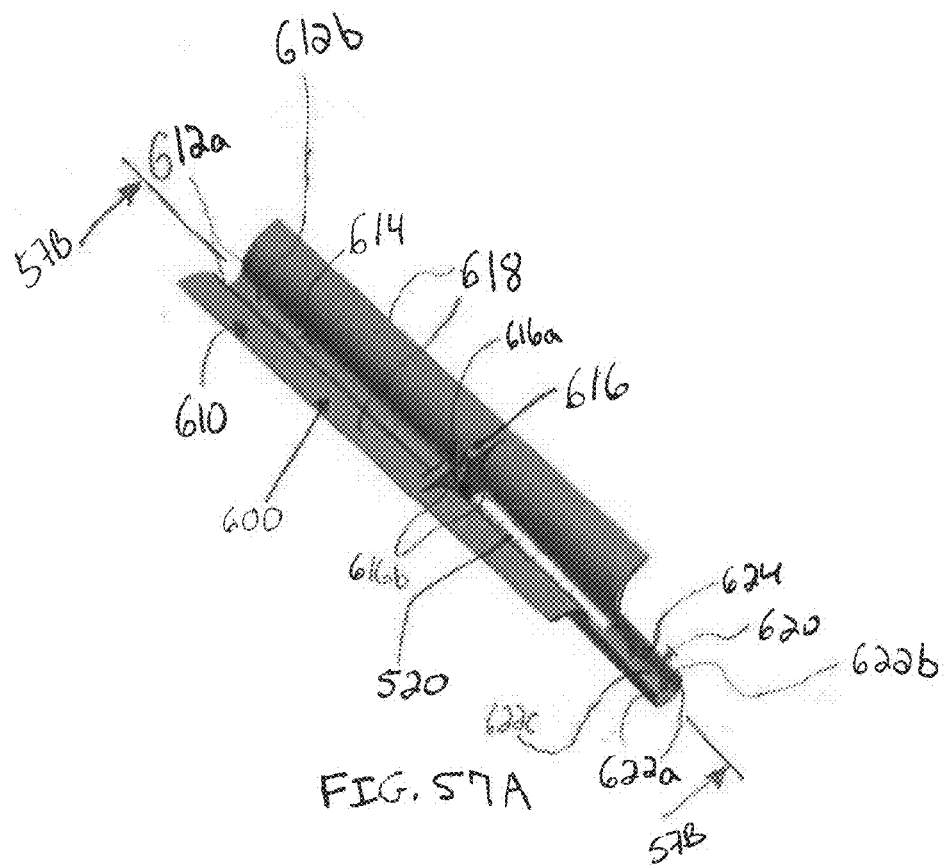
FIG. 57A is a top, perspective view of the shipping wedge of FIG. 56 with the end effector of FIG. 52 shown disposed within and coupled to the shipping wedge.
Figure 57B:
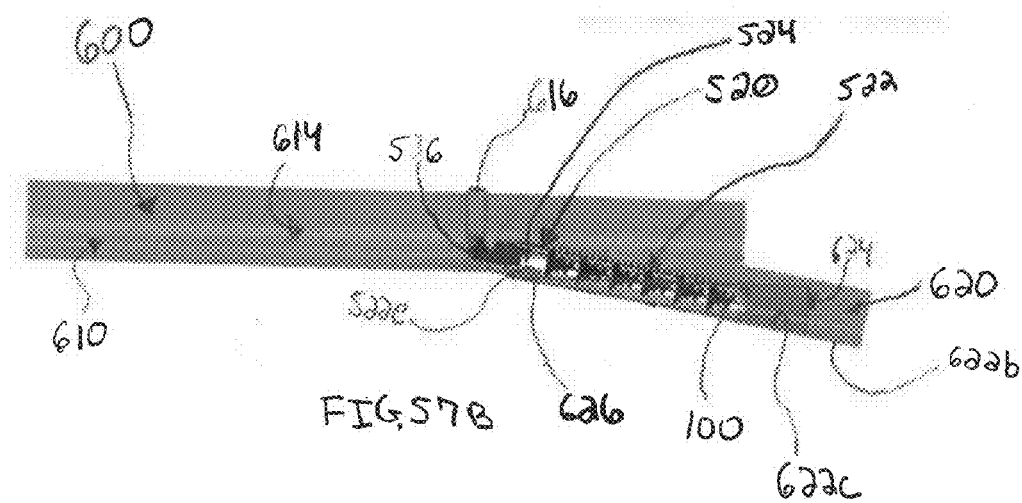
FIG. 57B is a side, cross-sectional view as taken along 57B-57B of FIG. 57A.
Figure 58A:
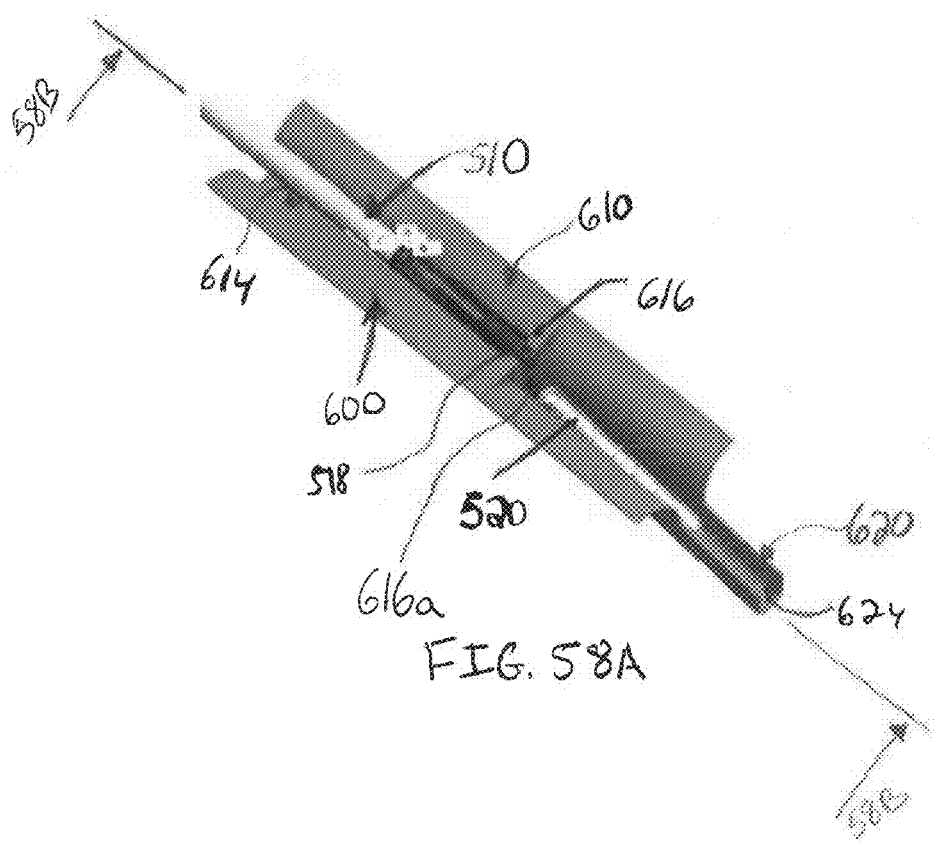
FIG. 58A is a top, perspective view of the shipping wedge of FIG. 56 with the end effector of FIG. 52 shown coupled to the shipping wedge and with the elongate body portion of the endoscopic surgical device of FIG. 51 being positioned within the shipping wedge relative to the end effector.
Figure 58B:
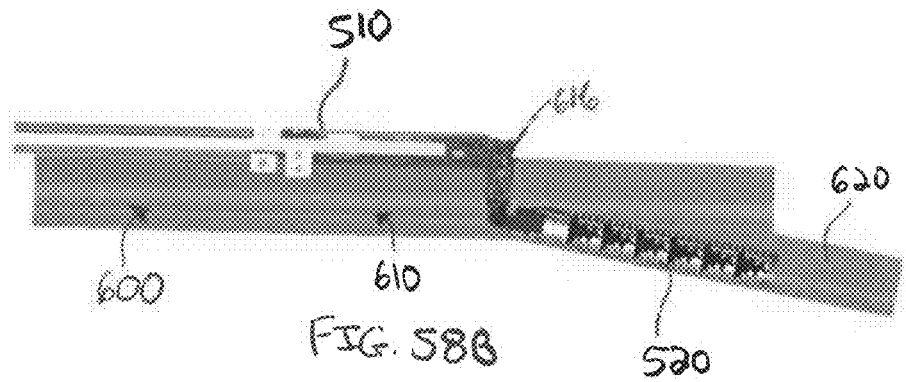
FIG. 58B is a side, cross-sectional view as taken along 58B-58B of FIG. 58A.

Referring to FIGS. 57A and 57B, first body 610 includes a pair of opposed sidewalls 612a that is connected at a base 612b. The pair of opposed sidewalls 612a defines a channel 614 therebetween to form a U-shape that is dimensioned to receive an elongate body such as elongate body portion 510 of endoscopic surgical device 500. Channel 614 extends longitudinally through first body 610. An alignment rib 616 extends between the pair of opposed sidewalls 612a and defines a passage 616a that extends through alignment rib 616 and separates alignment rib 616 into a pair of segments 616b.

Angled body 620 includes a pair of opposed sidewalls 622a that is connected at a base 622b. The pair of opposed sidewalls 622a defines a channel 624 therebetween to form a U-shape that is dimensioned to receive and retain an end effector, such as, end effector 520 (FIGS. 57A and 57B). Channel 624 extends longitudinally through angled body 620 such that channel 624 is angled relative to channel 614 (see FIG. 57B). Angled body 620 includes a protuberance 626 (e.g., a boss or nub) that extends from an inner surface 622c of base 622b. Protuberance 626 can have any suitable shape including circular and non-circular (e.g., elliptical, polygonal, etc.) shapes.

A pair of alignment flanges 618 extend from opposed sidewalls 612a of first body 610 and opposed sidewalls 622a of angled body 620 to form funnel configurations that facilitate proper alignment of an endoscopic surgical device such as endoscopic surgical device 500, or portions thereof, relative to shipping wedge 600. As shown in FIG. 57A, each alignment flange of the pair of alignment flanges 618 has a curvilinear arrangement that extends outwardly from channels 614 and 624.

With continued reference to FIGS. 57A and 57B, although shipping wedge 600 can be used with any suitable endoscopic surgical device, in an exemplary use with endoscopic surgical device 500, end effector 520 of endoscopic surgical device 500 is secured within channel 624 of angled body 620 (e.g., press fit). Protuberance 626 of angled body 620 is positioned within opening 522e of end effector 520 (and/or within first and/or second channels 530c, 530d of end effector 520) to prevent end effector 520 from translating through channel 624 of angled body 620 and/or to prevent end effector 520, or portions thereof (e.g., outer and/or inner tube 522, 524 including the pair of tines 530), from rotating within channel 624 of angled body 620. As can be appreciated, the protuberance 626 enables end effector 520 to maintain proper timing (e.g., tack/anchor deployment timing) during shipment and/or loading processes of end effector 520. When the end effector 520 is secured within channel 624 of angled body 620, pin 536 of end effector 520 is aligned with alignment rib 616.

Figure 59:
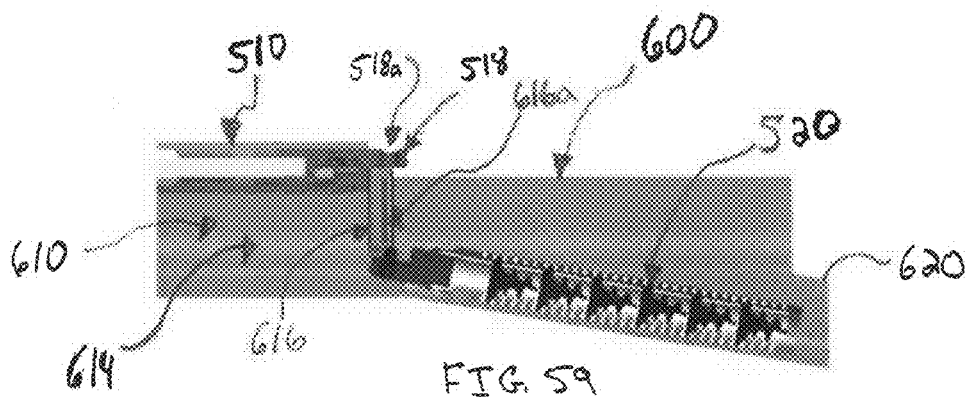
FIGS. 59-62 are enlarged, progressive, side, cross-sectional views illustrating the end effector being coupled and secured to the elongate body portion and removed from the shipping wedge.
Figure 60:
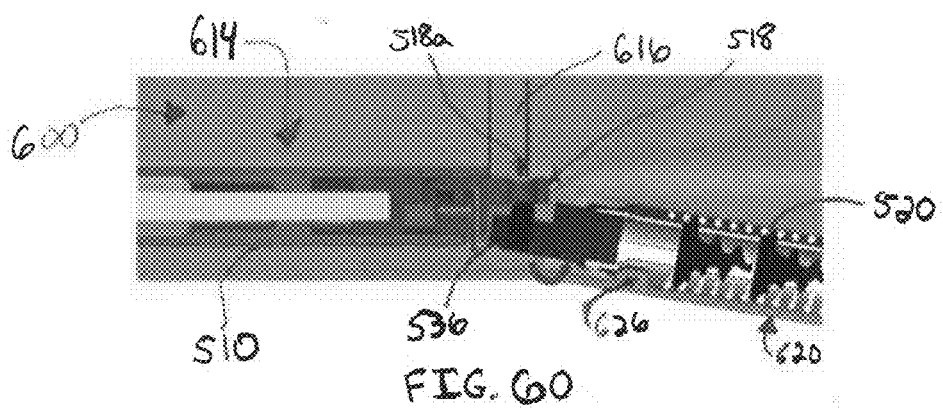
Figure 61:
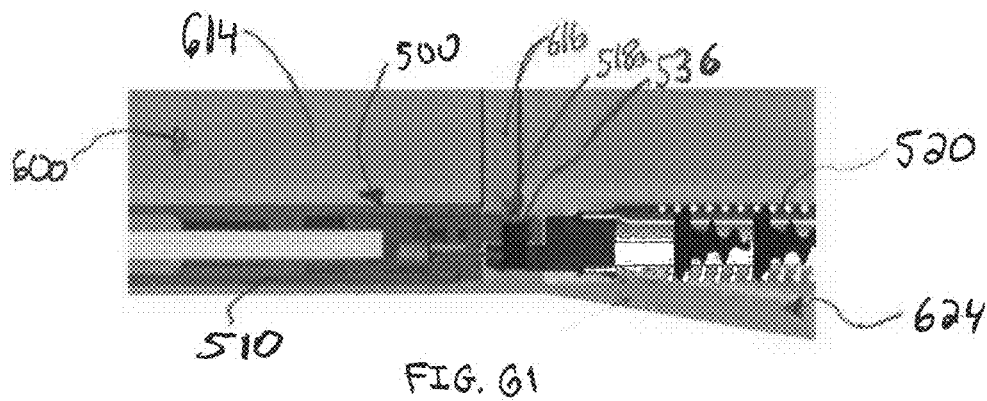

Referring also to FIGS. 58A-62, to remove end effector 520 from shipping wedge 600, in the advanced position of the elongate body portion 510 of endoscopic surgical device 500, elongate body portion 510 can be positioned relative to channel 614 so that the distal end of elongate body portion 510 is longitudinally aligned with alignment rib 616. More particularly, engagement member 516 of elongate body portion 510 abuts against alignment rib 616 of shipping wedge 600 to longitudinally align arm 518 of engagement member 516 with passage 616a. Elongate body portion 510 is then inserted (e.g., press fit) into channel 614 so that arm 518 of elongate body portion 510, guided by alignment rib 616 of shipping wedge 600, moves through passage 616a toward pin 536 of end effector 520 (FIGS. 59 and 60). As elongate body portion 510 engages end effector 520, pin 536 inserts into recess 518a of arm 518 so that end effector 520 pivots relative to elongate body portion 510 and out of channel 624 of angled body 620 into axial alignment with elongate body portion 510 (FIGS. 60 and 61). As end effector 520 pivots out of channel 624 of angled body 620, protuberance 626 of angled body 620 separates from opening 522e of end effector 520.

Figure 62:
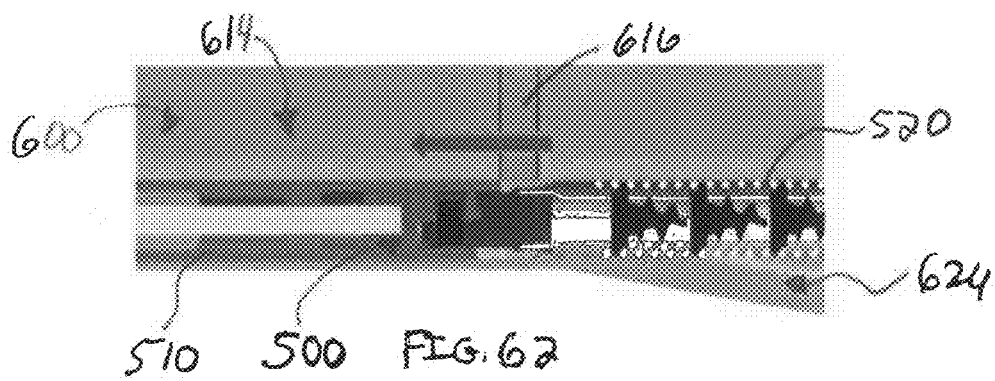

As seen in FIG. 62, with elongate body portion 510 connected to end effector 520, elongate body portion 510 can be moved to the retracted position to draw end effector 520 into engagement with elongate body portion 510 to secure the proximal end of end effector 520 within the distal end of elongate body portion 510. Endoscopic surgical device 500, including both elongate body portion 510 and end effector 520, can then be withdrawn from shipping wedge 600, while beneath alignment rib 616, and through channel 614 of shipping wedge 600 to separate endoscopic surgical device 500 from shipping wedge 600 (FIG. 62). Endoscopic surgical device 500 can then be used to perform a surgical procedure.

As can be appreciated, securement of any of the components of the presently disclosed devices can be effectuated using known fastening techniques such welding, crimping, gluing, etc.

It will be understood that various modifications may be made to the embodiments disclosed herein. For example, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of various embodiments. Those skilled in the art will envision other modifications within the scope and spirit of the claims appended thereto.

What is claimed is:

1. An endoscopic surgical device, comprising;
    an elongate body portion including an outer tube and an inner actuation shaft, the inner actuation shaft being movably positioned within the outer tube and repositionable between a retracted position and an advanced position, the inner actuation shaft including an engagement member that is concealed within the outer tube in the retracted position and exposed from the outer tube in the advanced position; and
    an end effector releasably supported adjacent a distal end of the elongate body portion, the end effector including an engagement member and a plurality of surgical anchors, the engagement member of the end effector corresponding to the engagement member of the inner actuation shaft to facilitate releasable connection of the end effector to the elongate body portion, the end effector being releasable from the elongate body portion when the inner actuation shaft is positioned in the advanced position and secured to the elongate body portion when the inner actuation shaft is positioned in the retracted position,
    the end effector including an inner tube and an outer tube, the inner tube being positioned within the outer tube, wherein the inner tube includes a pair of opposed longitudinally extending tines and defines a pair of opposed longitudinally extending channels.

2. The endoscopic surgical device according to claim 1, wherein the engagement member of the inner actuation shaft is located at a distal end of the actuation shaft, and the engagement member of the end effector is located at a proximal end of the end effector.

3. The endoscopic surgical device according to claim 1, wherein the engagement member of the inner actuation shaft includes a recess, and the engagement member of the end effector includes a protrusion configured and dimensioned for positioning within the recess.

4. The endoscopic surgical device according to claim 1, wherein the inner actuation shaft is rotatable within outer tube, rotation of the inner actuation shaft being transmitted to the end effector via connection of the corresponding engagement members of the inner actuation shaft and the end effector.

5. The endoscopic surgical device according to claim 1, wherein the inner tube of the end effector is rotatably supported within the outer tube.

6. The endoscopic surgical device according to claim 1, wherein each anchor includes a threaded body portion and a head portion, the head portion defining a pair of opposed radially outer threads and a pair of opposed radial recesses, the pair of radial recesses of each head portion receiving the pair of tines of the inner tube of the end effector.

7. The endoscopic surgical device according to claim 6, wherein the outer tube of the end effector includes a helical thread along an inner surface thereof.

8. The endoscopic surgical device according to claim 7, wherein the outer threads of the head portion of each anchor project from the longitudinally extending channels defined by the inner tube of the end effector, and engage the helical thread of the outer tube of the end effector.

9. The endoscopic surgical device according to claim 1, further including a handle assembly supported adjacent a proximal end of the elongate body portion.

10. The endoscopic surgical device according to claim 9, wherein the handle assembly includes a handle housing, a trigger operatively connected to the handle housing, and a drive mechanism actuatable by the trigger.

11. The endoscopic surgical device according to claim 10, wherein the drive mechanism is connected to the inner actuation shaft such that actuation of the trigger results in rotation of the inner actuation shaft.

12. The endoscopic surgical device according to claim 1, wherein the elongate body portion includes a proximal portion and a distal portion, the distal portion pivotably connected to the proximal portion at a pivot point.

* * * * *